(12) United States Patent
Hematti et al.

(10) Patent No.: US 11,499,730 B2
(45) Date of Patent: Nov. 15, 2022

(54) LPS PRIMING OF STROMAL CELLS TO GENERATE LPS-SPECIFIC EXOSOME EDUCATED MACROPHAGES

(71) Applicant: Wisconsin Alumni Research Foundation, Madison, WI (US)

(72) Inventors: Peiman Hematti, Middleton, WI (US); John A. Kink, Madison, WI (US); Christian Capitini, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 628 days.

(21) Appl. No.: 16/273,712

(22) Filed: Feb. 12, 2019

(65) Prior Publication Data
US 2019/0249144 A1 Aug. 15, 2019

Related U.S. Application Data

(60) Provisional application No. 62/629,479, filed on Feb. 12, 2018.

(51) Int. Cl.
| | |
|---|---|
| *C12N 5/0786* | (2010.01) |
| *C12N 5/0775* | (2010.01) |
| *F24F 11/30* | (2018.01) |
| *F24F 11/50* | (2018.01) |
| *C12N 5/077* | (2010.01) |
| *F24F 110/40* | (2018.01) |
| *F24F 110/10* | (2018.01) |

(52) U.S. Cl.
CPC ............ *F24F 11/30* (2018.01); *C12N 5/0645* (2013.01); *C12N 5/0656* (2013.01); *C12N 5/0663* (2013.01); *F24F 11/50* (2018.01); *C12N 2501/052* (2013.01); *F24F 2110/10* (2018.01); *F24F 2110/40* (2018.01)

(58) Field of Classification Search
None
See application file for complete search history.

(56) References Cited

U.S. PATENT DOCUMENTS

| | | | |
|---|---|---|---|
| 8,647,678 | B2 | 2/2014 | Hematti |
| 8,802,144 | B2 | 8/2014 | Schmuck |
| 2011/0045071 | A1 | 2/2011 | Hematti |
| 2016/0082042 | A1 | 3/2016 | Hematti |
| 2016/0354447 | A1 | 12/2016 | Schmuck |
| 2018/0282698 | A1 | 10/2018 | Hematti |
| 2019/0134090 | A1 | 5/2019 | Hematti |

FOREIGN PATENT DOCUMENTS

| | | |
|---|---|---|
| WO | 2015031376 | 3/2015 |

OTHER PUBLICATIONS

Aldo et al, Am J Reprod Immunol, Jul. 2013, 70(1):80-86 (Year: 2013).*
Aggarwal S, et al. Human mesenchymal stem cells modulate allogeneic immune cell responses. Blood Feb. 15, 2005;105(4):1815-1822.
Arias, M. A., et al. "Glucopyranosyl Lipid Adjuvant (GLA), a Synthetic TLR4 Agonist." (2012).
Bernardo ME, et al. Mesenchymal stromal cells: sensors and switchers of inflammation. Cell Stem Cell. Oct. 3, 2013;13(4):392-402.
Blazquez R, et al. Immunomodulatory Potential of Human Adipose Mesenchymal Stem Cells Derived Exosomes on in vitro Stimulated T Cells. Front Immunol. 2014;5:556.
Bloom DD, et al. A reproducible immunopotency assay to measure mesenchymal stromal cell-mediated T-cell suppression. Cytotherapy. Feb. 2015; 17(2):140-151.
Bouchlaka MN, et al. Human Mesenchymal Stem Cell-Educated Macrophages Are a Distinct High IL-6-Producing Subset that Confer Protection in Graft-versus-Host-Disease and Radiation Injury Models. Biol Blood Marrow Transplant. Jun. 2017;23(6):897-905.
Caplan Al, et al. The MSC: an injury drugstore. Cell Stem Cell. Jul. 8, 2011;9(1):11-15.
Chiossone L, et al. Mesenchymal Stromal Cells Induce Peculiar Alternatively Activated Macrophages Capable of Dampening Both Innate and Adaptive Immune Responses. Stem Cells. Jul. 2016;34(7):1909-1921.
Cho DI, et al. Mesenchymal stem cells reciprocally regulate the M1/M2 balance in mouse bone marrow-derived macrophages. Exp Mol Med. Jan. 10, 2014;46:e70.
Choi JS, et al. The matricellular protein CCN1 promotes mucosal healing in murine colitis through IL-6. Mucosal Immunol. Nov. 2015;8(6):1285-1296.
Chow A, et al. CD169(+) macrophages provide a niche promoting erythropoiesis under homeostasis and stress. Nat Med. Apr. 2013;19(4):429-436.
Cooke KR, et al. An experimental model of idiopathic pneumonia syndrome after bone marrow transplantation: I The roles of minor H antigens and endotoxin. Blood. Oct. 15, 1996;88(8):3230-3239.
Denu, R.A., et al. "Fibroblasts and mesenchymal stromal/stem cells are phenotypically indistinguishable." Acta haematologica 136.2 (2016): 85-97.
Dominici M, et al. Minimal criteria for defining multipotent mesenchymal stromal cells. The International Society for Cellular Therapy position statement. Cytotherapy. 2006;8(4):315-317.
Duchez P, et al. Interleukin-6 enhances the activity of in vivo long-term reconstituting hematopoietic stem cells in "hypoxic-like" expansion cultures ex vivo. Transfusion Nov. 2015;55(11):2684-2691.
Eaton EB, Jr., et al. Mesenchymal stem cell therapy for acute radiation syndrome: innovative medical approaches in military medicine. Mil Med Res. 2015;2:2.
El Andaloussi, et al. Extracellular vesicles: biology and emerging therapeutic opportunities. Nat Rev Drug Discov. May 2013;12(5):347-357.
English K, et al. Cell contact, prostaglandin E(2) and transforming growth factor beta 1 play non-redundant roles in human mesenchymal stem cell induction of CD4+CD25(High) forkhead box P3+ regulatory T cells. Clin Exp Immunol. Apr. 2009; 156(1):149-160.

(Continued)

*Primary Examiner* — Allison M Fox
(74) *Attorney, Agent, or Firm* — McDonnell Boehnen Hulbert & Berghoff

(57) ABSTRACT

The disclosure relates to an ex vivo generated population of educated macrophages specific to LPS and methods of making and using such macrophages.

11 Claims, 18 Drawing Sheets
(17 of 18 Drawing Sheet(s) Filed in Color)

(56) References Cited

OTHER PUBLICATIONS

Evans JT et al., "Enhancement of antigen-specific immunity via the TLR4 ligands MPL™ adjuvant and Ribi. 529." Expert review of vaccines 2.2 (2003): 219-229.

Fernando MR, et al. The pro-inflammatory cytokine, interleukin-6, enhances the polarization of alternatively activated macrophages. PLoS One. 2014;9(4):e94188.

Fliedner TM, et al. Stem cells, multiorgan failure in radiation emergency medical preparedness: a U.S./European Consultation Workshop. Stem Cells. May 2009;27(5):1205-1211.

Galipeau J. The mesenchymal stromal cells dilemma—does a negative phase III trial of random donor mesenchymal stromal cells in steroid-resistant graft-versus-host disease represent a death knell or a bump in the road? Cytotherapy. Jan. 2013;15(1):2-8.

Goff PH et al. "Synthetic Toll-Like Receptor 4 (TLR4) and TLR7 Ligands as Influenza Virus Vaccine Adjuvants Induce Rapid, Sustained, and Broadly Protective Responses." Journal of Virology 89.6 (2015): 3221.

Gordon S, et al. Alternative activation of macrophages: mechanism and functions. Immunity. May 28, 2010;32(5):593-604.

Hallahan DE, et al. Intercellular adhesion molecule 1 knockout abrogates radiation induced pulmonary inflammation. Proc Natl Acad Sci U S A Jun. 10, 1997;94(12):6432-6437.

Hu J, et al. Infusion of Trx-1-overexpressing hucMSC prolongs the survival of acutely irradiated NOD/SCID mice by decreasing excessive inflammatory injury PLoS One. 2013;8(11):e78227.

Hu KX, et al. The radiation protection and therapy effects of mesenchymal stem cells in mice with acute radiation Injury. Br J Radiol. Jan. 2010;83(985):52-58.

Jacobsen RN, et al. Macrophages and regulation of erythropoiesis. Curr Opin Hematol. May 2015;22(3):212-219.

Katsuda T, et al. The therapeutic potential of mesenchymal stem cell-derived extracellular vesicles. Proteomics. May 2013;13(10-11):1637-1653.

Keil F, et al. Ex vivo expansion of long-term culture initiating marrow cells by IL-10, SCF, and IL-3. Transfusion. May 2002;42(5):581-587.

Kim J, et al. Comparison of breast and abdominal adipose tissue mesenchymal stromal/stem cells in support of proliferation of breast cancer cells. Cancer Invest. Oct. 2013;31(8):550-554.

Kim J, et al. Mesenchymal stem cell-educated macrophages: a novel type of alternatively activated macrophages. Exp Hematol. Dec. 2009;37(12):1445-1453.

Koc On, et al. Rapid hematopoietic recovery after coinfusion of autologous-blood stem cells and culture-expanded marrow mesenchymal stem cells in advanced breast cancer patients receiving high-dose chemotherapy. J Clin Oncol. Jan. 2000;18(2):307-316.

Kondo M, et al. Contribution of the Interleukin-6/STAT-3 Signaling Pathway to Chondrogenic Differentiation of Human Mesenchymal Stem Cells. Arthritis Rheumatol. May 2015;67(5):1250-1260.

Koukourakis MI. Radiation damage and radioprotectants: new concepts in the era of molecular medicine. Br J Radiol. Apr. 2012;85(1012):313-330.

Lai RC, et al. Mesenchymal stem cell exosomes. Semin Cell Dev Biol. Apr. 2015;40:82-88.

Lange C, et al. Radiation rescue: mesenchymal stromal cells protect from lethal irradiation. PLoS One. Jan. 5, 2011;6(1):e14486.

Lee, CC et al., "Accessory molecules for Toll-like receptors and their function." Nature Reviews Immunology 12.3(2012): 168.

Linden J. Molecular approach to adenosine receptors: receptor-mediated mechanisms of tissue protection. Annu Rev Pharmacol Toxicol. 2001;41:775-787.

Lombardo E, et al. Mesenchymal stem cells as a therapeutic tool to treat sepsis. World J Stem Cells. Mar. 26, 2015;7(2):368-379.

Meisel R, et al. Human bone marrow stromal cells inhibit allogeneic T-cell responses by indoleamine 2,3-dioxygenase-mediated tryptophan degradation. Blood. Jun. 15, 2004;103(12):4619-4621.

Melief SM, et al. Multipotent stromal cells induce human regulatory T cells through a novel pathway involving skewing of monocytes toward anti-inflammatory macrophages. Stem Cells. Sep. 2013;31(9):1980-1991.

Nemeth K, et al. Bone marrow stromal cells attenuate sepsis via prostaglandin E(2)-dependent reprogramming of host macrophages to increase their interleukin-10 production. Nat Med. Jan. 2009;15(1):42-49.

Phinney DG, et al. Concise Review: MSC-Derived Exosomes for Cell-Free Therapy. Stem Cells. Apr. 2017;35(4):851-858.

Pittenger M. Sleuthing the source of regeneration by MSCs. Cell Stem Cell. Jul. 2, 2009;5(1):8-10.

Pittenger MF, et al. Multilineage potential of adult human mesenchymal stem cells. Science. Apr. 2, 1999;284(5411):143-147.

Raposo et al., "B lymphocytes secrete antigen-presenting vesicles." Journal of Experimental Medicine 183.3 (1996):1161-1172.

Roberts CA, et al. The Interplay Between Monocytes/Macrophages and CD4(+) T Cell Subsets in Rheumatoid Arthritis. Front Immunol. 2015;6:571.

Roszer T. Understanding the Mysterious M2 Macrophage through Activation Markers and Effector Mechanisms. Mediators Inflamm. 2015;2015:816460.

Shim S, et al. Mitigating effects of hUCB-MSCs on the hematopoietic syndrome resulting from total body irradiation. Exp Hematol. Apr. 2013;41(4):346-353 e342.

Asimakopoulos F, et al. Macrophages in multiple myeloma: Emerging concepts and therapeutic implications. Leuk Lymphoma. 2013;54:2112-2121.

Bashir S, et al. Macrophage polarization: The link between inflammation and related diseases. Inflamm Res. 2016;65:1-11.

Chakravarty T, et al. Allogeneic heart stem cells to achieve myocardial regeneration (allstar) trial: Rationale & design. Cell transplantation. 2016.

Danon, David, et al. "Treatment of human ulcers by application of macrophages prepared from a blood unit." Experimental gerontology 32.6 (1997): 633-641.

De Silva R, et al. X-ray fused with magnetic resonance imaging (xfm) to target endomyocardial injections: Validation in a swine model of myocardial infarction. Circulation. 2006;114:2342-2350.

Fujiu K, et al. Cardioprotective function of cardiac macrophages. Cardiovascular research. 2014;102:232-239.

Hatt CR, et al. Mri-3d ultrasound-x-ray image fusion with electromagnetic tracking for transendocardial therapeutic injections: In-vitro validation and in-vivo feasibility. Comput Med Imaging Graph. 2013;37:162-173.

Huang P, et al. New strategies for improving stem cell therapy in ischemic heart disease. Heart Fail Rev. 2016;21:737-752.

Humeres, Claudio, et al. "Cardiac fibroblast cytokine profiles induced by proinflammatory or profibrotic stimuli promote monocyte recruitment and modulate macrophage M1/M2 balance in vitro." Journal of molecular and cellular cardiology 101 (2016): 69-80.

Ibrahim AG, et al. Exosomes as critical agents of cardiac regeneration triggered by cell therapy. Stem Cell Reports. 2014;2:606-619.

Kishore R, et al. More than tiny sacks: Stem cell exosomes as cell-free modality for cardiac repair. Circ Res. 2016;118:330-343.

Kovacic JC, et al. Safety and efficacy of consecutive cycles of granulocyte-colony stimulating factor, and an intracoronary cd133+ cell infusion in patients with chronic refractory ischemic heart disease: The g-csf in angina patients with ihd to stimulate neovascularization (gain i) trial. American heart journal. 2008;156:954-963.

Lalit PA, et al. Lineage reprogramming of fibroblasts into proliferative induced cardiac progenitor cells by defined factors. Cell Stem Cell. 2016;18:354-367.

Lian X, et al. Robust cardiomyocyte differentiation from human pluripotent stem cells via temporal modulation of canonical wnt signaling. Proceedings of the National Academy of Sciences of the United States of America. 2012;109:E1848-1857.

Losordo DW, et al. A randomized, controlled pilot study of autologous cd34+ cell therapy for critical limb ischemia. Circulation. Cardiovascular interventions. 2012;5:821-830.

(56) References Cited

OTHER PUBLICATIONS

Mantovani, Alberto, et al. "The chemokine system in diverse forms of macrophage activation and polarization." Trends in immunology 25.12 (2004): 677-686.
Martinez, F.O., et al. "Alternative activation of macrophages: an immunologic functional perspective." Annual review of immunology 27 (2009): 451-483.
Menasche P, et al. Stem cells for the treatment of heart failure. Curr Res Transl Med. 2016;64:97-106.
Mosser, D.M. "The many faces of macrophage activation." Journal of leukocyte biology 73.2 (2003): 209-212.
Mosser, D.M. et al. "Exploring the full spectrum of macrophage activation." Nature reviews immunology 8.12 (2008): 958.
Pollard, J. W. "Trophic macrophages in development and disease." Nature reviews immunology 9.4 (2009): 259.
Povsic TJ, et al. The renew trial: Efficacy and safety of intramyocardial autologous cd34(+) cell administration in patients with refractory angina. JACC. Cardiovascular interventions. 2016;9:1576-1585.
Prathipati P, et al. Stem cell-derived exosomes, autophagy, extracellular matrix turnover, and mimas in cardiac regeneration during stem cell therapy. Stem Cell Rev. 2016.
Raval AN, et al. Bilateral administration of autologous cd133+ cells in ambulatory patients with refractory critical limb ischemia: Lessons learned from a pilot randomized, double-blind, placebo-controlled trial. Cytotherapy. 2014;16:1720-1732.
Raval AN, et al. Cellular therapies for heart disease: Unveiling the ethical and public policy challenges. Journal of molecular and cellular cardiology. 2008;45:593-601.
Raval AN. Therapeutic potential of adult progenitor cells in the management of chronic myocardial ischemia. American journal of cardiovascular drugs : drugs, devices, and other interventions. 2008;8:315-326.
Schmuck EG, et al. Cardiac fibroblast-derived 3d extracellular matrix seeded with mesenchymal stem cells as a novel device to transfer cells to the ischemic myocardium. Cardiovascular Engineering and Technology. 2014;5:119-131.
Schmuck EG, et al. Intravenous followed by x-ray fused with mri-guided transendocardial mesenchymal stem cell injection improves contractility reserve in a swine model of myocardial infarction. Journal of cardiovascular translational research. 2015;8:438-448.
Shiraishi, Manabu, et al. "Alternatively activated macrophages determine repair of the infarcted adult murine heart." The Journal of clinical investigation 126.6 (2016): 2151-2166.
Spinali, Keith, et al. "Novel Cardiac Fibroblast-Derived Extracellular Matrix Educates Monocytes Into Alternatively Activated Macrophages With Low Inflammatory Marker Expression." Journal of the American College of Cardiology 71.11 (2018): A800.
Stout, R. D., et al. "Macrophages sequentially change their functional phenotype in response to changes in microenvironmental influences." The Journal of Immunology 175.1 (2005): 342-349.
Suzuki G. Translational research of adult stem cell therapy. World J Cardiol. 2015;7:707-718.
Tomkowiak MT, et al. Targeted transendocardial therapeutic delivery guided by mri-x-ray image fusion. Catheterization and cardiovascular interventions : official journal of the Society for Cardiac Angiography & Interventions. 2011;78:468-478.
Warrick JW, et al. High-content adhesion assay to address limited cell samples. Integr Biol (Camb). 2013;5:720-727.
Ye L, et al. Cardiac repair in a porcine model of acute myocardial infarction with human induced pluripotent stem cell-derived cardiovascular cells. Cell Stem Cell. 2014;15:750-761.
Zhang J, et al. Extracellular matrix promotes highly efficient cardiac differentiation of human pluripotent stem cells: The matrix sandwich method. Circulation research. 2012;111:1125-1136.
Zhang J, et al. Functional cardiomyocytes derived from human induced pluripotent stem cells. Circulation research. 2009;104:e30-41.
Zuloff-Shani, A., et al. "Macrophage suspensions prepared from a blood unit for treatment of refractory human ulcers." Transfusion and apheresis science 30.2 (2004): 163-167.
Zwetsloot PP, et al. Cardiac stem cell treatment in myocardial infarction: A systematic review and meta-analysis of preclinical studies. Circ Res. 2016;118:1223-1232.
Sica A, et al. Macrophage plasticity and polarization: in vivo veritas. J Clin Invest. Mar. 2012;122(3):787-795.
Sindrilaru A, et al. An unrestrained proinflammatory M1 macrophage population induced by iron impairs wound healing in humans and mice. J Clin Invest. Mar. 2011;121(3):985-997.
Singh VK, et al. A review of radiation countermeasures focusing on injury-specific medicinals and regulatory approval status: part I. Radiation sub-syndromes, animal models and FDA-approved countermeasures. Int J Radiat Biol. Sep. 2017;93(9):851-869.
Singh VK, et al. A review of radiation countermeasures focusing on injury-specific medicinals and regulatory approval status: part II. Countermeasures for limited indications, internalized radionuclides, emesis, late effects, and agents demonstrating efficacy in large animals with or without FDA IND status. Int J Radiat Biol. Sep. 2017;93(9):870-884.
Singh VK, et al. Colony-stimulating factors for the treatment of the hematopoietic component of the acute radiation syndrome (H-ARS): a review. Cytokine. Jan. 2015;71(1):22-37.
Stoorvogel et al. "The biogenesis and functions of exosomes." Traffic 3.5 (2002): 321-330.
Tasso R, et al. Mesenchymal stem cells induce functionally active T-regulatory lymphocytes in a paracrine fashion and ameliorate experimental autoimmune uveitis. Invest Ophthalmol Vis Sci. Feb. 2012;53(2):786-793.
Thery C, et al. Isolation and characterization of exosomes from cell culture supernatants and biological fluids. Curr Protoc Cell Biol. Apr. 2006;Chapter 3:Unit 3 22.
Ti, et al., LPS-preconditioned mesenchymal stromal cells modify macrophage polarization for resolution of chronic inflammation via exosome-shuttled let-7b, J. Transl. Med. (2015) 13:308, pp. 1-14.
Wang S, et al. Clinical applications of mesenchymal stem cells. J Hematol Oncol. 2012;5:19.
Wang Z, et al. miRNA let-7b modulates macrophage polarization and enhances tumor-associated macrophages to promote angiogenesis and mobility in prostate cancer. Sci Rep. May 9, 2016;6:25602.
Wen S, et al. Mesenchymal stromal cell-derived extracellular vesicles rescue radiation damage to murine marrow hematopoietic cells. Leukemia. Nov. 2016;30(11):2221-2231.
Williams JP, et al. Animal models for medical countermeasures to radiation exposure. Radiat Res. Apr. 2010;173(4):557-578.
Yang L, et al. ICAM-1 regulates neutrophil adhesion and transcellular migration of TNF-alpha-activated vascular endothelium under flow. Blood. Jul. 15, 2005;106(2):584-592.
Yao Y, et al. Lipopolysaccharide preconditioning enhances the efficacy of mesenchymal stem cells transplantation in a rat model of acute myocardial infarction. J Biomed Sci. Aug. 20, 2009;16:74.
Yu B, et al. Exosomes derived from mesenchymal stem cells. Int J Mol Sci. 2014;15(3):4142-4157.
Zhang Y, et al. Effect of exosomes derived from multipluripotent mesenchymal stromal cells on functional recovery and neurovascular plasticity in rats after traumatic brain injury. J Neurosurg. Apr. 2015;122(4):856-867.
Zhu YG, et al. Human mesenchymal stem cell microvesicles for treatment of *Escherichia coli* endotoxin-induced acute lung injury in mice. Stem Cells. Jan. 2014;32(1):116-125.

\* cited by examiner

FIGS. 1A-1D
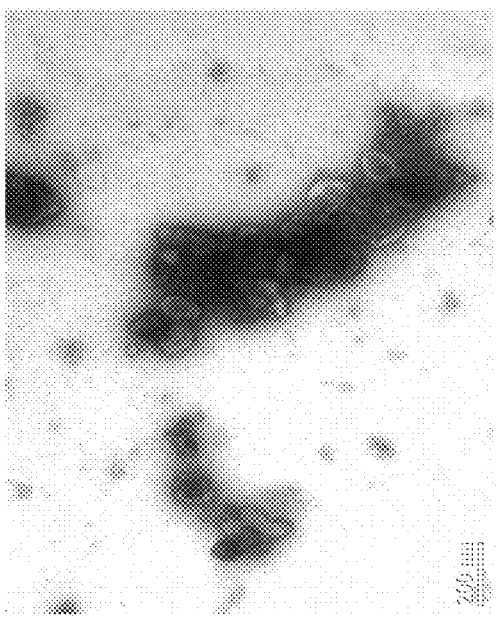
A
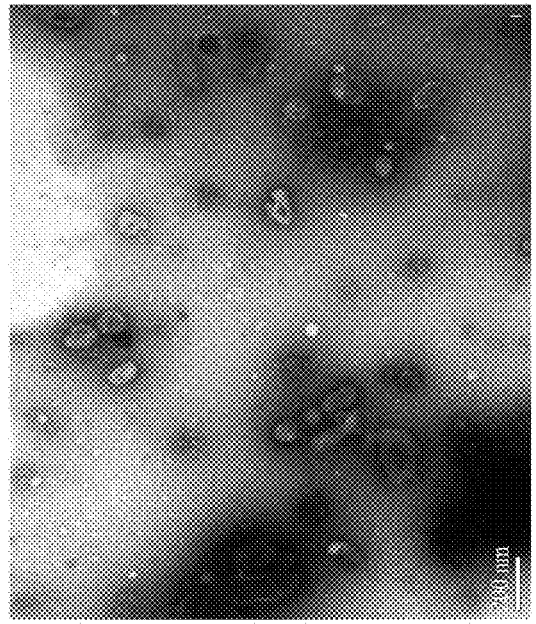
B

FIGS. 1A-1D CONTINUED
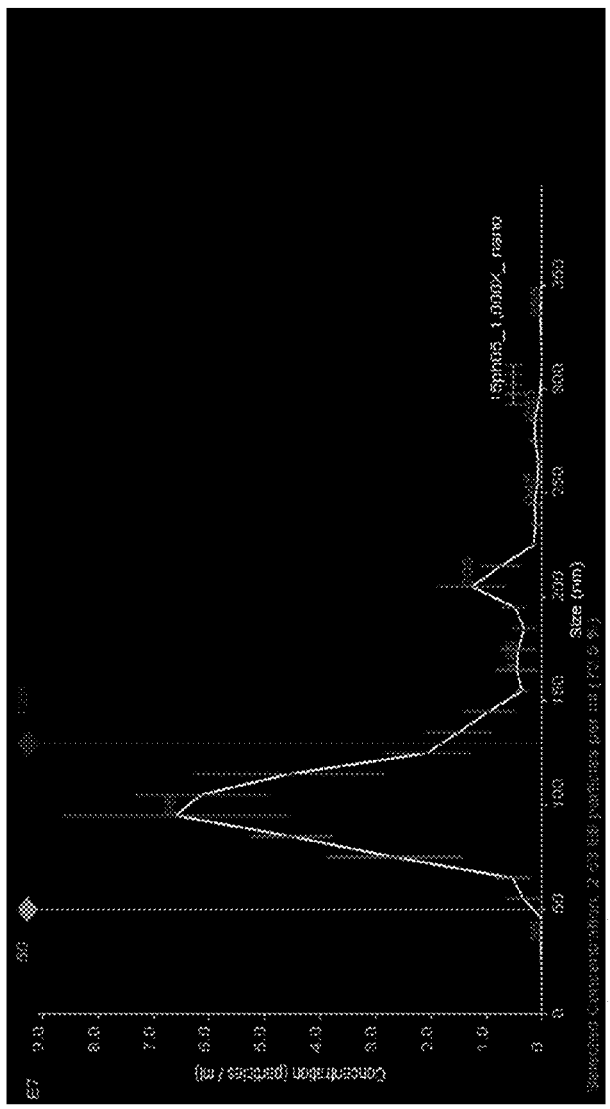
C
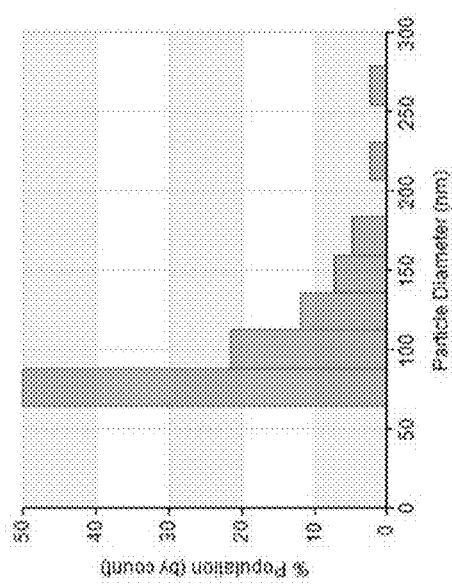
D

LPS PRIMING OF STROMAL CELLS TO GENERATE LPS-SPECIFIC EXOSOME EDUCATED MACROPHAGES

CROSS-REFERENCE TO RELATED APPLICATIONS

This application claims priority to U.S. Provisional Application No. 62/629,479, filed Feb. 12, 2018, which is incorporated herein by reference in its entirety.

STATEMENT REGARDING FEDERALLY SPONSORED RESEARCH

This invention was made with government support under CA014520 awarded by the National Institutes of Health. The government has certain rights in the invention.

BACKGROUND

Radiation, delivered therapeutically, accidentally, or maliciously, can lead to an acute radiation syndrome (ARS) with life threatening toxicities. High-dose radiation causes damage to highly proliferative cells such as those found in the bone marrow, GI-tract and skin. Current standard of care involves supporting victims with antibiotics and transfusions until they can undergo an allogeneic bone marrow transplant (BMT) from a suitable donor. Unfortunately, the entire BMT process can often take weeks to identify and collect cells from a donor, and are difficult to perform on a large-scale in the event of a widespread exposure. Moreover, allogeneic BMTs have their own set of complications, including engraftment failure, opportunistic infections and/or graft-versus-host-disease (GVHD), making them potentially as toxic as the radiation injury itself. Consequently, adjunct therapies have received special attention for treatment of radiation injury, but to date, the only approved treatment agents are colony-stimulating factors such as G-CSF. Unfortunately, for these factors to be effective the patient's own hematopoietic stem cells have to be spared from radiation effects.

Attractive alternatives to treat ARS focus on allogeneic, "off-the-shelf" cell-based therapies that can accelerate the repair of tissue injury after radiation without relying on the patient's own remaining healthy cells. Ideally, cell-based therapies can be cryopreserved and ready for a quick infusion without extensive tissue matching to the recipient. Among the stromal cells currently explored are multipotent mesenchymal stem cells (MSCs) derived from the bone marrow (BM) or tissue fibroblasts. MSCs are capable of self-renewal and differentiation into osteocytes, chondrocytes and adipocytes, making them attractive candidates to treat tissue injury. MSCs have strong immunosuppressive properties and can control inflammation by modifying the proliferation and cytokine production of immune cells. Fibroblasts are also useful to treat tissue injury and are very similar to MSCs in many properties such as morphology, surface marker profile and ability to differentiate into other tissues. (Denu et al. Acta Haematol. 2016; 136(2):85-97) MSCs have shown promise in preclinical studies in rodent models of radiation injury and have spurred human clinical trials for treating autoimmune and degenerative diseases. However, while therapeutic MSCs show promise, they often fail to demonstrate clear efficacy in many clinical trials, and have not yet been approved to treat ARS.

While studies indicate that MSCs promote tissue repair based on their differentiation potential, the lack of correlation between cell engraftment and differentiation at the site of injury with functional improvement suggest that MSCs achieve in vivo therapeutic effects by communicating with other effector cells. MSCs are thought to exert therapeutic effects via antigen-presenting cells (APCs) such as monocytes and macrophages. Macrophages can polarize generally into two broad phenotypes: classically activated (M1) macrophages, which mediate tissue damage and are considered "pro-inflammatory", or alternatively activated (M2) macrophages, which contribute to wound healing and tissue repair and are "anti-inflammatory". Direct co-culture of MSCs with macrophages educates the macrophages to MSC-educated macrophages (MEMs) that increase the expression of specific surface markers (CD206) and cytokines (IL-6 and IL-10). The therapeutic utility of macrophage education by MSCs was demonstrated by enhanced survival from lethal radiation injury using a xenogeneic mouse model treated with MEMs as compared to infusions of MSCs or macrophages alone.

While advancements have been made in the treatment of acute radiation syndrome and other diseases using MSCs and MEMs, a need exists in the art for further development of new treatment methods and compositions utilizing both MSCs and alternatively activated educated macrophages.

SUMMARY OF THE INVENTION

In a first aspect, provided herein is a method for generating an educated macrophage, the method comprising the steps of isolating an extracellular vesicle from a mesenchymal stromal cell previously exposed to lipopolysaccharide (LPS), and co-culturing a CD14+ cell with the extracellular vesicle in vitro until the CD14+ cell acquires an anti-inflammatory macrophage phenotype. In some embodiments, the CD14+ cell and the extracellular vesicle are co-cultured for at least 2 days. In some embodiments, the mesenchymal stromal cell is exposed to LPS for at least 2 hours. In some embodiments, the mesenchymal stromal cell is exposed to about 50 ng/ml to about 200 ng/ml LPS. In some embodiments, the mesenchymal stromal cell is exposed to about 800 ng/ml to about 1200 ng/ml LPS. In some embodiments, the mesenchymal stromal cell is a mesenchymal stem cell. In some embodiments, the mesenchymal stromal cell is a fibroblast. In some embodiments, the CD14+ cell is a macrophage. In some embodiments, the CD14+ cell is a monocyte and wherein the CD14+ monocyte and the extracellular vesicle are co-cultured for at least 5 days.

In a second aspect, provided herein is a population of anti-inflammatory macrophages produced by the methods described herein wherein the mesenchymal stromal cell is exposed to about 50 ng/ml to about 200 ng/ml LPS, wherein the anti-inflammatory macrophage phenotype is characterized as CD206 high, PD-L1 high, PD-L2 high, CD16 high and CD73 high compared to control macrophages.

In a third aspect, provided herein is a population of anti-inflammatory macrophages produced by the methods described herein wherein the mesenchymal stromal cell is exposed to about 800 ng/ml to about 1200 ng/ml LPS, wherein the anti-inflammatory macrophage phenotype is characterized as FLT-3L high, IL-15 high, CD73 high, CD86 low, and HLA-DR low as compared to control macrophages.

In a forth aspect, provided herein is a method for generating an educated monocyte, the method comprising the steps of isolating an extracellular vesicle from a mesenchymal stromal cell previously exposed to lipopolysaccharide (LPS), and co-culturing a CD14+ monocyte with the extracellular vesicle in vitro until the CD14+ monocyte acquires an anti-inflammatory monocyte phenotype. In some embodiments, the CD14+ monocyte and the extracellular vesicle are co-cultured for at least 2 hours. In some embodiments, the CD14+ monocyte and the extracellular vesicle are co-cultured for at least 24 hours. In some embodiments, the mesenchymal stromal cell is exposed to LPS for at least 12 hours. In some embodiments, the mesenchymal stromal cell is exposed to about 50 ng/ml to about 200 ng/ml LPS. In some embodiments, the mesenchymal stromal cell is exposed to about 800 ng/ml to about 1200 ng/ml LPS. In some embodiments, the mesenchymal stromal cell is a mesenchymal stem cell. In some embodiments, the mesenchymal stromal cell is a fibroblast.

In a fifth aspect, provided herein is a population of anti-inflammatory monocytes produced by the method in the fifth aspect disclosed herein, wherein the anti-inflammatory monocyte phenotype is characterized as PD-L1 high, CD206 low, CD163 low, IL-15 high, CD73 high, CD86 low, CD16 low and IL-6 high as compared to control monocytes.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

The invention will be better understood and features, aspects, and advantages other than those set forth above will become apparent when consideration is given to the following detailed description thereof. Such detailed description makes reference to the following drawings.

FIGS. 1A-1D demonstrate that extracellular vesicles (EVs) isolated from mesenchymal stem cells (MSCs), include small exosomes (50-250 nm) and larger microvesicles (500-1000 nm), and exosome-sized EVs predominate among the isolated EVs. EVs were isolated from bone marrow mesenchymal stem cells (BM-MSC) as described in the Examples, and EVs were analyzed by TEM and two different instruments to quantify the mean and mode of the particle diameter and particle concentration. (A and B) TEM of two different preparations indicated that the particles had the typical cup-shaped vesicular appearance of EVs and generally measured less than 250 nm. (C) The preparations characterized by dynamic light scattering using the Nanosight NS300 indicated that the majority of particles were 95 nm with a range of 50 to 250 nm. (D) The preparations characterized by resistive pulse sensing using the qNano Nanoparticle instrument matched the characterization obtained from the Nanosight NS300 and also indicated that the majority of the particles are in the 50-250 nm range. Based on these characterizations the majority of the particles were primarily exosomes-sized EVs.

FIG. 5A compares the gene expression of IL-6. FIG. 5B compares the gene expression of IL-8, IDO and FGF2. FIG. 5C compares the gene expression of IL-15, IL-10, IL-12, VEGF-A, EGF and IL-7. P values were determined compared to controls; *$p</=0.05$,  $p</=0.01$, * $p</=0.001$, **** $p</=0.0001$.

FIG. 5A shows a graph of the survival curve vs days post-challenge compared by log rank analysis. P value comparing LPS-high-EEMs to the other groups was >0.0001. (B) Mean % weight change vs days post-challenge compared with Day 0 for each group. P value comparing LPS-high-EEMs to the other groups was >0.0001. (C) Overall clinical score (weight loss, posture, activity and fur texture) vs days post-challenge. P value comparing LPS-high EEMs to the other groups was >0.0001.

FIG. 9A shows 20× images of H&E stained femoral bone marrow sections from each group. FIG. 9B shows 20× images of H&E stained spleen sections.

FIG. 10A shows a graph of the survival curve vs days post-challenge compared by log rank analysis. P value comparing LPS-high-EEMos to the other groups was >0.0001. FIG. 10B shows overall clinical score (weight loss, posture, activity and fur texture) vs days post-challenge. FIG. 10C shows mean percent weight change vs days post-challenge compared with Day 0 for each group. P value comparing LPS-high-EEMs to the other groups was >0.0001.

FIG. 12A shows a graph of the survival curve vs days post-challenge compared by log rank analysis. P value comparing treatment with LPS-high-EEMos, MSC-EVs, and LPS-high-EVs to PBS control was >0.001 and >0.01 respectively. FIG. 12B shows overall clinical score (weight loss, posture, activity and fur texture) vs days post-challenge. P value comparing treatment with LPS-high-EEMos to PBS control was >0.01. FIG. 12C shows mean percent weight change vs days post-challenge compared with Day 0 for each group.

DETAILED DESCRIPTION OF THE INVENTION

Figure 2:
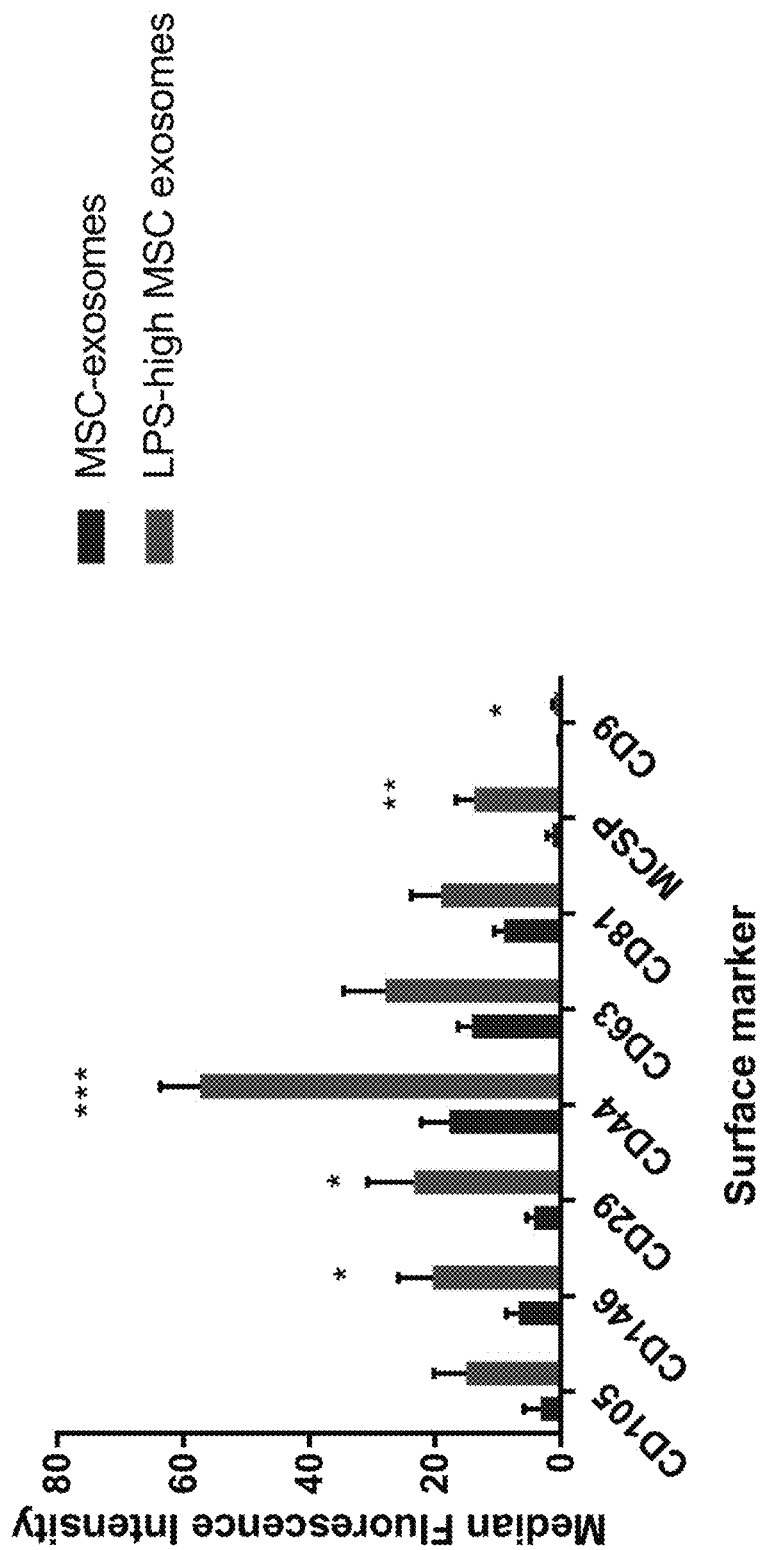
FIG. 2 shows the surface marker profile of the EVs from unstimulated MSCs (MSC-EVs) and LPS-high stimulated MSCs (LPS-high-EVs). The results shown represent samples from two different human MSC donors. A total of 37 known EV surface markers were examined. Surface markers positively identified on the EVs are expressed as mean fluorescence intensity (MEI)±SEM.

The present disclosure broadly relates to an educated CD14$^+$ cell (macrophage or monocyte) as well as methods for making and using such a cell. The educated CD14$^+$ cell may be a cell with an anti-inflammatory, immunosuppressive, tissue reparative phenotype. Methods of the present invention broadly relate to derivation of extracellular vesicles from LPS-treated mesenchymal stromal cells (LPS-EVs) and their use in a co-culture with CD14+ cells to generate LPS-specific educated macrophages (LPS-EEMs) or LPS-specific educated monocytes (LPS-EEMos). The disclosure also broadly relates to methods of treatment using LPS-EVs, LPS-EEMS, or LPS-EEMos.

In one aspect of the invention, mesenchymal stromal cells are cultured in the presence of LPS to generate LPS-primed stromal cells. Extracellular vesicles isolated from the LPS-primed stromal cells (LPS-EVs) are co-cultured with CD14$^+$ monocytes or macrophages to yield educated macrophages (LPS-EEMs) or educated monocytes (LPS-EEMos) with a characteristic cytokine profile, expression profile and phenotype as described herein. LPS-EVs, educated macrophages, or educated monocytes generated by the methods of the present invention may be used to treat or prevent a disease by administering the educated cells to a subject in need thereof.

As used herein, "educated macrophage" refers to a LPS-specific anti-inflammatory, tissue reparative, immunosuppressive macrophage generated ex vivo by co-culturing a CD14$^+$ monocyte or macrophage with an extracellular vesicle obtained from a LPS-treated mesenchymal stromal cell. In one embodiment, the educated macrophages are anti-inflammatory, immunosuppressive, and tissue reparative macrophages generated by co-culturing CD14$^+$ monocytes or macrophages with extracellular vesicles derived from LPS-primed MSCs. In one embodiment, the educated macrophages are anti-inflammatory, immunosuppressive, and tissue reparative macrophages generated by co-culturing CD14$^+$ monocytes or macrophages with extracellular vesicles derived from LPS-primed fibroblasts.

As used herein, "educated monocyte" refers to a LPS-specific anti-inflammatory, tissue reparative, immunosuppressive monocyte generated ex vivo by co-culturing a $CD14^+$ monocyte with an extracellular vesicle obtained from a LPS-treated mesenchymal stromal cell. In one embodiment, the educated monocytes are anti-inflammatory, immunosuppressive, and tissue reparative monocytes generated by co-culturing $CD14^+$ monocytes with extracellular vesicles derived from LPS-primed MSCs. In one embodiment, the educated monocytes are anti-inflammatory, immunosuppressive, and tissue reparative monocytes generated by co-culturing $CD14^+$ monocytes with extracellular vesicles derived from LPS-primed fibroblasts.

Co-Culture $CD14^+$ cells are co-cultured with LPS-EVs to yield LPS-specific educated macrophages (LPS-EEMs) or LPS-specific educated monocytes (LPS-EEMos). Methods of co-culturing $CD14^+$ cells with mesenchymal stem cells (MSCs), mesenchymal stromal cells, or tissue-specific extracellular vesicles (EVs) to generate MSC-educated macrophages (referred to herein as BM-MEM) or exosome educated macrophages (EEMs), respectively, have been described, see U.S. Pat. No. 8,647,678 and U.S. Patent Publication No. 2016/0082042, each of which is incorporated herein by reference.

$CD14^+$ cells are co-cultured ex vivo with LPS-EVs in any culture medium known in the art suitable for survival and growth of the co-culture components. $CD14^+$ cells may be co-cultured in culture plates, culture flasks or in hollow fiber systems. To generate educated monocytes, the co-cultures may be maintained for between 2 hours and 5 days. Co-cultures may generate educated monocytes with the desired immune-phenotype after 2 hours, 3 hours, 4 hours, 5 hours, 8 hours, 10 hours, 12 hours, 15 hours, 18 hours, 20 hours, 24 hours, 36 hours, 48 hours, 50 hours, 72 hours, 4 days, or 5 days. In some embodiments, co-cultures yield educated monocytes after 24 hours. In some embodiments, co-cultures yield educated monocytes after 48 hours. To generate educated macrophages, the co-cultures may be maintained for between 1-20 days. Co-cultures may generate educated macrophages with the desired immuno-phenotype after 1, 2, 3, 4, 5, 6, 7, 8, 9, 10, 11, 12, 13, 14, or more than 15 days. In some embodiments, co-cultures yield educated macrophages after 10 days. In some embodiments, co-cultures yield educated macrophages after 5 days. In some embodiments, co-cultures yield educated macrophages after 3 days. In one embodiment, co-cultures yield educated macrophages after 1 day. In general, to produce a population of educated macrophages starting with a population of $CD14^+$ monocytes, cells are co-cultured with LPS-EVs for at least 5 days to generate educated macrophages or $CD14^+$ monocytes are differentiated to macrophages and the resulting $CD14^+$ macrophages are co-cultured with LPS-EVs for at least one day to generate educated macrophages.

In some cases, LPS-EVs are subjected to additional purification steps prior to use in co-culture. LPS-EVs can be added in a single dose or repeated doses to $CD14^+$ cultures to generate educated $CD14^+$ cells. In one embodiment, an additional centrifugation step is added to separate exosomes from micro-vesicles and other extra-cellular vesicles.

For co-cultures of the present invention, monocytes or macrophages can be co-cultured with LPS-EVs such that the cells are in direct physical contact with the extracellular vesicles. Alternatively, the co-culture components can be placed in sub-compartments that are in fluid communication but separated by a semi-permeable membrane. The semi-permeable membrane allows the exchange of soluble medium components and factors secreted by the cells but not the cells per se. The pores within the semi-permeable membrane are sufficiently small to prevent cell penetration but large enough to allow soluble medium components to pass across the membrane, and are typically are between 0.1-1.0 µm, but other pore sizes can be suitable.

Various methods of cell separation and isolation are known in the art and can be used to separate the educated macrophages or educated monocytes from the LPS-EVs depending on factors such as the desired purity of the isolated cell populations. Macrophages are strongly adherent to solid culture surfaces and monocytes are weakly adherent to culture surfaces which may aid in separation and isolation of the educated $CD14^+$ cells. For example, educated macrophages or educated monocytes can be isolated from the co-culture using flow cytometry, magnetic-based sorting, scraping from plates, a digestive process (e.g., trypsinization and EDTA), or low speed centrifugation. In some embodiments, educated macrophages or educated monocytes can be separated from the LPS-EVs by removal of the culture medium containing the LPS-EVs followed by multiple washing steps. Educated macrophages can be maintained in culture in any medium that supports macrophages in vitro. Educated monocytes can be maintained in culture in any medium that supports monocytes in vitro. Also, educated macrophages or educated monocytes can be stored using methods known in the art including, but not limited to, refrigeration, cryopreservation, vitrification, and immortalization.

As used herein, "$CD14^+$ cell" refers to a monocyte or a macrophage. $CD14^+$ cells can be derived from any suitable source. The skilled artisan will appreciate the advantageous efficiency of generating macrophages from peripheral blood monocytes for co-cultures. Alternatively, macrophages can also be isolated from cellular outgrowth of a tissue sample taken from an individual or from pluripotent stem cells. Monocytes can be cultured for various times and under various conditions before co-culture or can be added to the exosomes or extracellular matrix directly for co-cultures. In one embodiment, monocytes are harvested from a subject by leukapheresis. In one embodiment, CD14+ cells are isolated from peripheral blood. In one embodiment, CD14+ cells are isolated from peripheral blood of a patient who has first been treated with an agent including but not limited to G-CSF, GM-CSF, Mozobil and the like to mobilize cells into the peripheral blood. In one embodiment, CD14+ cells are isolated from peripheral blood with G-CSF stimulation. In one embodiment CD14+ cells are isolated from bone marrow aspirates. In one embodiment CD14+ cells are isolated from tissues or organs of interest. In one embodiment CD14+ cells are derived from pluripotent stem cells such as embryonic stem cells or induced pluripotent stem cells.

As used herein "macrophage" refers to a mononuclear phagocyte characterized by the expression of CD14 and lack of expression of dendritic or mesenchymal cell markers.

As used herein "mononuclear leukocytes" or "monocytes" are white blood cells that can differentiate into macrophages when recruited to tissues and can influence both innate and adaptive immune system.

As used herein, "high" means that the cells are characterized by higher expression of a particular cytokine, chemokine, growth factor or cell surface marker compared to control macrophages or monocytes cultured under the same conditions without tissue-specific cells or extracellular factors. Expression of markers may be measured by any means known in the art, including but not limited to, gene expression analysis (qPCR), Western blot, secretion product measurement by ELISA, multiplex detection systems, transcriptome analysis or flow-cytometry. For example, "IL-6 high" indicates that macrophages co-cultured with tissue-specific cells or extracellular factors express higher amounts of IL-6 than macrophages that have not been co-cultured with tissue-specific cells or extracellular factors. Similarly, "low" means that the cells are characterized by lower expression of a particular cytokine. For example, "IL-12 low" indicate that macrophages co-cultured with tissue-specific cells or extracellular factors express lower amounts of IL-12 than macrophages that have not been co-cultured with tissue-specific cells or extracellular factors. "Low" can also mean that the expression levels or secretion levels are below the detection limit.

Primed Stromal Cells and Extracellular Vesicles

The skilled artisan will appreciate that monocytes, macrophages, mesenchymal stromal cells, fibroblasts, mesenchymal stem cells, and extracellular vesicles employed in methods described herein can be cultured or co-cultured in any medium that supports their survival and growth. In some embodiments, the medium is a serum-free medium supplemented with chemically defined mammalian serum supplement. In some embodiments the medium is supplemented serum-free medium including but not limited to X-VIVO™ 15, CTS™ STEMPRO™ MSC serum-free media (SFM), or STEMPRO™-34 SFM. One may also use conventional culture media with serum or an animal supplement depleted of endogenous EVs which may be present in the serum. EVs may be removed from the serum by means such as ultracentrifugation or ultrafiltration. Suitable serum from which endogenous EVs may be removed include but are not limited to fetal bovine serum, fetal calf serum, human serum, and human AB serum. For short term cultivation of about 1 day to about 3 days, conventional culture medium without serum has also been used. In one embodiment, the medium uses human platelet lysates to replace the human AB serum in the culture medium for macrophage and monocyte cultures. In some embodiments, in order to isolate EVs for the cells of interest, the culture medium is free of endogenous EVs present in either mammalian serum or protein supplements derived from humans or animals such as human platelet lysate. Mesenchymal stem cells, extracellular vesicles and macrophages can be autologous, syngeneic, allogeneic, or third party with respect to one another.

As used herein, "mesenchymal stromal cells" refers to mesenchymal stem cells (MSC) or fibroblasts.

As used herein, "mesenchymal stem cells (MSC)" refers to the fibroblast-like cells that reside within virtually all tissues of a postnatal individual. An ordinarily skilled artisan will appreciate that the cells referred to herein as mesenchymal stem cells are also known in the art as mesenchymal stromal cells, marrow stromal cells, multipotent stromal cells, and other names. An MSC within the scope of this disclosure is any cell that can differentiate into osteoblasts, chondrocytes, myocytes, and adipocytes. An MSC within the scope of this disclosure is positive for the expression of CD105, CD73, and CD90 while lacking expression of CD45, CD34, CD14 or CD11b, CD79a or CD19, and HLA-DR surface molecules. (Dominici et al. Minimal criteria for defining multipotent mesenchymal stromal cells. The International Society for Cellular Therapy position statement, (2006), Cytotherapy, 8(4):315-317). While these markers are known to characterize MSCs derived from most tissues, it is understood in the art that MSCs from some sources could exhibit differences in cell surface marker expression. Within bone marrow, MSCs provide the stromal support tissue for hematopoietic stem cells. MSCs can differentiate into cells of the mesenchymal lineage. In some embodiments, MSCs are co-cultured with $CD14^+$ cells to generate MSC-educated macrophages (referred to herein as MEMs). In some embodiments, the MSC are LPS-primed MSCs (LPS-MSCs) which have been cultured in the presence of LPS.

MSCs, fibroblasts, and other cells described herein for use in the methods or compositions of the present invention may be derived or isolated from any suitable source. MSCs and fibroblasts may be isolated from tissues including but not limited to bone marrow, lung, cornea, intestines, testis, tendon, adipose, muscle, liver, vertebral, umbilical, and amniotic. In one embodiment, MSCs are isolated from bone marrow (BM-MSCs). In one embodiment, MSCs are differentiated from embryonic- or induced pluripotent stem cells.

As used herein, "LPS mesenchymal stem cells (LPS-MSC)" refers to a mesenchymal stem cell that has been cultured in the presence of LPS. The MSCs may be cultured in the presence of LPS for at least about 2 hours. In some embodiments, the MSCs may be cultured in the presence of LPS for at least 12 hours (e.g., at least 10 hours, at least 12 hours, at least 15 hours, at least 18 hours, at least 24 hours, or at least 32 hours) in any suitable culture medium known in the art that will support the growth and survival of the MSCs. The LPS is present in the culture medium at a concentration of about 1 ng/ml to about 10 ug/ml.

The LPS used in priming of MSCs as described herein may be from any suitable source. Suitable sources include, but are not limited to, LPS from gram negative bacteria including *Escherichia, Salmonella, Neisseria, Hemophilus, Klebsiella, Campylobacter, Bacteroides, Helicobacter, Pseudomonas, Yersinia*, and *Shigella*. It is known in the art that LPS from various sources have varying degrees of endotoxic activity. A skilled artisan will recognize that in certain embodiments it may be advantageous to select a suitable LPS based on the endotoxic activity thereof.

In some embodiments, LPS may be replaced with another TLR4 ligand. Exemplary TLR4 ligands for use in the methods for priming MSCs described herein include LPS, VSV glycoprotein G, RSV fusion protein, MMTV envelope protein, mannan, glucuronoxylomannan, glycosylinositolphospholipids, HSP60, HSP70, fibrinogen, nickel, HMGB1 (from Lee, C C et al, Nature Reviews Immunology 12, 168-172 (2012)), 1Z105 (a substituted pyrimido[5,4-b]indole (Goff P H et al. J of Virology 89, 6 2015)), Glucopyranosyl Lipid Adjuvant (GLA) (Arias, M A et al. Plos One, PLOS ONE 7(7): e41144. 2012), and synthetic lipid A mimetics (aminoalkyl glucosaminide 4-phosphates, Evans J T et al., J of Expert Review of Vaccines, 2, 2003).

As used herein, "extracellular factors" refers collectively to extracellular vesicles, exosomes, micro-vesicles, extracellular matrix compositions, isolated extracellular matrix components and fragments or derivatives thereof, exosomes purified from an extracellular matrix, and combinations thereof. Extracellular factors are used in co-culture with $CD14^+$ cells to educate macrophages or monocytes in a tissue-specific manner. As used herein, "extracellular vesicles (EVs)" refers to both exosomes and micro-vesicles.

As used herein, "exosomes" refer to small lipid vesicles released by a variety of cell types. Exosomes are generated by inward- or reverse budding, resulting in particles that contain cytosol and exposed extracellular domains of certain membrane-associated proteins (Stoorvogel et al., *Traffic* 3:321-330 (2002)). Methods of preparing exosomes from cells are known in the art. See, for example, Raposo et al., *J. Exp. Med.* 183:1161 (1996). In one method, exosomes are recovered from conditioned culture medium by centrifugation. Exosomes suited for use in the methods can be derived fresh or can be previously frozen aliquots kept as a composition, thawed, and added in a single dose or repeated doses to CD14+ cultures to generate educated macrophages. In some embodiments, exosome preparations may also include micro-vesicles.

Exosomes can have, but are not limited to, a diameter of about 10-300 nm. In some embodiments, the exosomes can have, but are not limited to, a diameter between 20-250 nm, 30-200 nm or about 50-150 nm. Exosomes may be isolated or derived from any cell type that resides in the target tissue of interest which can be isolated and cultured for a period of time appropriate for the isolation of exosomes.

In one embodiment, the exosomes (LPS-EVs) are derived from MSCs primed with LPS (LPS-MSCs). In some embodiments, EVs are isolated from the LPS primed MSC culture by harvesting medium containing the EVs. Multiple cycles of EV isolation may be performed from a single population of MSCs in culture. For example, medium harvested from MSCs after a first LPS priming can be replaced with fresh media containing LPS for another round of LPS priming and EV isolation. In some embodiments, MSCs may be primed with LPS at a concentration of about 50 ng/ml to about 200 ng/ml (LPS-low). In some embodiments, MSCs may be primed with LPS at a concentration of about 50 ng/ml, about 100 ng/ml, about 125 ng/ml, about 150 ng/ml, about 175 ng/ml, or about 200 ng/ml (LPS-low). In some embodiments, MSCs may be primed with LPS at a concentration of about 800 ng/ml to about 1200 ng/ml (LPS-High). In some embodiments, MSCs may be primed with LPS at a concentration of at least about 800 ng/ml, at least about 850 ng/ml, at least about 900 ng/ml, at least about 950 ng/ml, at least about 1000 ng/ml, at least about 1050 ng/ml, at least about 1100 ng/ml, at least about 1150 ng/ml, or at least about 1200 ng/ml (LPS-high). In some embodiments MSCs may be primed with LPS at a concentration of at most about 1200 ng/ml, at most about 1100 ng/ml, at most about 1050 ng/ml, or at most about 1000 ng/ml. When surface markers are examined by flow cytometry, the LPS-high-EVs are positive for CD105, CD146, CD29, CD44, CD63, CD81, MSCP and CD9.

LPS-exosomes derived from LPS-MSCs (LPS-EVs) are co-cultured with CD14+ cells to generate LPS-specific exosome-educated macrophages (referred to herein as LPS-EEMs), which are immunosuppressive, reparative, anti-inflammatory macrophages. LPS-low-EEMs are generated from LPS-low-EVs and LPS-high-EEMs are generated from LPS-high-EVs, wherein high and low indicate the relative concentration of LPS used to culture MSCs. When comparing by flow cytometry the external surface markers of LPS-low EEMs to the markers of control macrophages, the LPS-low EEMs show a significant increase in the intensity of marker expression (MFI) of CD206, PD-L1, and CD16 with a significant decreases in M1 markers in CD86 and HLA-DR. LPS-low EEMs also show a significant increase in percentage of cells (% cells) expressing CD206, PD-L1, PD-L2, CD16, and CD73 as well as a significant decrease in CD86. Comparing surface markers of control macrophages to LPS-high EEMs, there were significant decreases in the MFI of CD86 and HLA-DR with significant increases in the % cells expressing CD73 but decreases in CD86. Gene expression analysis of LPS-high-EEMs and LPS-low-EEMs by qPCR shows statistical increases in IL-10, IDO, IL-6, VEGF-A, Stat1 and Stat3, TNF-alpha and IL-8, and a statistical decreases in IL-12 as compared to control macrophages. Comparing secreted cytokine/chemokine profile to control macrophages by multiplex ELISA demonstrated significant increases in LPS-low and/or LPS-high EEMs of the following analytes; EGF, FGF-2, EOTAXIN, TGF-a, G-CSF, FLT-3L, GM-CSF, FRACTALKINE, INFa2, IFNg, GRO, IL-10, MCP-3, IL-12p40, IL-12p70, IL-13, PDGF-BB, IL-15, sCD40L IL-17, IL-1a, IL-1b, IL-2, IL-4, IL-5, IL-7, IL-8, IP-10, MIP-1a, MIP-1b, TNFa, and VEGF. The functions of analytes secreted in high levels by the LPS-EEMs include: growth factors for wound healing (EGF, FGF-2, TGF-a), vascular growth factors (VEGF-A), hematopoietic growth factors (G-CSF, GM-CSF, FLT-3L, IL-7) chemotactic or chemoattractant chemokines (EOTAXIN, FRACTALKINE, GRO, MCP-3, IP-10), anti-inflammatory cytokines (IL-4, IL-10, IL-13) immuno-modulating factors (INFa2, IFNg, IL-17, IL-1a, IL-9, IL-5) and platelet activating factors (PDGF-BB, sCD40L).

LPS-EVs are co-cultured with CD14+ monocytes to generate LPS-specific exosome-educated monocytes (referred to herein as LPS-EEMos), which are immunosuppressive, reparative, anti-inflammatory monocytes. LPS-low-EEMos are generated from LPS-low-EVs and LPS-high-EEMos are generated from LPS-high-EVs, wherein high and low indicate the relative concentration of LPS used to culture MSCs. When compared by flow cytometry, the external surface markers of LPS-high-EEMos show a significant increase in the percentage of cells positive for CD73 and PD-L1 and a significant decrease in expression of CD163, CD16, CD206, PD-L2 and CD86 compared to control monocytes. By flow cytometry, the external surface markers of LPS-high-EEMos show a significant increase in the percentage of cells positive for PD-L1 and significant decreases in CD16, CD206, CD86 and CD73 compared to EEMos generated by co-culture with EVs derived from MSCs that have not been primed with LPS. Gene expression studies of the LPS-high-EEMos by qPCR showed statistical increases in IL-6, IDO, FGF2, IL-10, and IL-15 compared to both the control monocytes and EEMos. VEGF-A was also statistically higher in the LPS-EEMos compared to control monocytes.

Characteristic surface marker phenotypes and cytokine growth factor profiles of some embodiments of the educated macrophages described herein are outlined Example 1.

Treatment

According to the methods of the present invention, educated macrophages, educated monocytes, LPS-EVs or a combination of any two or more of the foregoing of are administered to a subject in need of thereof. Subjects in need of treatment include those already having or diagnosed with a disease or injury as described herein or those who are at risk of developing a disease or injury as described herein.

A disease or injury of the present invention may include, but is not limited to, conditions associated with radiation-induced injury and acute radiation syndrome.

With respect to radiation-induced injury, an amount of ionizing radiation exposure resulting in radiation-induced conditions appropriate for treatment or prevention according to a method provided herein is generally between minimal and maximal tolerance doses. The minimal tolerance dose ($T/D_{5/5}$) is the dose that when administered to a given patient population under a standard set of treatment conditions, results in a rate of severe complications of 5% or less within 5 years of treatment. The maximal tolerance dose ($T/D_{50/5}$) is the dose that when administered to a given patient population under a standard set of treatment conditions, results in a rate of severe complications of 50% or less within 5 years of treatment. $T/D_{5/5}$ and $T/D_{50/5}$ have been established for many conditions and are well-known (see, e.g., Rubin et al. (Eds) Radiation Biology and Radiation Pathology Syllabus, set RT 1 Radiation Oncology, Chicago, American College of Radiology, 1975). The minimal tolerance dose and maximal tolerance dose have been established with respect to therapeutic radiation treatments but are applicable as well for determining the range of radiation exposure suitable for causing the radiation-induced disorders resulting from exposure to radiation from other sources (e.g., occupational or environmental exposures).

Radiation is quantitated on the basis of the amount of radiation absorbed by the body, not based on the amount of radiation produced by the source. A rad (radiation absorbed dose) is 100 ergs of energy per gram of tissue; a gray (Gy) is 100 rad. Radiation dose can be measured by placing detectors on the body surface or by calculating the dose based on radiating phantoms that resemble human form and substance. Radiation dose has three components: total absorbed dose, number of fractions, and time. Most teletherapy radiation therapy programs are fractionated, being delivered in fractions periodically over time, typically once a day, 5 days a week, in 150-200 cGy fractions, generally applied to limited target areas of the body. The total dose delivered in radiation therapy will vary depending on the nature and severity of the condition being treated. For curative cases, the absorbed dose typically will range from 20-80Gy. For preventative cases, doses are typically around 45-60Gy and are applied in fractions of about 1.8-2Gy per day. When used for radiation therapy, ionizing radiation is usually provided over a period of time or until a particular amount of radiation exposure has been reached by the target area of the subject. Sources of ionizing radiation include electrons, X-rays, gamma rays, and atomic ions. Exposure of a subject to ionizing radiation may be due to a medical procedure including, but not limited to, radiation therapy to treat certain malignant conditions, e.g., lung or breast cancer; medical procedures such as diagnostic X-rays; or procedures involving administration of nuclear medicines. Exposure to ionizing radiation also can result from a nuclear accident or from known or suspected occupational or environmental sources, e.g., various consumer products including, but not limited to, tobacco, combustible fuels, smoke detectors, and building materials.

Radiation-induced disorders appropriate for treatment with methods of the present invention can result from exposure to ionizing radiation in the course of radiation therapy. As used herein, the term "radiation therapy" refers to the medical use of high-energy ionizing radiation to shrink tumors, to control malignant cell growth, or, where appropriate, to treat non-malignant conditions such as thyroid eye disease or pigmented villonodular synovitis. X-rays, gamma rays, and charged particles are types of radiation used for radiation therapy. The radiation may be delivered by a machine outside the body (external-beam radiation therapy, also called teletherapy), or it may come from encapsulated radioactive material implanted directly into or adjacent to tumor tissues in the body near cancer cells (internal radiation therapy, also called brachytherapy). Systemic radiation therapy uses radioactive substances, such as radioactive iodine, that travel in the blood and are targeted in some fashion to the cancer cells. Teletherapy is the most common form of radiation therapy. About half of all cancer patients receive some type of radiation therapy sometime during the course of their treatment.

Radiation-induced disorders in different tissues and organs generally follow a similar course after exposure to ionizing radiation, particularly as a consequence of radiation therapy. Depending on the dose of ionizing radiation to which the subject is exposed, the subject experiences an acute response phase that generally occurs days to weeks following exposure to ionizing radiation. The acute response phase typically involves inflammatory components, and, if low dose, in some patients, can resolve within a relatively short time or can be fatal. Depending on the dose of ionizing radiation to which the subject is exposed, the acute phase may be followed by a chronic phase, generally beginning one or more months after exposure. The chronic phase is often characterized by extensive tissue remodeling and fibrosis. Results presented herein suggest that effective treatment of the acute response may mitigate or attenuate the chronic phase. Cancers or tumors that occasionally develop, often many years later, at or near the site of radiation exposure are not intended to be included among the disorders suitable for treatment in the method of the present invention. Radiation-induced disorders, particularly those resulting from radiation therapy, are well known and have been observed in a variety of tissues and organs. The radiation-induced disorder is not the intended result of the radiation therapy but rather is an unintended, and undesirable, side effect of the exposure of various organs, tissues and body parts to the ionizing radiation used in radiation therapy. The radiation-induced disorder can be a disorder induced by irradiation of any, or multiple, body parts, organs or tissues of the subject, including but not limited to bone marrow, lung, heart, bladder, gastrointestinal tract, large intestine, small intestine, stomach, esophagus, skin, ovaries, testes, urogenital system, kidney, head, neck, pancreas, liver, brain, spinal cord, prostate, vasculature, and muscle. In various aspects the radiation-induced disorder can be, but is not limited to one or more of bone marrow failure, radiation pneumonitis, radiation enteritis, radiation enteropathy, radiation enterocolitis, radiation dermatitis, radiation-induced erythema, radiation colitis, radiation proctitis, radiation cystitis, radiation nephritis, radiation esophagitis, radiation pericarditis, radiation-induced cardiac effusion, and radiation-induced cardiac fibrosis. All of these disorders are well-known and readily identifiable by competent medical practitioners.

As used herein, the terms "treat" and "treating" refer to therapeutic measures, wherein the object is to slow down or alleviate (lessen) an undesired physiological change or pathological disorder resulting from a disease or injury as described herein. For purposes of this invention, treating the disease, condition, or injury includes, without limitation, alleviating one or more clinical indications, decreasing inflammation, reducing the severity of one or more clinical indications of the disease or injury, diminishing the extent of the condition, stabilizing the subject's disease or injury (i.e., not worsening), delay or slowing, halting, or reversing the disease or injury and bringing about partial or complete remission of the disease or injury. Treating the disease or injury also includes prolonging survival by days, weeks, months, or years as compared to prognosis if treated according to standard medical practice not incorporating treatment with educated macrophages.

Subjects in need of treatment can include those already having or diagnosed with a disease or injury as described herein as well as those prone to, likely to develop, or suspected of having a disease or injury as described herein. Pre-treating or preventing a disease or injury according to a method of the present invention includes initiating the administration of a therapeutic (e.g., human educated macrophages) at a time prior to the appearance or existence of the disease or injury, or prior to the exposure of a subject to factors known to induce the disease or injury. Pre-treating the disorder is particularly applicable to subjects at risk of having or acquiring the disease injury.

As used herein, the terms "prevent" and "preventing" refer to prophylactic or preventive measures intended to inhibit undesirable physiological changes or the development of a disorder or condition resulting in the disease or injury. In exemplary embodiments, preventing the disease or injury comprises initiating the administration of a therapeutic (e.g., educated macrophages) at a time prior to the appearance or existence of the disease or injury such that the disease or injury, or its symptoms, pathological features, consequences, or adverse effects do not occur. In such cases, a method of the invention for preventing the disease or injury comprises administering educated macrophages to a subject in need thereof prior to exposure of the subject to factors that influence the development of the disease or injury.

As used herein, the terms "subject" or "patient" are used interchangeably and can encompass any vertebrate including, without limitation, humans, mammals, reptiles, amphibians, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having a disease or injury as described herein or a pathological symptom or feature associated with a disease or injury as described herein.

In some cases, a method of treating or preventing a disease or injury as described herein comprises administering a pharmaceutical composition comprising a therapeutically effective amount of educated macrophages, educated monocytes, LPS-EVs, or a combination thereof as a therapeutic agent (i.e., for therapeutic applications). As used herein, the term "pharmaceutical composition" refers to a chemical or biological composition suitable for administration to a mammal. Examples of compositions appropriate for such therapeutic applications include preparations for parenteral, subcutaneous, transdermal, intradermal, intramuscular, intracoronarial, intramyocardial, intraperitoneal, intravenous or intraarterial (e.g., injectable), or intratracheal administration, such as sterile suspensions, emulsions, and aerosols. Intratracheal administration can involve contacting or exposing lung tissue, e.g., pulmonary alveoli, to a pharmaceutical composition comprising a therapeutically effective amount of educated macrophages or educated monocytes alone or in combination with LPS-EVs. In some cases, pharmaceutical compositions appropriate for therapeutic applications may be in admixture with one or more pharmaceutically acceptable excipients, diluents, or carriers such as sterile water, physiological saline, glucose or the like. For example, educated macrophages described herein can be administered to a subject as a pharmaceutical composition comprising a carrier solution.

Formulations may be designed or intended for oral, rectal, nasal, topical or transmucosal (including buccal, sublingual, ocular, vaginal and rectal) and parenteral (including subcutaneous, intramuscular, intravenous, intraarterial, intradermal, intraperitoneal, intrathecal, intraocular and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, educated macrophages, educated monocytes, LPS-EVs or combinations thereof may be optionally administered in combination with one or more additional active agents, including exosomes or microvesicles. Such active agents include anti-inflammatory, anti-cytokine, analgesic, antipyretic, antibiotic, immunosuppressive agents and antiviral agents, as well as growth factors and agonists, antagonists, and modulators of immunoregulatory agents (e.g., TNF-$\alpha$, IL-2, IL-4, IL-6, IL-10, IL-12, IL-13, IL-18, IFN-$\alpha$, IFN-$\gamma$, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Any suitable combination of such active agents is also contemplated. When administered in combination with one or more active agents, educated macrophages can be administered either simultaneously or sequentially with other active agents. For example, victims of acute radiation syndrome may simultaneously receive educated macrophages and a growth factor (such as G-CSF or PEG-G-CSF), a cytokine (such as IL-3, IL-11, IL-12), a population of cells (such as lymphoid or myeloid progenitors), or a small molecule radio-protective agent (such as amafostine or genistein) for a length of time or according to a dosage regimen sufficient to support recovery and to treat, alleviate, or lessen the severity of the radiation injury. In some embodiments, educated macrophages, educated monocytes, or LPS-EVs of the present invention may also be administered to a patient simultaneously with or prior to receiving a radiation treatment, such as a treatment for cancer. In some embodiments, CD14+ monocytes or macrophages are administered simultaneously with LPS-EVs to a patient.

In some embodiments, educated macrophages, educated monocytes, LPS-EVs or a combination thereof are administered to a subject in need thereof using an infusion, topical application, surgical transplantation, or implantation. In an exemplary embodiments, administration is systemic. In such cases, educated macrophages, educated monocytes, LPS-EVs or a combination thereof can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions comprising human educated macrophages, educated monocytes, LPS-EVs or combinations thereof are cryopreserved prior to administration.

Therapeutically effective amounts of educated macrophages, educated monocytes, LPS-EVs or combinations thereof are administered to a subject in need thereof. An effective dose or amount is an amount sufficient to effect a beneficial or desired clinical result. With regard to methods of the present invention, the effective dose or amount, which can be administered in one or more administrations, is the amount of human educated macrophages, educated monocytes, or LPS-EVs sufficient to elicit a therapeutic effect in a subject to whom the cells are administered. In some cases, an effective dose of educated macrophages or educated monocytes is about $1 \times 10^5$ cells/kilogram to about $10 \times 10^9$ cells/kilogram of body weight of the recipient. In some cases, an effective dose of LPS-EVs is about $1 \times 10^5$ extracellular vesicles/kilogram to about $10 \times 10^{10}$ extracellular vesicles/kilogram body weight of the recipient. Effective amounts will be affected by various factors that modify the action of the cells upon administration and the subject's biological response to the cells, e.g., severity of radiation injury, type of damaged tissue, the patient's age, sex, and diet, time of administration, and other clinical factors.

Therapeutically effective amounts for administration to a human subject can be determined in animal tests and any art-accepted methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the educated macrophages, educated monocytes, or LPS-EVs. For example, an educated macrophage dosage for a particular subject with radiation injury can be increased if the lower dose does not elicit a detectable or sufficient improvement in one or more symptoms of radiation injury. Conversely, the dosage can be decreased if the radiation injury is treated or eliminated.

In some cases, therapeutically effective amounts of educated macrophages, educated monocytes, LPS-EVs or combinations thereof can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the type of animal being treated, the duration of the treatment, and the nature of any concurrent therapy.

Following administration of educated macrophages, educated monocytes, LPS-EVs or combinations thereof to an individual subject afflicted by, prone to, or likely to develop a disease or injury described herein, a clinical symptom or feature associated with the disease or injury is observed and assessed for a positive or negative change. For example, for methods of radiation injury in a subject, positive or negative changes in the subject's infection, bleeding or anemia during or following treatment may be determined by any measure known to those of skill in the art including, without limitation, blood counts.

In any of the methods of the present invention, the donor and the recipient of the educated macrophages, educated monocytes or LPS-EVs can be a single individual, autologous, or different individuals, for example, allogeneic or xenogeneic individuals. Stromal cells and $CD14^+$ cells for use in the present invention do not need to be from the same donor, patient or source. As used herein, the term "allogeneic" refers to something that is genetically different although belonging to or obtained from the same species (e.g., allogeneic tissue grafts or organ transplants). "Xenogeneic" means the cells could be derived from a different species. In one embodiment, CD14+ cells can be collected from patients and educated to be given fresh to a person following or concurrently with radiation treatment such as a cancer treatment. In some embodiments, any allogeneic donor may act as a universal third party donor of CD14+ cells.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates the use of LPS-specific educated macrophages (LPS-EEMs) and LPS-specific monocytes (LPS-EEMos), generated from the co-culture with extracellular vesicles derived from LPS-primed MSCs, for the treatment of radiation induced injury. The embodiment described here also demonstrates the use of EVs from MSCs with and without LPS priming for the treatment of radiation induced injury.

Materials and Methods

Cell Culture—

Monocytes were isolated from human peripheral blood using magnetic bead separation methods according to manufacturers' protocols. Briefly, peripheral blood mononuclear cells were collected from the blood after mobilization from healthy donors by density gradient separation using Ficoll-Paque Plus (endotoxin tested) (GE Healthcare Bio-Sciences, Piscataway, N.J., USA) using an IRB-approved protocol. If peripheral blood has undergone apheresis designed to concentrate white cells and exclude red blood cells the density gradient separation step may be skipped, in which case the cells are diluted in buffer such as PBS, centrifuged at 300-1000×g and the pellet resuspended in ACK lysis buffer. Red blood cells were lysed by incubating cells in ACK lysis buffer for 3-5 minutes and mononuclear cells were washed with phosphate-buffered saline (PBS) (Hyclone, Logan, Utah, USA). To reduce platelet contamination, cell suspensions were centrifuged at 300-700 rpm for 10 minutes and cell pellets were re-suspended in Miltenyi separation buffer with anti-human CD14 microbeads as directed by the manufacturer (Miltenyi Biotec, Auburn, Calif., USA) and incubated for 15 minutes at 4° C. After washing to remove unbound antibody, cell separation was done using an autoMACS Pro Separator (Miltenyi Biotec). Purity of isolated CD14$^+$ cells was >95% when checked by flow cytometry. Purified CD14$^+$ monocytes were either plated into six-well cell culture plates at a concentration of 0.5-1×10$^6$ per well for characterization studies or 10$^7$ per T75 cm$^2$ filter cap cell culture flask for animal studies (Greiner Bio-One, Monroe, N.C., USA) in Iscove's modified Dulbecco's media (Gibco, Life Technologies, Grand Island, N.Y.) supplemented with 10% human serum blood type AB (Mediatech, Herndon, Va., USA or Valley Biomedical Inc, Winchester, Va., USA), 1× nonessential amino acids (Lonza, Walkersville, Md., USA), 4 mM L-glutamine (Invitrogen, Carlsbad, Calif., USA), 1 mM sodium pyruvate (Mediatech), and 4 ug/mL recombinant human insulin (Invitrogen). Cells were cultured for 7 days at 37° C. with 5% $CO_2$, without cytokines, to allow differentiation to macrophages. Attached cells were harvested using Accumax dissociation media (Innovative Cell Technologies, Inc, San Diego, Calif.).

MSCs were isolated from filters left over after bone marrow (BM) harvest from normal healthy donors using an IRB-approved protocol. Briefly, BM cells trapped in the filter were recovered by rinsing the filter with PBS and mononuclear cells were separated using Ficoll-Hypaque 1.073 (GE Healthcare Bio-Sciences). Red blood cells were lysed with 3-minute incubation in ACK lysis buffer (Lonza, Walkersville, Md., USA) and mononuclear cells were suspended in α-minimum essential medium supplemented with 10% fetal bovine serum (US origin, uncharacterized; Hyclone, Logan, Utah, USA), 1× nonessential amino acids, and 4 mM L-glutamine. Cells were cultivated in 75-cm$^2$ filter cap cell culture flasks. Attached cells (passage 0) were harvested using TrypLE™ cell dissociation enzyme (Invitrogen) and then re-plated into new flasks as described previously[20]. Passage 4-6 cells were used for characterization studies and used for isolation of extracellular vesicles (EVs). The identity of the MSCs was confirmed by flow cytometry, and their immune-modulatory properties on T-cell proliferation were confirmed by an immunopotency assay.[39,40]

Isolation and Characterization of EVs from Cells—

Cells (either MSCs or macrophages) in 75-cm$^2$ filter cap cell culture flasks were washed once with PBS, and the medium was replaced with StemPro® MSC serum-free media (SFM) CTS (A103332-01, Gibco Life Technologies,). Cells were incubated for 18-24 hours and the conditioned culture media (CM) was collected. To prime MSCs with a TLR4 ligand, lipopolysaccharide (LPS) at two different concentrations was co-cultivated with MSCs to produce LPS exosomes. SFM was supplemented with either 100 ng/ml (LPS-low) or 1.0 ug ml (LPS-high) *E. coli* LPS 0111:B4 (L4391 Sigma, St Louis, Mo., USA). EVs were isolated from un-primed MSCs (MSC-EV), LPS-primed MSCs (LPS-low or high EVs), or un-primed macrophages (macrophage-EV) by a 2-step centrifugation process as described.[41] Briefly, the CM was centrifuged using an Allegra® X-15R centrifuge (Beckman Coulter, Indianapolis Ind., USA) at 2000× g at 4° C. for 20 minutes to remove any detached cells, apoptotic bodies and cell debris. Clarified supernatant CM was centrifuged in an Optima™ L-80XP Ultracentrifuge (Beckman Coulter) at 100,000× g avg at 4° C. for 2 hours with a SW 28 rotor to pellet exosomes. The supernatant was carefully removed, and EV-containing pellets were re-suspended in PBS and pooled. We typically suspended the EV pellet at 100 ul PBS/10 ml of CM which gave EV particle concentrations of about 10$^{10}$ particles/ml (see Table 1). To visualize the EVs by transmission electron microscopy (TEM), the re-suspended EVs were layered on a 30% sucrose cushion and re-centrifuged at 100,000 gave at 4° C. for 2 hours. The upper portion of the cushion was collected and re-centrifuged. The pellet was resuspended in a small volume of PBS, whole mounted on Formvar EM grids and stained with uranyl acetate as described.[41]

EVs were characterized for protein and RNA concentration using a NanoDrop spectrophotometer (Thermo-Fisher, Waltham, Mass., USA). Mean and mode particle diameter and concentration (EV particles/ml) were assessed using an IZON qNano Nanoparticle Characterization instrument (Cambridge, Mass., USA) or a Nanosight NS300 (Malvern, UK). This analysis coupled with TEM indicated that the vast majority of EV preparation consisted of exosome-sized vesicles. Therefore, the EVs were also identified as exosomes and used synonymously.

Characterization of EV (Exosome) Surface Marker Profile by MACsplex—

The surface marker profile of EVs from two MSC isolates of both unstimulated MSC-EVs and LPS-high EVs were determined by flow cytometry using the MACSPlex Exosome Kit (Miltenyi Biotec). This kit allows the detection of 37 exosomal surface markers and two isotype markers that served as isotype controls (D1c, CD2, CD3, CD4, CD8, CD9, CD11c, CD14, CD19, CD20, CD24, CD25, CD29, CD31, CD40, CD41b, CD42a, CD44, CD45, CD49e, CD56, CD62P, CD63, CD69, CD81, CD86, CD105, CD133/1, CD142, CD146, CD209, CD326, HLA-ABC, HLA-DRDPDQ, MCSP, ROR1, SSEA-4, REA control, mIgG1 control). This assay was performed according to manufacturer's protocol. In brief, capture beads coupled with antibodies to the exosome surface markers were mixed with equal volumes of purified MSC exosomes and gently rotated in the dark at 4° C. overnight. The bead-exosome complexes were washed and then incubated for 1 hour with detection bead mixture consisting of pan-exosome markers CD9, CD63 and CD81 labeled with FITC, PE or APC. The beads were then washed and resuspended in 150 uls of MACSPlex buffer for analysis. Prior to experimentation, the system was calibrated and background settings were adjusted to unlabeled beads. The auto-sampler used 100 uls from each sample to collect beads and automated gating strategies were used to identify bead populations for each analyte. Batch analysis quantified median intensities for each bead population and analyte surface expression was calculated for each sample. Miltenyi MACSQuant Analyzer 10 for sample acquisition and MACSQuantify Software was used for data analysis. Median fluorescent values from exosomes isolated from different MSC isolates were averaged and values of 1.0 or more were considered significant compared to background.

Education of CD14$^+$ Cells by Co-Culture with EVs or MSCs—

For education of CD14$^+$ macrophages, frozen stocks of CD14$^+$ monocytes were thawed, then placed in complete macrophage media and allowed to differentiate to adherent macrophages for 5-7 days. These macrophages were then supplemented with fresh media and educated for an additional 3 days with EVs. For education of CD14+ monocytes, the frozen stocks of CD14+ monocytes were thawed, then placed in complete macrophage media and treated within 1 hour with EVs and educated for 18-24 hours. The typically EV stock concentration was $10^{10}$ particles/ml in PBS, based on EV particle concentration/ml determined using the IZON qNano Nanoparticle Characterization instrument (Cambridge, Mass., USA). The amount of the EV preparation used for education was based on dose-response studies using EVs coupled with flow-cytometry to determine changes in surface marker expression. For education, 40-60 ul of EVs were used for 6 well plates (2 mls media) or 250-300 ul of EVs in 75-cm$^2$ filter cap cell culture flasks (10 mls of media). EVs were isolated from either unstimulated MSCs (MSC-EVs), MSCs primed with LPS, (LPS-low-EVs, LPS-high-EVs) or from Day 10 macrophages to generate macrophage-EVs. Macrophage-EV preparations served as non-MSC control EVs. Educated macrophages generated by co-culture with EVs from various sources (MSC-EVs, LPS-low-EVs, LPS-high-EVs or macrophage-EVs) were designated as EEMs, LPS-low EEMs, LPS-high EEMs and macrophage-EEMs, respectively. Educated monocytes generated by co-culture with EVs from various sources (MSC-EVs or LPS-high-EVs) were designated as EEMos and LPS-high-EEMos, respectively. Direct co-culture of CD14+ macrophages with MSCs generated MSC-educated macrophages (MEMs). Day 7 macrophages were supplemented with fresh media and incubated with human BM-derived MSCs at an approximate ratio of 10:1 of macrophages:MSCs, and incubated for 3 days as previously described to generate MEMs.[20]

M1 Stimulation of Macrophages—

In contrast to treating Day 7 macrophages with EVs of MSCs, Day 7 macrophages (M0, naïve macrophages) were directly stimulated with pro-inflammatory agents to produce an M1 phenotype and serve as a comparison to the macrophages educated by EVs or MSCs. Fresh medium was added supplemented with 320 nM phorbol 12-myristate 13-acetate (PMA) for 6 hours followed by the addition of 20 ng/ml Interferon-gamma and 100 ng/ml LPS and incubated for at least 18 hours.[42] These macrophages directly stimulated with M1 factors (M1 stimulated) were used in gene expression analysis studies for comparison to control macrophages, EEMs, LPS-low-EEMs and LPS-high-EEMs. The M1 stimulated macrophages were also tested in the phagocytosis assay and the results compared to control macrophages, MEMs, EEMs, LPS-low-EEMs and LPS-high-EEMs.

Cells were harvested by removing media, washing with phosphate-buffered saline (PBS, Hyclone) then using Accumax cell dissociation enzyme (Innovative Cell Technologies, Inc, (San Diego, Calif., USA) to detach the cells from the flask followed by the use of a cell scraper. A portion of the cells was analyzed by flow cytometry and the remainder was used for animal studies.

Flow Cytometry—

Figures 3A, 3B:
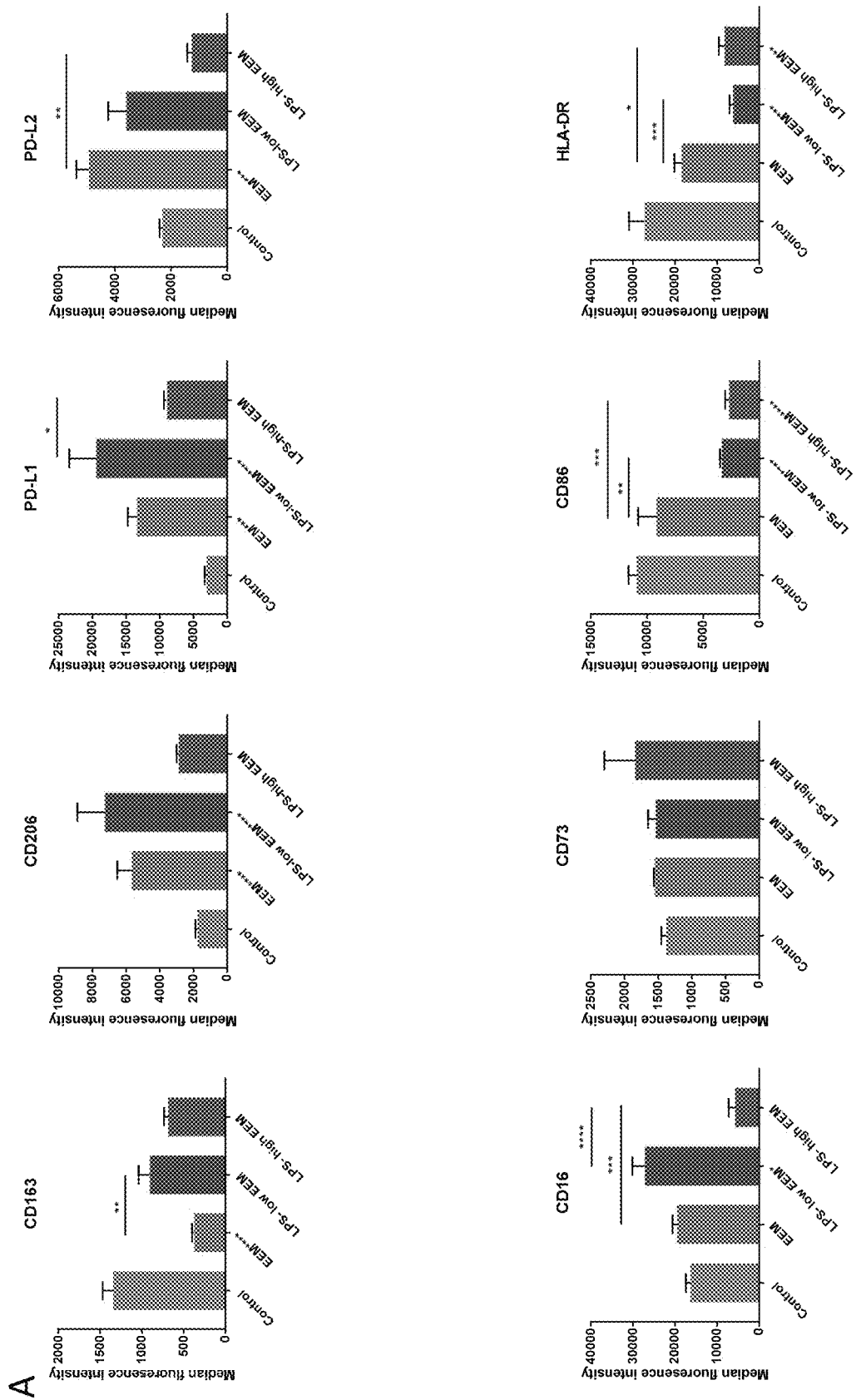
FIGS. 3A-3B show surface marker profiles of (A) mean fluorescent intensity (MFI) and (B) % cells respectively, generated by flow cytometry for control macrophages, MSC exosome educated macrophages (EEMs), LPS-low exosome educated macrophages (LPS-low-EEMs), and LPS-high exosome educated macrophages (LPS-high-EEM). The results shown represent samples from at least three human donors wherein MSCs were mobilized using G-CSF. The percent (%) of CD14$^+$ cells positive (+/−SEM) for each recited marker were measured by flow cytometry. Macrophages were cultured for 7 days (Day 7 macrophages) followed by an additional 3 days of unstimulated culture (control macrophages) or 3 days of co-culture with either exosomes from MSCs (EEM), exosomes from MSCs primed with low concentration LPS (LPS-low-EEMs), or exosomes from MSCs primed with high concentration LPS (LPS-high-EEMs). Macrophages at day 10 of culture (Day 10 macrophages) were used for flow cytometry. P values were compared to control macrophages (along the x-axis) or within groups (bars); *$p</=0.05$,  $p</=0.01$,* $p</=0.001$, **** $p</=0.0001$.
Figures 3A, 3B:
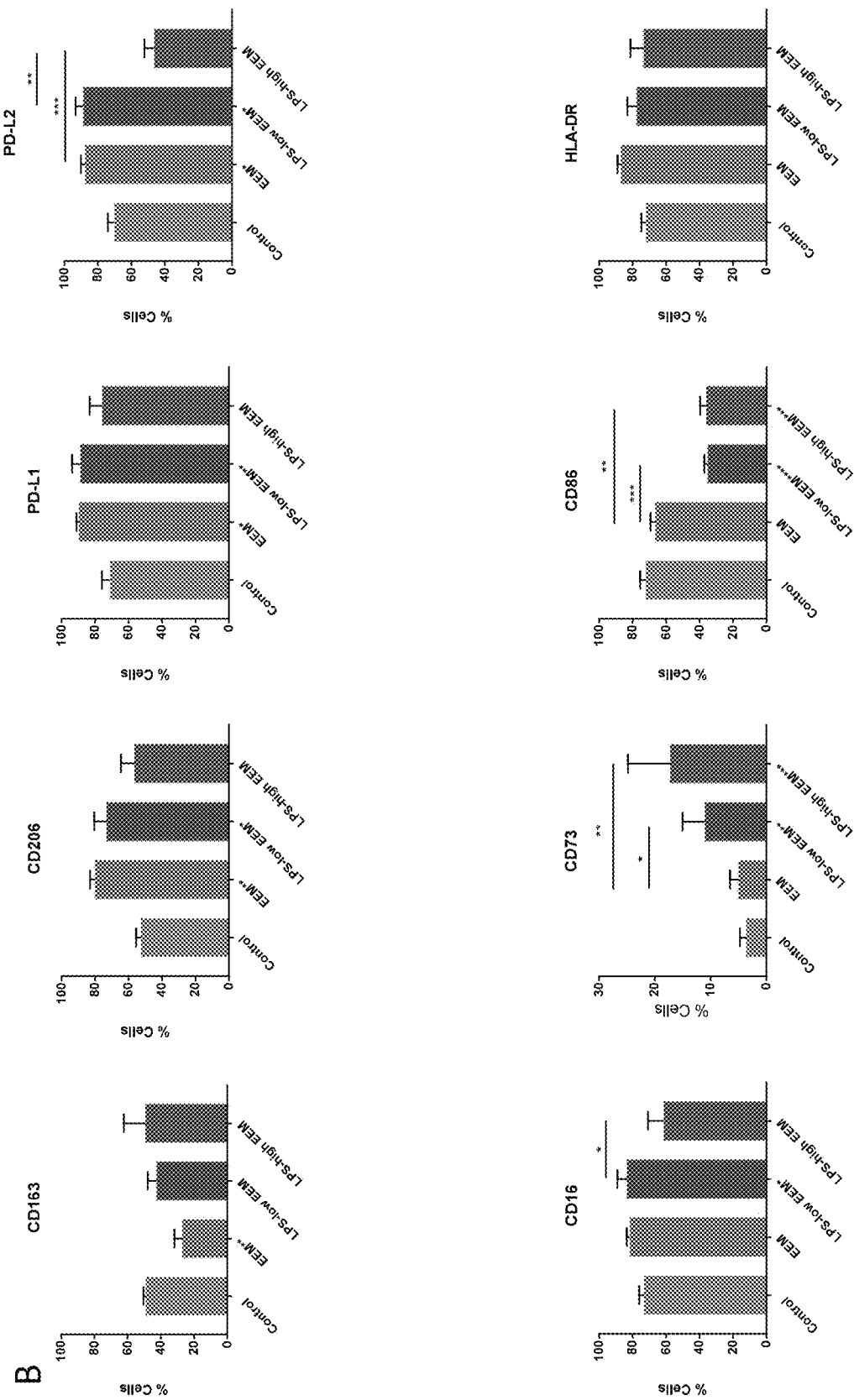
Figure 4:
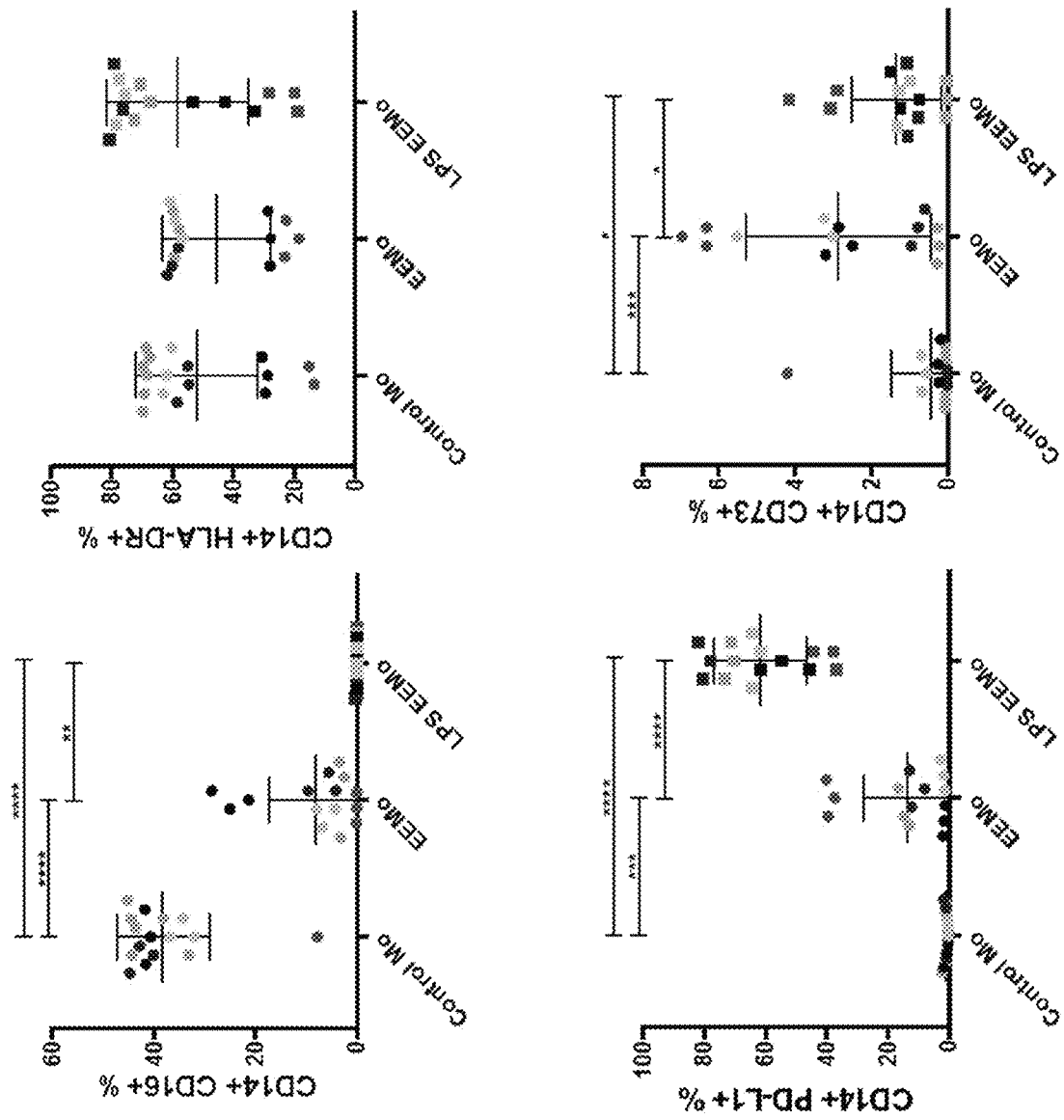
FIG. 4 shows surface marker profiles as a percentage of cells generated by flow cytometry for control monocytes, MSC exosome educated monocytes (EEMos), and LPS-high exosome educated monocytes (LPS-high-EEMos). Frozen stocks of monocytes from at least three different human donors mobilized with G-CSF were used. The monocytes were thawed and placed in culture media and either left unstimulated (control monocytes) or directly educated with exosomes for approximately 24 hours with either exosomes from MSCs (EEMo) or exosomes from MSCs primed with high concentration LPS to generate LPS-high-EEMos. P values were compared to control macrophages (along the x-axis) or within groups (bars); *$p</=0.05$,  $p</=0.01$, * $p</=0.001$, **** $p</=0.0001$.
Figure 4:
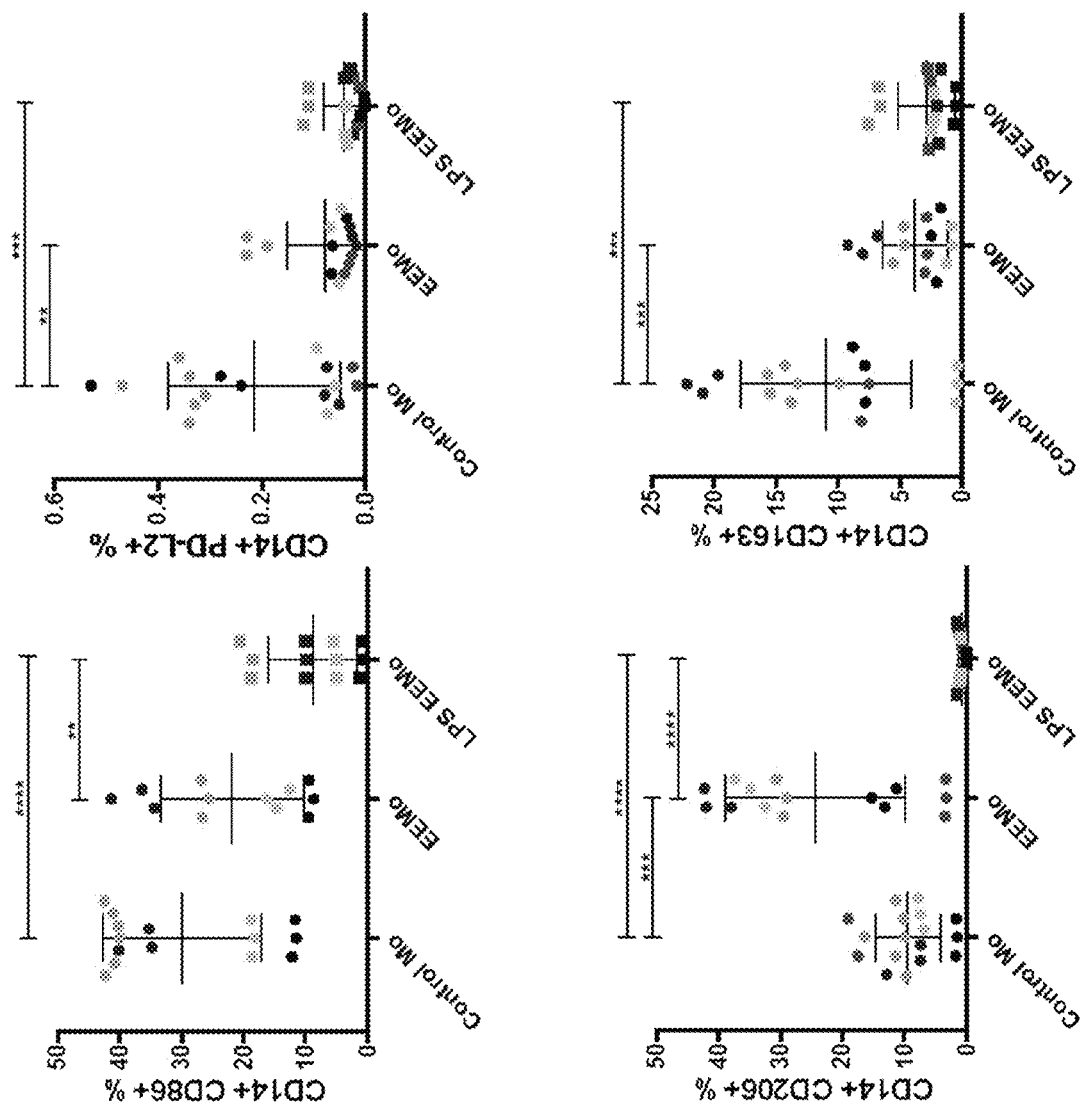

Table 3 and FIGS. 3A-3B show macrophage flow cytometry data. FIG. 4 shows monocyte flow cytometry data. Macrophages (controls (M0), MEMs, EEMs, LPS-high-EEMs, and LPS-low-EEMs) at day 10 of culture and monocytes (controls (M0), EEMos, and LPS-high-EEMos) at day 2 of culture were collected, counted and incubated with Fc block (BD Pharmingen, San Jose, Calif., USA, cat #: 564220) and stained at 4° C. for 20-30 minutes with anti-human antibodies. All antibodies were purchased from BioLegend (San Diego, Calif.) except BV510-CD73 (AD2, cat #563198) from BD Pharmingen. Panels included: MSCs, PE-Cy7-CD90 (5E10, cat #328123), macrophages, PerCP/Cy5.5-CD14 (HCD14, cat #325622), BV421-CD16 (3G8, cat #302038), M2 markers, FITC-CD163 (GHI/61, cat #333618), FITC-CD39 (A1, cat #328206), PE-CD206 (15-2, cat #321106), APC-PD-L1 (29E.2A3, cat #329708), APC-PD-L2 (24F.10C12, cat #329608), M1 markers, BV510-CD86 (IT2.2, cat #305432) and Pacific Blue-HLA-DR/MHC II (L234, cat #307633). For MEM marker analysis, macrophages (CD14+CD90−) were selectively gated using CD14 and CD90 to exclude the MSCs (CD14−CD90+). Flow cytometry data were acquired on a MACSQuant analyzer 10 (Miltenyi Biotec). Mqd files were converted to fcs files using The MACSQuantify™ Software. Listmode data were analyzed using FlowJo™ software (TreeStar).

Gene Expression Analysis—

RNA was isolated from cells using RNeasy™ micro kit (Qiagen, Valencia, Calif., USA), and the quality of isolated RNA was checked using Nanodrop 1000 (Fisher Scientific, Pittsburgh, Pa., USA). RNA was converted to cDNA using Quantitect reverse transcription kit (Qiagen). Quantitative polymerase chain reaction was performed using Power SYBR green master mix (Applied Biosystems, Foster City, Calif., USA) on StepOne Plus instrument (Applied Biosystems) using standard protocols. Verified primers for IL-10, indoleamine 2,3-dioxygenase (IDO), IL1B, IL-6, IL-8, IL-10, IL-12, IL-23, Serpine-1, TGF-B, TNF-α, Stat 1, Stat 3 and VEGF-A were purchased from Qiagen. The threshold cycle (Ct) value for each gene was normalized by the average Ct using the GAPDH housekeeping gene and using this normalization the expression values of the control macrophages or control monocytes were set at 1.0.

Phagocytic Assay—

Day 7 macrophages were either untreated, stimulated with M1 factors, or educated by co-cultivation with MSCs, or using MSC-EVs to generate EEM, LPS-low EEM or LPS-high EEM for 3 days as described above. The phagocytic assays were performed on Day 10 macrophages using the pHrodo Green E. coli Bioparticle conjugate system (cat #P35366, Invitrogen) according to manufacturer recommendations. The fluorescence of the pHrodo Green is activated within the phagosome of the cell as the pH decreases and reduces the detection of non-phagocytic binding. The pHrodo Green E. coli Bioparticle conjugate was reconstituted in PBS, diluted in media, and incubated for 1 hour at 37 C. Cells were washed with cold PBS three times to reduce non-specific attachment collected by cell scraping. Collected cells were treated with Fc Receptor blocker for 10 minutes and macrophages stained with CD14-PerCP 5.5 for 20 minutes at 4° C. CD14 positive/pHrodo Green positive cells were detected on the MACSQuant analyzer 10 (Miltenyi Biotec) and analyzed using FlowJo™ software (TreeStar).

Multiplex Cytokine ELISA Assay—

Day 7 macrophages ($10^6$/well) grown in 6-well plates were either untreated (control), stimulated with M1 factors or educated for 3 days in culture media with MSC-EVs to generate EEMs, LPS-low EEMs, and LPS-high EEMs as described in above. The cells were washed with PBS, medium was replaced and after 24 hours cells were recovered, centrifuged at 300×g for 10 minutes to remove cell debris and assayed for cytokines and other factors using a Milliplex MAP cytokine/chemokine multiplex magnetic bead panel (HCYTOMAG-60K, Millipore, Burlington Mass.). Twenty-five ul of culture media from three sets of macrophage isolates, each set performed in duplicate wells were assayed for secreted products as directed by the manufacturer and detected on a Luminex xMAP platform. The analytes assayed were EGF, FGF-2, EOTAXIN, TGF-a, G-CSF, FLT-3L, GM-CSF, FRACTALKINE, INFa2, IFNg, GRO, IL-10, MCP-3, IL-12p40, MDC, IL-12p70, IL-13, PDGF-BB, IL-15, sCD40L IL-17, IL-1ra, IL-1a, IL-9, IL-1b, IL-2, IL-4, IL-5, IL-6, IL-7, IL-8, IP-10, MCP-1, MIP-1a, MIP-1b, RANTES, TNFa, TNFb and VEGF.

Immunopotency Assay. The immunopotency assay (IPA) was used to determine if the co-culture of T-cells with either MSCs, macrophages, EEMs or LPS-EEMs affects proliferation of CD4+T-helper and/or CD8+T-cytotoxic cells after stimulation with anti-CD3 and anti-CD28. Peripheral blood mononuclear cells (PBMCs), the source of the CD4+ and CD8+ cells were isolated from leukapheresis products collected from different normal healthy donors and were purchased from SeraCare Life Sciences (Milford, Mass.). After Ficoll separation, between 4 and $5 \times 10^9$ PBMCs were recovered then cryopreserved at $1 \times 10^7$ cells/vial using 90% FBS (Atlanta Biologics, Atlanta, Ga.) and 10% DMSO (Sigma-Aldrich, St. Louis, Mo.) and stored in LN2 before use in this assay. The test cells used in co-cultivation were isolated as described above and consisted of either: MSCs, macrophages, EEMs or LPS-low EEMs. They were all prepared in IPA medium consisting of RPMI-1640 containing 10% heat inactivated FBS, 1× non-essential amino acids (NEAA) (Mediatech, Inc., Manassas, Va.), 1× Glutamine (Mediatech, Inc.), 1× Na Pyruvate (Sigma-Aldrich), and 1×HEPES buffer (Sigma-Aldrich, St. Louis, Mo.). This assay was performed in a 48 well tissue culture plate with a total IPA medium volume of 400 ul per well. Preparation of test cells for this assay included wash, and re-suspension at $4 \times 10^6$/mL.

For a 1:1 (PBMC:test cell) ratio, $4 \times 10^5$ MSCs (100 ul) were plated and then titrated further to $2 \times 10^4$ to achieve a 1:0.05 (PBMC:test cell) ratio. The stimulated PBMC to test cell ratios that were evaluated in this assay include 1:1, 1:0.5, 1:0.1, and 1:0.05. The volume of test cells was held constant at 200 ul/well using IPA medium. After plating, the test cells were allowed to settle and adhere to the plastic for 2 hours at 37° C. To measure proliferation, PBMCs were labeled with carboxyfluorescein succinate-ester (CFSE) at a final concentration of 1 uM for 10 minutes, at 37° C. in the dark, mixing at the 5 minute time point to ensure homogeneous labeling. An equal volume of cold FBS was added for 1 minute to stop the CFSE labeling reaction. PBMCs were then washed twice with IPA medium as defined above before reconstitution at $4 \times 10^6$/mL. One hundred microliters of CFSE-labeled PBMCs was added to each well containing the various ratios of test cells. Anti-CD3 and anti-CD28 antibodies (clones UCHT1 and 37407, respectively) (R&D Systems, Inc., Minneapolis, Minn.) also prepared in the IPA medium were used to stimulate the proliferation of CD4+ helper T-cells and CD8+ cytotoxic T-cells. A 100 ul mixture of 4× concentrated anti-huCD3 and anti-huCD28 antibodies (10 ug/mL and 2 ug/mL, respectively) was added to each well except for the 1:0.05 (PBMC:test cell) non-stimulated control which received 100 ul of IPA medium instead (negative control). Cells were cultured for 4 days at 37° C. before the CD4+ T cells were analyzed for proliferation using standard flow cytometry methodology. Anti-huCD4 APC or anti-huCD8 APC (R&D Systems, Inc.) was used to gate the CD4+T and CD8+ T cells. All IPA analyses were performed using an Accuri C6 flow cytometer (BD Biosciences, Inc., San Jose, Calif.) and the associated C6 Plus software was used for the CFSE analysis.

Mice—

Male and Female NOD.Cg-Prkdc$^{scid}$ Il2$^{tm1Wjl/SzJ}$ (NSG) mice were purchased from The Jackson Laboratory (Bar Harbor, Me.) and used at 8-16 weeks of age. All animals were bred and housed in a pathogen-free facility throughout the study. The Animal Care and Use Committee at the University of Wisconsin approved all experimental protocols.

In Vivo Lethal Radiation Injury Model—

On day 0, approximately equal numbers of NSG male and female mice received 4Gy lethal total body irradiation using an X-RAD 320 X-ray irradiator (Precision X-Ray, North Branford, Conn., USA) to induce consistent lethality within a 2 week time frame. Four hours after radiation injury, mice were treated intravenously in the tail vein with either 100 ul of PBS (control), $1 \times 10^6$ human macrophages, $1 \times 10^6$ human bone marrow-derived MSCs (passage 4-6), $1 \times 10^6$ EEMs, $1 \times 10^6$ LPS-low-EEMs, $1 \times 10^6$ LPS-high-EEMs, $1 \times 10^7$ monocytes (Mo), or $1 \times 10^7$ LPS-high-EEMos. For EV treatment studies, mice were treated immediately post radiation challenge with varying dosages ($2-5 \times 10^{10}$ of MSC-EVs or LPS-EVs. The mice were monitored at least 3 times a week for survival and weight change. Clinical scores were also determined based on a modified clinical scoring system for GVHD. Cumulative scores of percent weight loss, posture, activity, and fur texture (scored from 0-2 for each criteria), were recorded as previously described[43]. On day 4 and day 32 post-challenge, blood from surviving mice was collected in a microtainer tube $K_2$ EDTA (Becton Dickenson, Franklin Lakes, N.J.) or equivalent from a tail vein nick and the hematology of the whole blood was assayed on a Hemavet™ 950FS analyzer (Drew Scientific Inc., Miami Lakes, Fla., USA).

Diagnostic Necropsy and Histologic Preparation—

Gross necropsy of organ systems consisting determination of both organ weight and organ weight as function of percent body weight (% BW) as well as the external examination of the integument, cardiovascular, respiratory, digestive, lympho-hematopoietic, uro-genital, endocrine, central nervous system and musculoskeletal. Gross necropsy was performed on the following groups: Un-irradiated mice, mice post radiation challenge on day 9 (PBS treated and LPS-high EEM treated), day 31 (LPS-high EEM treated), and day 52-53 (moribund LPS-high EEM treated). At strategic time points post-radiation challenge, spleens were harvested, weighed and from either moribund control mice or treated mice and compared to the weight of normal un-irradiated healthy controls. Histology focused on the preparations of slides from sections of spleen and bone marrow from the femur, vertebrae and ileum. Tissues were fixed in 10% neutral buffered formalin and processed on a Sakura Tissue-Tek VIP 6 processor and embedded on a Sakura Tissue-Tek TEC embedding station. Slides were cut on a Leitz 2235 microtome at 5-6 microns and stained with H&E using a Sakura Tissue-Tek DRS automatic stainer and manually cover slipped. Tissues were visualized using a Nikon Eclipse 50 I microscope at multiple magnifications using Nikon objectives; 4×/0.2-Plan Apo, 10×/0.45 Plan Apo, 20×/0.75 Plan Apo, 40×/0.95 Plan Apo. Photographs were taken using a SPOT model 10.2 camera aided with SPOT acquisition software for MAC 5.2.

Statistical Analysis—

Statistics were performed using GraphPad Prism version 7.0 (GraphPad Software, San Diego, Calif.). Data were reported as mean±SEM. For analysis of three or more groups, the analysis of variance (ANOVA) test was performed with the Kruskal-Wallis and Dunn's multiple comparisons post-test. Principal component analysis and t-tests comparing gene expression between groups were performed on Microsoft Excel. Multiple hypotheses testing correction was done using the Benjamini Hochberg false discovery rate (FDR) procedure. A p-value less than 0.05 was considered statistically significant.

Results

Characterization of the Extracellular Vesicles (EVs)—

Electron-microscopic observation (FIG. 1a,b) indicate EVs from the MSCs have the typical appearance of an EV; circular shape with convex center and the majority of EV preparation consisted of exosome-sized vesicles (<200 nm). EVs are composed of exosomes, generally 50-250 nm in size, and larger micro-vesicles typically greater than 500 nm. Quantifying the EVs using either a resistive pulse sensing instrument (qNano Nanoparticle instrument, FIG. 1c.) or a visual nanoparticle tracking analysis (Nanosight NS300, FIG. 1d.) yielded similar profiles in terms of mean particle sizes, range and particle density. The analysis of EVs preps from multiple MSC isolates using the qNano instrument also indicated that the mean particles size (139 nm+/−15) and mode particle size (97 nm+/−9) were consistent with exosome-sized vesicles (Table 1). There were slight differences detected in mean and mode sizes between MSC isolates ranging from 84 to 181 nm, although mean particle concentrations were very similar at $1.5 \times 10^{11}$ particles/ml and ranged from 0.76 to $2.0 \times 10^{11}$ particles/ml. Unlike a previous report[37], we did not detect a significant increase in the particle concentration using the qNano instrument after priming of MSCs with LPS at either low or high dosages. Macrophages also produced EVs that were mostly in the exosomes size range but interestingly secreted about 10-fold more EVs than MSCs based on cell number.

MACsplex Analysis of Exosomal Surface Markers

Comparison of exosome surface markers from exosomes from either unstimulated MSC or MSCs primed with high concentration LPS. The mean of the most intense exosome surface markers from two different human BM MSC isolates is shown in FIG. 2. Of the 37 markers analyzed by MACSPlex, both MSC and LPS-high exosomes showed the strongest surface marker profile for eight markers; (listed from highest to lowest) CD44, CD63, CD81, CD146, CD29, CD105, MCSP and CD9. CD81, CD63 and CD9 are members of a family of tetraspanins, known to on the surface of exosomes and complex with integrins for signal transduction.[5] CD44 is a receptor for hyaluronic acid and can also interact with other ligands, such as collagens, osteopontin, and matrix metalloproteinases (MMPs).[6][7] CD105 has been found to be an auxiliary receptor for the TGF-beta receptor complex and is involved in modulating a response to the binding of TGF-beta (1 and 3).[8] CD29 is Integrin beta-1 which associates with integrins alpha 1 and 2 to form integrin complexes that form collagen receptors and function in a variety of processes such as tissue repair.[9] MCSP, is a cell surface proteoglycan thought be functionally important in epidermal stem cell clustering. (Legg, J. 2003)

Comparison of Gene Expression by qPCR of Educated Macrophages Vs Direct M1 Stimulation We next examined gene expression levels that were previously found to be changed in MEMs when co-cultivated with MSCs from different tissues.[44] Gene expression in EEMs, LPS-low-EEMs and LPS-high-EEMs were compared to expression levels in control macrophages normalized to a value of 1. In general, macrophages educated with

TABLE 1

This table characterizes the size and concentration of the exosomes isolated from different sources of cells (BM-MSC, macrophages) using the qNano Nanoparticle instrument. The size (mean/mode) and particle concentrations (/ml) overall are very consistent between batch (culture round, first, third), cell type, or whether the MSCs were primed with high or low concentrations of LPS. EVs isolated and analyzed using qNano Nanoparticle instrument from 4 different BM-MSCs isolates, (15PH05, 15PH06, 15PH07 and 15PH09), primed with LPS-high or low, at different passages (P3-P6), or from different rounds of CM harvest (first or third) all generated preparations with similar yields of particle concentration/ml. In addition, the particle number produced based on cell number ($10^6$ cells) was also similar. However, macrophages, which are cultivated at about 10-fold lower cell densities were found to produce more exosomes based on cell concentration.

| Cell type | Isolate | Culture round | Mean particle size (nm) | Mode particle size (nm) | Particle concentration/ml | Approx Particle concentration/$10^6$ cells |
|---|---|---|---|---|---|---|
| BM MSC | 15PH05 P3 | first | 92 | 64 | $7.6 \times 10^{10}$ | $8.4 \times 10^9$ |
| BM MSC | 15PH06 P4 | first | 162 | 108 | $1.6 \times 10^{11}$ | $1.7 \times 10^{10}$ |
| BM MSC | 15PH07 P4 | first | 85 | 84 | $1.8 \times 10^{11}$ | $2.0 \times 10^{10}$ |
| BM MSC | 15PH09 P3 | first | 86 | 61 | $2.0 \times 10^{11}$ | $2.2 \times 10^{10}$ |
| BM MSC | 15PH05 P4 | first | 169 | 114 | $1.3 \times 10^{11}$ | $1.4 \times 10^{10}$ |
| BM MSC | 15PH05 P4 | third | 175 | 114 | $1.4 \times 10^{11}$ | $1.5 \times 10^{10}$ |
| BM MSC | 15PH05 P4 (LPS-low) | third | 181 | 131 | $1.2 \times 10^{11}$ | $1.3 \times 10^{10}$ |
| BM MSC | 15PH05 P6 (LPS-high) | first | 167 | 104 | $1.8 \times 10^{11}$ | $2.0 \times 10^{10}$ |
| BM MSC | 15PH05 P8 (LPS-high) | third | 177 | 104 | $7.6 \times 10^{10}$ | $8.4 \times 10^9$ |
| Macrophage | 4/09/16 | first | 159 | 116 | $6.5 \times 10^{11}$ | $3.3 \times 10^{12}$ | the exosomes were more immunosuppressive and anti-inflammatory. There were significant increases in expression of IDO, a known immunosuppressive modulator, in the EEMs, along with significant increases in IL-6, IL-1B and IL-8. Very large increases in IDO were seen in both the LPS-low and LPS-high EEMs; increases being significant in the latter (Table 2). Increases in immune modulating and hematopoietic system supportive IL-6 in the EEMs compared to controls, were much higher in both of the LPS-EEMs. However, significant increases in anti-inflammatory IL-10 not seen in the EEMs were seen in the LPS-EEMs. There were also significant decreases in expression of pro-inflammatory IL-12 in the LPS-EEMs, however there were significant increases in other pro-inflammatory cytokines such as TNF-α in LPS-low-EEMs and IL-8 in LPS-high-EEMs. There was also significant increase in the VEGF-A, involved in angiogenesis in the LPS-high-EEMs. STAT1, involved in cytokine signal transduction, was higher in both LPS-EEM populations. The M1 stimulated macrophages were more pro-inflammatory in nature, as expected, and generally produced an M1 profile; anti-inflammatory IL-10 was significantly lower, along with VEGF-A, STAT1 and STAT3 and pro-inflammatory TNF-α and IL-23 were significantly higher.

As in Table 2, LPS-EEMs expressed a unique anti-inflammatory/immunosuppressive profile compared to control macrophages by RT-PCR. EEMs showed significant increases in mRNA expression of IDO, IL-6, IL-1B and IL-8 expression. LPS-EEMs showed significant increases in expression of several anti-inflammatory cytokines (IL-6, IL-10), as well as IL-8, IDO, STAT 1 and VEGF-A. There was also a significant decrease in expression of the pro-inflammatory IL-12. After M1 stimulation, macrophages produced statistical increases in pro-inflammatory TNF-α and IL-23, and an accompanying decrease in IL-10. P values compared to control; *p<$/$=0.05, p<$/$=0.005, *p<$/$=0.0005.

TABLE 2

| Gene | EEM | LPS-low EEM | LPS-high EEM | M1 stimulation |
|---|---|---|---|---|
| IL-10 | 1.3 | 2.5* | 2.3** | 0.17*** |
| IDO | 26.6*** | 12991 | 12747* | 62.3 |
| IL-6 | 3.3* | 331* | 593 | 171 |
| IL-12 | 1.4 | 0.4** | 0.5** | 1.1 |
| Serpine-1 | 1.6 | 2.2 | 1.4 | 19.4* |
| TGF-B | 1.0 | 0.6 | 1.5 | 0.9 |
| VEGF-A | 1.3 | 10.7 | 5.1*** | 0.6* |
| Stat3 | 1.0 | 1.8* | 2.9 | 0.7* |
| Stat1 | 0.8 | 2.8** | 2.7* | 0.6* |
| TNF | 1.5 | 3.9*** | 5.7 | 4.1** |

TABLE 2-continued

| Gene | EEM | LPS-low EEM | LPS-high EEM | M1 stimulation |
|---|---|---|---|---|
| IL-23 | 1.3 | 2.6 | 7.0 | 2.9* |
| IL-1B | 2.7* | 43.9 | 45.6 | 35.5 |
| IL-8 | 9.3** | 477 | 520.3* | 542 |

Both MEM and EEMs had a distinct surface marker profile by flow cytometry. The percentage of CD14+ cells with indicated surface markers and mean fluorescent intensity (MFI) of control macrophages compared to MEMs, EEMs and macrophages educated from exosomes from macrophages (macro-EEMs) by flow cytometry is shown in FIGS. 3A-3B. The % cells in the MEMs was significantly higher than the control macrophages for CD206, PD-L1 (considered M2 markers), CD16, CD73 and the M1 marker, HLA-DR. In addition the MFIs for MEMs were higher for CD206, CD16 and CD73.[27]. EEMs were found to express even higher levels of both % cells and MFI for CD206 and PD-L1, and unlike MEMs which are lower for CD163 but higher for PDL-2. In contrast to MEMs, CD16 and HLA-DR levels in EEMs were not significantly different compared to controls. The M1 marker CD86 in either the MEMs or EEMs was not different from controls. Overall, both groups showed increased anti-inflammatory M2 surface markers, but each had a distinct marker profile. The nine surface marker profile of the Macrophage-EEMs was not significantly different than controls, except for PD-L1 (% cells).

As shown in Table 3, EEMs express a unique surface marker profile by flow cytometry compared to control macrophages by flow cytometry. Day 7 macrophages isolated from at least three different human donors were either unstimulated (Control) or stimulated for 3 days by co-culture with MSCs (MEM) or with exosomes from MSCs (EEM) or from macrophages (Macro-EEM). The ratio of CD14+ cells positive for each marker was designated as percent (%) and the cell staining intensity of CD14+ cells for each marker was designated as median fluorescence intensity (MFI). The percentage of cells positive for CD206, PD-L1, CD16, CD73 and HLA-DR was significantly higher in the MEMs compared to control macrophages. The MFI for CD206, CD16, and CD73 was also higher in the MEMs. In the EEMs, both the percentage of positive cells and the MFI for CD206, PD-L1 and PD-L2 were also higher compared to controls. In contrast, both the percentage of positive cells and the MFI for CD163 were lower in the EEMs compared to controls or MEMs. When comparing control macrophages to macrophages treated with their own exosomes (Macro-EEMs) there was little or no difference in both the percentage of positive cells and the MFI, except for % PD-L1. P values were compared to control; *p<$/$=0.05,  p<$/$=0.005, * p<$/$=0.0005.

TABLE 3

| Group | CD163 | CD206 | PD-L1 | PD-L2 | CD16 | CD39 | CD73 | CD86 | HLA-DR |
|---|---|---|---|---|---|---|---|---|---|
| Control | 47.4% | 53.8% | 64.1% | 63.5% | 75.7% | 50.3% | 1.9% | 75.2% | 72.9% |
|  | (1171) | (1618) | (3518) | (2267) | (17478) | (1662) | (1332) | (12282) | (20791) |
| MEM | 70.2% | 86.2%** | 80.7%* | 81.7% | 94.4%* | 55.3% | 13.3%* | 87.0% | 91.2%* |
|  | (1491) | (3802)* | (2436) | (1916) | (32904)** | (1056) | (2054)* | (10973) | (13452) |
| EEM | 23.0%* | 80.3%* | 89.7%** | 87.2%** | 80.4% | 66.1% | 2.1% | 69.4 | 85.3% |
|  | (402)* | (6071)*** | (12252)** | (4608)** | (19925) | (2701) | (1542) | (12033) | (17201) |
| Macro-EEM | 50.4% | 66.2% | 87.3%* | 81% | 82.5% | 59.9% | 1.0% | 80.2 | 72.2% |
|  | (1662) | (3424) | (4980) | (3160) | (18715) | (2872) | (1334) | (9943) | (24419) |

LPS-High-EEMs Showed a High CD73 Marker and Low M1 Marker Surface Profile by Flow Cytometry.

Both the LPS-low EEMs and LPS-high EEMs each have a distinctive surface phenotype when comparing both the % CD14+ cells with each surface marker and their MFI to each other or when compared to control macrophages or the EEMs. Surface markers of control macrophages, EEMs, LPS-low-EEM, and LPS-high-EEMs for % CD14+ cells and MFI are shown in FIGS. 3A-3B. Compared to control macrophages, the LPS-low-EEM showed a hybrid M2-like surface marker profile for % cells and MFI that were similar to both EEMs and MEMs. As seen for the EEMs, LPS-low-EEMs showed significantly elevated % cells for CD206, PD-L1 and PD-L2 compared to controls (FIG. 3A). As with the MEMs, the LPS-low-EEMs had higher CD16 and CD73% cells compared to controls. MFI (FIG. 3B) of the LPS-low-EEMs showed a higher CD206, PD-L1 and CD16 compared to controls. However, LPS-high-EEMs showed a distinct surface profile compared to the LPS-low-EEMs. The levels of many M2 markers (CD206, PD-L1 and PD-L2) decreased in the LPS-high-EEMs compared to control macrophage levels. Furthermore, the LPS-high-EEMs compared to the LPS-low-EEMs expressed an even higher percent of cells with CD73, an ecto-nucleotidase which converts AMP to adenosine and thought to be involved in immune-suppression. Importantly, lower levels of CD16, considered an inflammatory CD14+ cell marker involved in antibody dependent cell mediated cytotoxicity, was found in the LPS-high-EEMs. As found for the LPS-low-EEMs, there was a significant decrease in the M1 markers, CD86 and HLA-DR in the LPS-high-EEMs. Overall, the distinguishing marker profile of the LPS-high EEM compared to control expressed a unique surface profile which would be summarized as CD73-high, CD16-low, CD86-low and HLA-DR-low as shown in FIGS. 3A-3B.

As depicted in FIGS. 3A-3B, LPS-EEMs express high levels of CD73 (ecto-5-nucleotidase) but low levels of M1 markers CD86 and HLA-DR by flow cytometry. Day 7 macrophages isolated from at least three different human donors were either unstimulated (Control) or stimulated for 3 days with exosomes from MSCs (EEM) or from MSCs primed with low (LPS-low EEM) or high (LPS-high EEM) LPS. The ratio of CD14+ cells positive for each marker was designated as percent (%) and the cell staining intensity of CD14+ cells for each marker was designated as median fluorescence intensity (MFI). The LPS-low EEMs showed a higher percentage of cells positive for CD206, PD-L1, PD-L2, CD16 and CD73 but much lower levels of the M1 markers, CD86 and HLA-DR compared to control macrophages. In contrast to the LPS-low EEMs, the LPS-high EEMs marker profiles for CD206, PD-L1, PD-L2 and CD16 were low but there were significantly more CD73 expressing cells in the LPS-high EEMs coupled with very low levels for CD86 and HLA-DR.

LPS-High-EEMos Showed a High PD-L1, CD73 Marker and Low M1 Marker Surface Profile by Flow Cytometry.

The LPS-high-EEMos had a distinctive surface marker phenotype, as determined by flow cytometry, when compared to controls monocytes or to EEMos. As shown in FIG. 4, the flow profile (percent cells) of the LPS-high-EEMos showed high PD-L1 and CD73 expression but low CD206, CD16, PD-L2, CD163 and CD86 compared to control monocytes. When the LPS-high-EEMos were compared to the EEMos, their profile was more similar than controls but the levels in LPS-high-EEMos were significantly lower for CD16, CD73, CD86 and CD206 but higher for PDL-1.

Comparison of Gene Expression by qPCR of EEMos

Figures 5A, 5B, 5C:
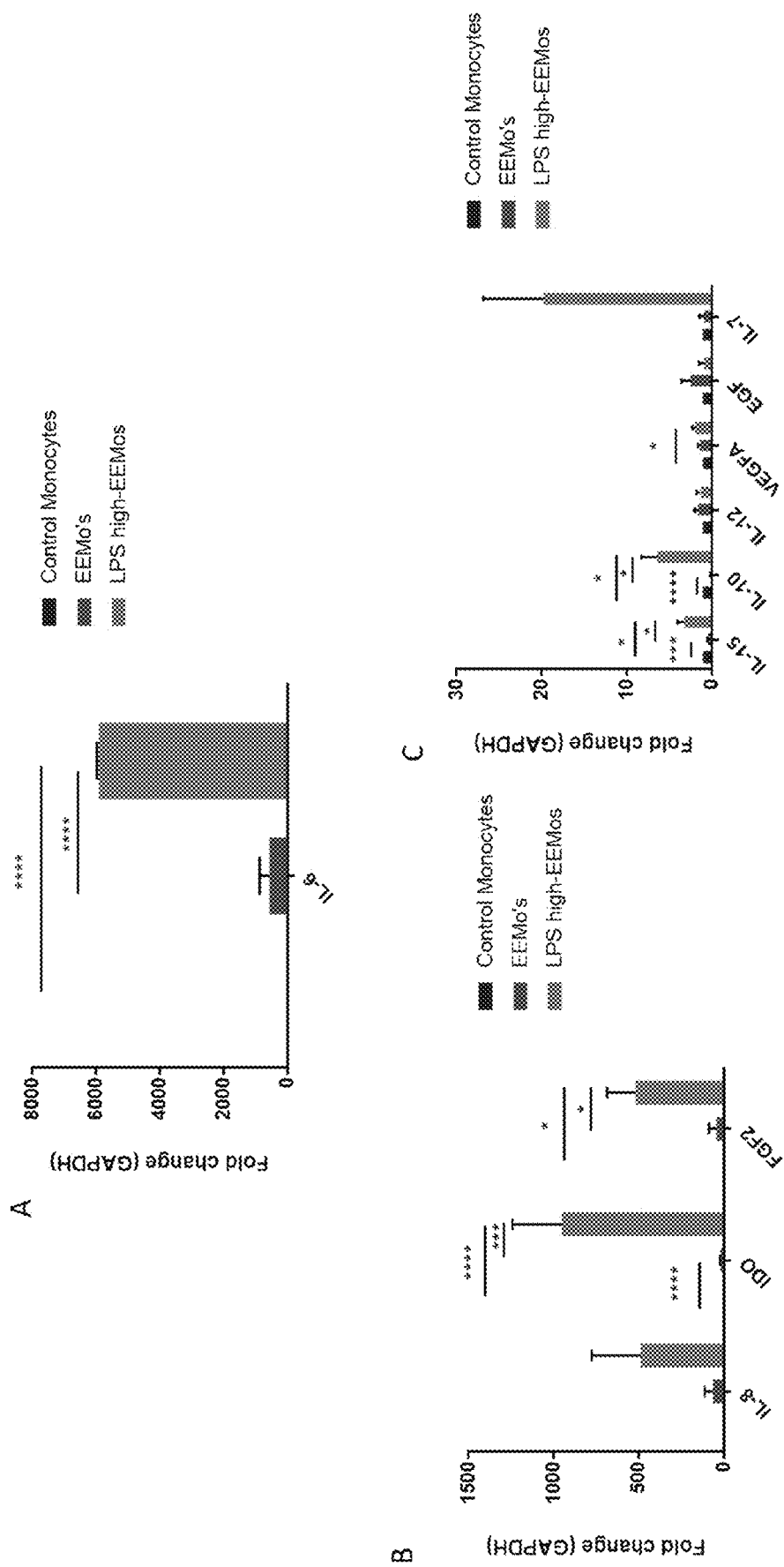
FIGS. 5A-5C show gene expression by RT-PCR of monocytes from multiple human isolates which were either unstimulated (control) or educated for 24 hours with exosomes from MSCs to produce EEMos and LP-high-EEMos as described in Example 1. After education, cells were collected, RNA isolated and analyzed by RT-PCR for gene expression. The fold change of gene expression is normalized to the expression level of the GAPDH house-keeping gene in unstimulated control macrophages and set at a value of 1.0.

As shown in FIGS. 5A-5C, gene expression studies by qPCR of the LPS-EEMos, when compared to both the control monocytes (value of 1.00) and EEMos, showed statistical increases in IL-6, IDO, FGF2, IL-10, and IL-15. IL-8 was high in the LPS-EEMos but not statistically significant. VEGF-A expression was statistically higher in the LPS-EEMos compared to only the control monocytes. The EEMos showed statically higher expression in IDO, but lower expression of IL-15 and IL-10 compared to controls. High expression of IL-6, IL-10 and IDO were common in both educated macrophages and monocytes.

Anti-Inflammatory Immunosuppressive and Reparative Secretion Profile in the LPS-High EEMs by Multiplex ELISA The multiplex ELISA data indicated that macrophages educated with LPS-EVs produced from MSCs activated a large cascade of many cytokines, chemokines and growth factors that were secreted at significantly higher levels than control macrophages. Moreover, many were significantly higher that the unprimed EVs used to produce the EEMs.

As shown in Table 4, LPS-EEMs secrete high levels of anti-inflammatory, growth and chemotactic factors by ELISA compared to control macrophages. Day 7 macrophages were either unstimulated (Control) or stimulated for 3 days MSC-EVs to produce (EEM) or from MSC-EVs primed with low or high LPS (LPS-low EEM) (LPS-high EEM). The EEMs secreted significant levels of Eotaxin, G-GSF, FRACTALKINE, INFa2, GRO, IL-7, IL-8, TNF-α, and VEGF compared to control macrophages. While not statistical due to variability between macrophage isolates, high levels of secreted IL-6 were also detected in the EEMs. When comparing EEMs to the LPS-low EEM and LPS-high EEMs, there was a significant increase in secretion of many anti-inflammatory cytokines such as IL-4, IL-10, IL-13, including very high, although non-statistical, increases in immune-modulating IL-6. In addition, there were significant increases in chemotactic/chemoattractant chemokines; EOTAXIN, IL-8, GRO and IP-10, growth factors such as EGF, FGF-2, and VEGF, in the cell proliferative cytokine, IL-15, soluble CD40 ligand (sCD40L) a marker of platelet activation, hematopoietic growth factors; IL-7, platelet-derived growth factor, two B unity type (PDGF-BB) and FMS-like tyrosine kinase type 3 ligand (FLT-3L) involved in activating hematopoietic progenitors and hematopoietic cell mobilization factors, G-CSF and GM-CSF and immunomodulatory cytokines; INFa2, IFNg, IL-17, IL-1a, IL-9 and IL-5. Both the LPS-low and -high EEM also secreted higher levels of pro-inflammatory cytokines such as TNF-α, IFNg, IL-1b and IL-12p40 and p70. When comparing any statistical differences in secreted factors between LPS-low EEMs to LPS-high EEMs, FLT-3L and IL-15, both involved in cell activation and proliferation, were found to be significantly higher in the latter.

TABLE 4

Symbol (*) indicated significance versus control, (#) indicates significance versus EEMs, and ($) indicates significant versus of LPS-high EEMs compared to LPS-low EEMs. The number of symbols (*, #, $) indicates the increased level of significance, one symbol $p \leq 0.05$, two symbols $p \leq 0.01$, three symbols $p \leq 0.001$, 4 symbols $p \leq 0.0001$

| Analyte (pg/ml) | Control | EEMs | LPS-low-EEMs | LPS-high-EEMs |
|---|---|---|---|---|
| EGF | 0.6 | 0.0 | 4.7***### | 5.6****#### |
| FGF-2 | 17.6 | 21.4 | 34.4***### | 35.7****### |
| EOTAXIN | 3.4 | 5.6* | 8.7***# | 9.6***## |

TABLE 4-continued

Symbol (*) indicated significance versus control, (#) indicates significance versus EEMs, and ($) indicates significant versus of LPS-high EEMs compared to LPS-low EEMs. The number of symbols (*, #, $) indicates the increased level of significance, one symbol p </= 0.05, two symbols p </= 0.01, three symbols p </= 0.001, 4 symbols p </= 0.0001

| Analyte (pg/ml) | Control | EEMs | LPS-low-EEMs | LPS-high-EEMs |
|---|---|---|---|---|
| TGF-a | 2.7 | 3.3 | 6.2*# | 6.4*# |
| G-CSG | 26.5 | 62.4* | 223.9*# | 286.0*## |
| FLT-3L | 8.7 | 9.4 | 14.4*# | 18.9***###$ |
| GM-CSF | 9.0 | 12.0 | 20.2**# | 24.1**## |
| FRACTALKINE | 20.1 | 30.2* | 50.2**# | 59.0***## |
| INFa2 | 15.3 | 21.8* | 38.5***## | 41.1***### |
| IFNg | 5.8 | 7.6 | 12.1* | 14.3**## |
| GRO | 307.1 | 1249.6* | 3317.7* | 4733.3**# |
| IL-10 | 38.4 | 45.0 | 500.1 | 1006.2**## |
| MCP-3 | 190.7 | 288.2 | 548.4 | 631.1* |
| IL-12p40 | 8.5 | 9.5 | 18.2*# | 21.4**## |
| MDC | 4826.0 | 5229.0 | 4904.0 | 3517.3 |
| IL-12p70 | 2.6 | 3.5 | 5.6**# | 5.9**# |
| IL-13 | 4.4 | 3.9 | 6.2 | 6.8# |
| PDGF-BB | 90.4 | 117.8 | 457.3*# | 447.5*# |
| IL-15 | 2.0 | 2.2 | 5.3****#### | 6.2****####$ |
| sCD40L | 5.6 | 7.0 | 18.7***### | 21.5***### |
| IL-17 | 1.1 | 1.6 | 2.7**# | 2.8**# |
| IL-1ra | 820.3 | 671.0 | 510.6 | 454.9 |
| IL-1a | 0.0 | 0.36 | 24.2***## | 33.9***### |
| IL-9 | 0.5 | 0.4 | 1.9 | 2.4*# |
| IL-1b | 1.6 | 2.1 | 5.7* | 7.7**## |
| IL-2 | 1.8 | 2.1 | 3.2 | 3.6* |
| IL-4 | 17.4 | 32.8 | 64.4***## | 72.4***## |
| IL-5 | 0.0 | 0.0 | 1.3*# | 0.97 |
| IL-6 | 0.0 | 35.6 | 309.9 | 348.2 |
| IL-7 | 4.5 | 8.6* | 23.3**# | 25.5**## |
| IL-8 | 159.9 | 2251.0* | 7139.0**# | 8227.3***## |
| IP-10 | 42.7 | 53.6 | 1914.3*# | 2912.7**## |
| MCP-1 | 8567.7 | 9087.7 | 8983.7 | 8757.3 |
| MIP-1a | 18.8 | 36.9 | 145.4 | 1161.0* |
| MIP-1b | 36.6 | 125.0 | 504.4 | 904.3*# |
| RANTES | 14.3 | 33.2 | 306.6 | 291.8 |
| TNFa | 4.0 | 14.4* | 166.7*# | 250.2**## |
| TNFb | 0.0 | 0.0 | 1.4 | 1.7 |
| VEGF | 27.4 | 47.3* | 81.8***# | 92.0***## |

Increased Phagocytic Activity in the LPS-High EEGs

Figure 6:
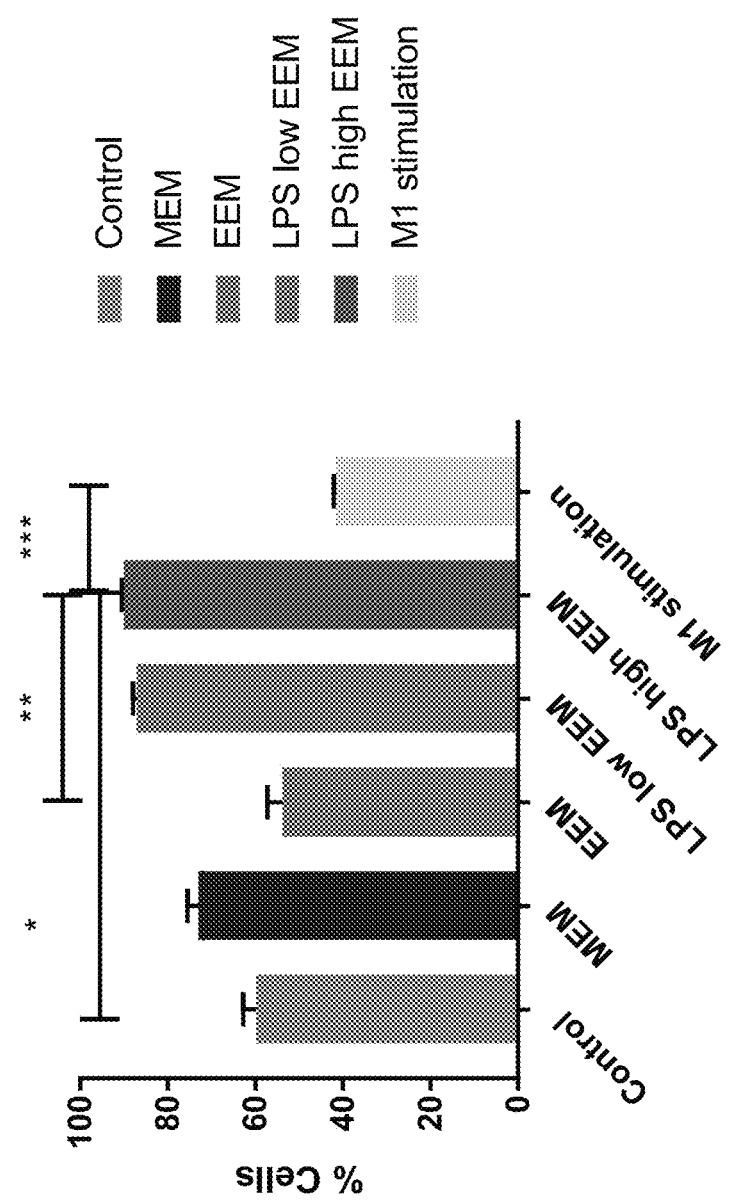
FIG. 6 shows that LPS-high-EEMs are strongly phagocytic using pHrodo Green *E. coli* bioparticles. Macrophages at day 7 of culture (Day 7 macrophages) were tested in their unstimulated state (control) or co-culture for an additional 3 days with either M1 promoting factors (M1 stimulation), exosomes from MSCs (EEMs), or exosomes from MCSs primed with a low (LPS-low-EEMs) or high (LPS-high-EEMs) concentration of LPS as described in methods. Post co-culture Day 10 macrophages were treated with pHrodo Green *E. coli* bioparticles and the ratio of CD14+ cells positive for pHrodo Green *E. coli* bioparticles to total CD14+ cells was designated as percent (%) cells as determined by flow cytometry. P values were compared to control; *$p</=0.05$,  $p</=0.005$, * $p</=0.0005$.

There was a significant increase in the percentage of cells containing pHrodo Green *E. coli* particles in the LPS-high EEMs compared to controls, EEMs and macrophages directly stimulated with M1 factors (FIG. 6) However, the amount of pHrodo Green *E. coli* particles within each cell (MFIs) was not statistically different between all of the groups (data not shown). While macrophages (CD14$^+$ CD90$^-$) co-cultured with MSCs (MEMs) gated with CD14 and CD90 showed a general increase in percentage of cells with phagocytic activity, the MFI was highest overall in this group and statistically higher than the EEMs and the M1 stimulated macrophages. Overall, the only group that had a significant increase in percentage of phagocytic cells were LPS-high EEMs.

LPS-EEGs Suppress In Vitro T-Cell Proliferation in the Immunopotency Assay (IPA).

Figures 7A, 7B:
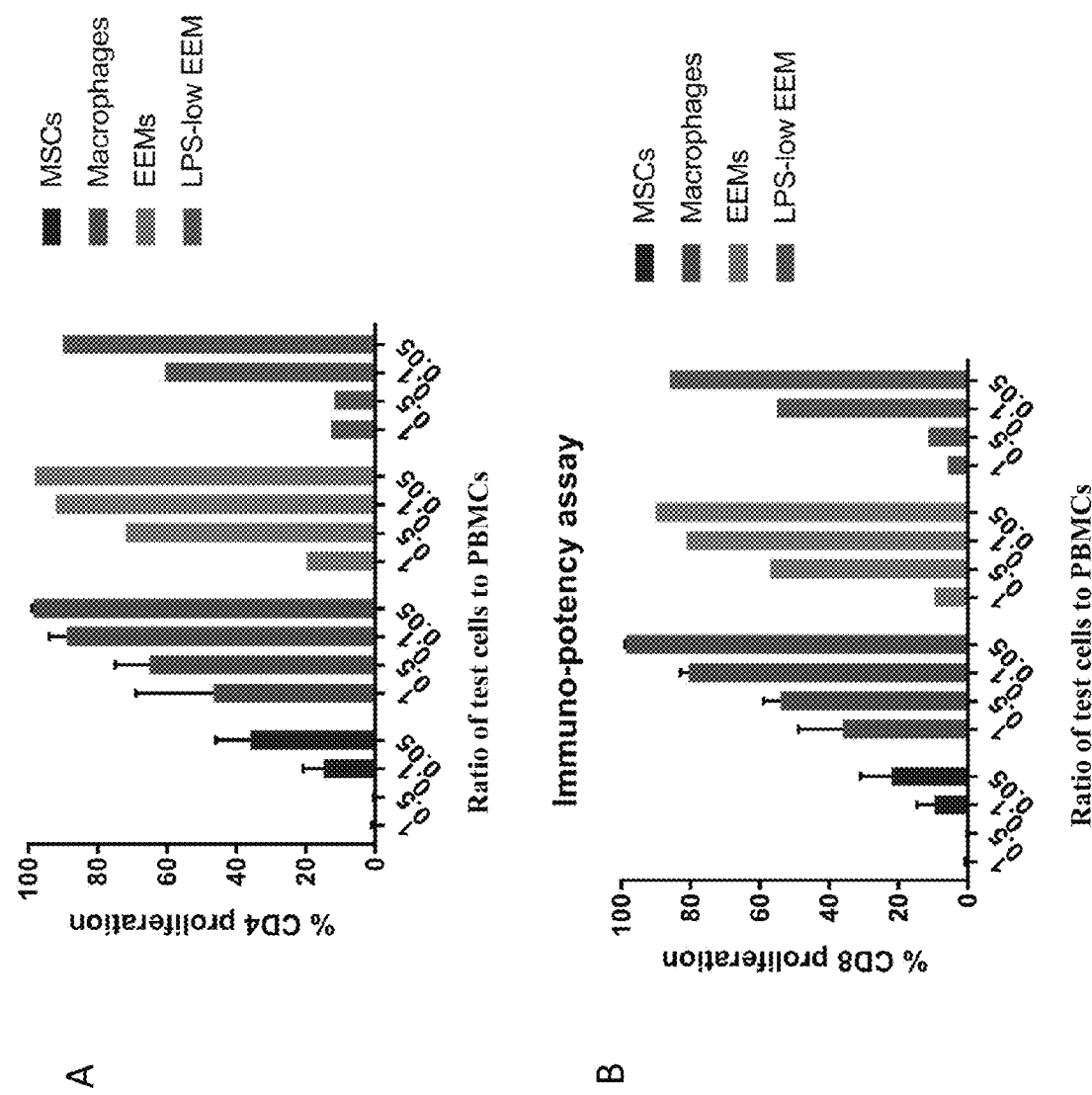
FIGS. 7A-7B show Immuno-potency assay (IPA) for growth inhibition of T-cells and measures the % proliferation of antibody activated (A) CD4+(helper T cells) or (B) CD8+(cytotoxic T cells) when co-cultured at various ratios with test cells that were either MSCs, control macrophages, EEMs, or LPS-EEMs. The % cell proliferation is compared to activated cells without the addition of test cells.

The ability of cells to immuno-modulate T-cell proliferation in vitro is thought to be predictive of efficacy in vivo. Using the IPA assay, as shown in FIGS. 7A-7B, we tested the ability of macrophages, EEMs or LPS-low EEMs to modulate the growth of primary T-helper cells (CD4+) or T-cytotoxic cells (CD8+) from peripheral blood mononuclear cell (PBMCs) when co-cultured at various ratios. The LPS-low EEMs compared to the other macrophage test groups (control macrophages or EEMs) were the most immune-suppressive to both T-cell types. MSCs were also tested in this assay and served as positive control inhibitor. Strong immunosuppression of T-cell growth by MSC has been well-documented (Bloom, D. et al. Cytotherapy, 2015, 17(2) 140-151) and MSCs were found to be very effective at suppressing proliferation of both CD4+ and CD8+ cells in the IPA assay. Almost 100% growth suppression for both CD4+ or CD8+ cells using MSCs at the 1:1 and 1:0.5 ratio while about 10-15% suppression at a 1:0.1 ratio occurred as shown in FIGS. 7A and 7B, respectively. At 1:1 and 1:0.5 there were relative degrees of a cell dose-dependent suppression of PBMC proliferation when comparing macrophage groups for suppression (i.e., control macrophages, EEMs or LPS-low-EEMs). The strongest suppression of proliferation for both CD4+ and CD8+ cells occurred using the LPS-low-EEMs. While proliferation using either macrophages or EEMs was marginally reduced about 55% proliferation for both CD4+ and CD8+ cells, there was only about 10% proliferation for both T-cell types for LPS-low-EEM ratio. IPA results demonstrate the immune-suppressive properties of LPS-low EEMs on CD4+ and CD8+ proliferation.

LPS-High EEMs Protect Mice from Lethal Radiation Injury in Part by Restoring Hematopoiesis.

Figures 8A, 8B, 8C:
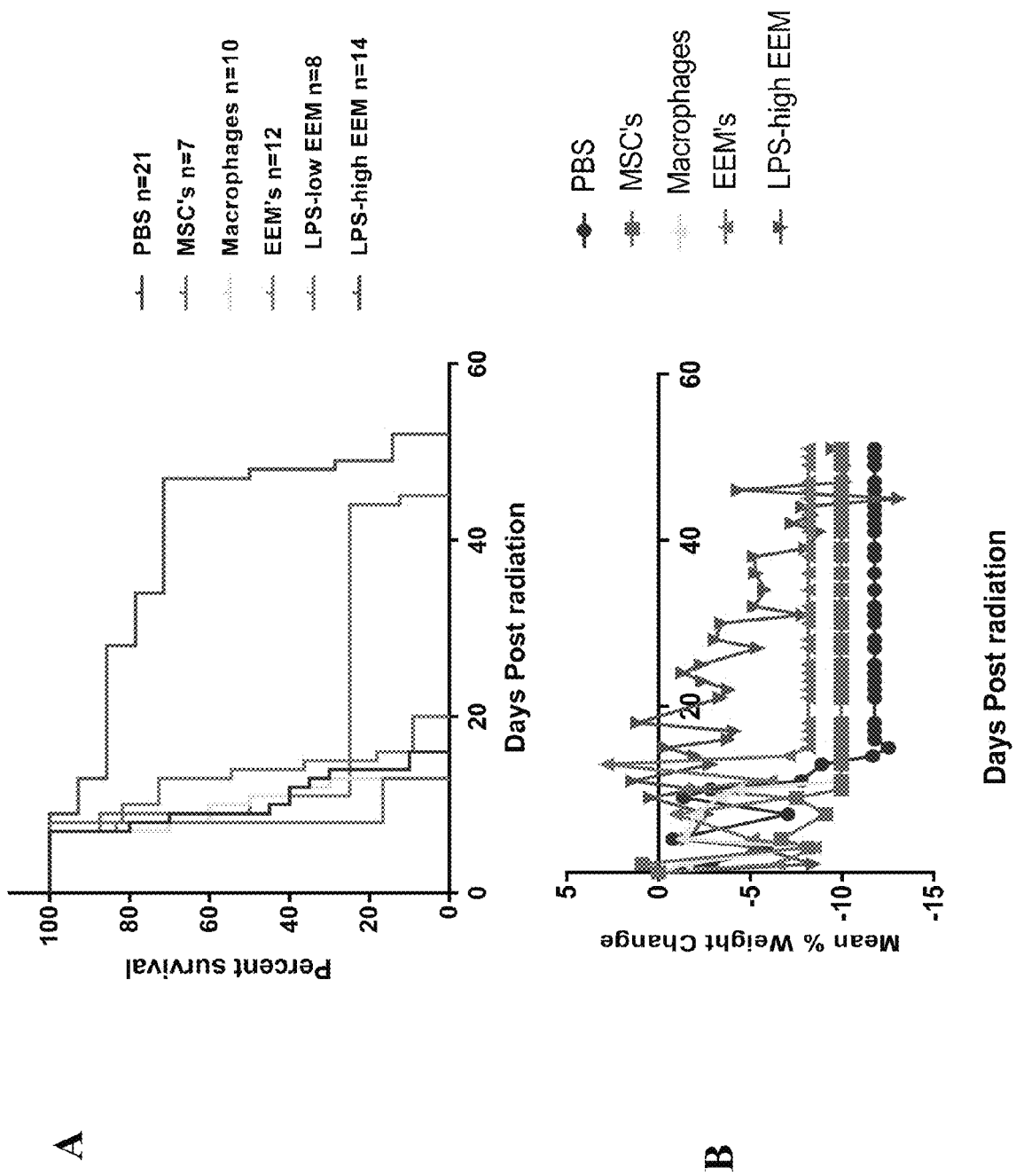
FIGS. 8A-8C show that treatment with LPS-high-EEMs significantly increased survival, improved weight loss and clinical scores in mice after challenge with lethal radiation. (A-C) On day 0, NOD.Cg-Prkdc$^{scid}$ Il2rg$^{tm1Wjl}$/SzJ (NSG) mice (from The Jackson Laboratory) received 4 gray (Gy) of lethal radiation followed by an intravenous treatment 4 hours later with PBS, 1×10$^6$ human bone marrow MSCs, Day 10 control macrophages, EEMs, LPS-low-EEMs or LPS-high-EEMs generated as described in the Examples.
Figures 8A, 8B, 8C:
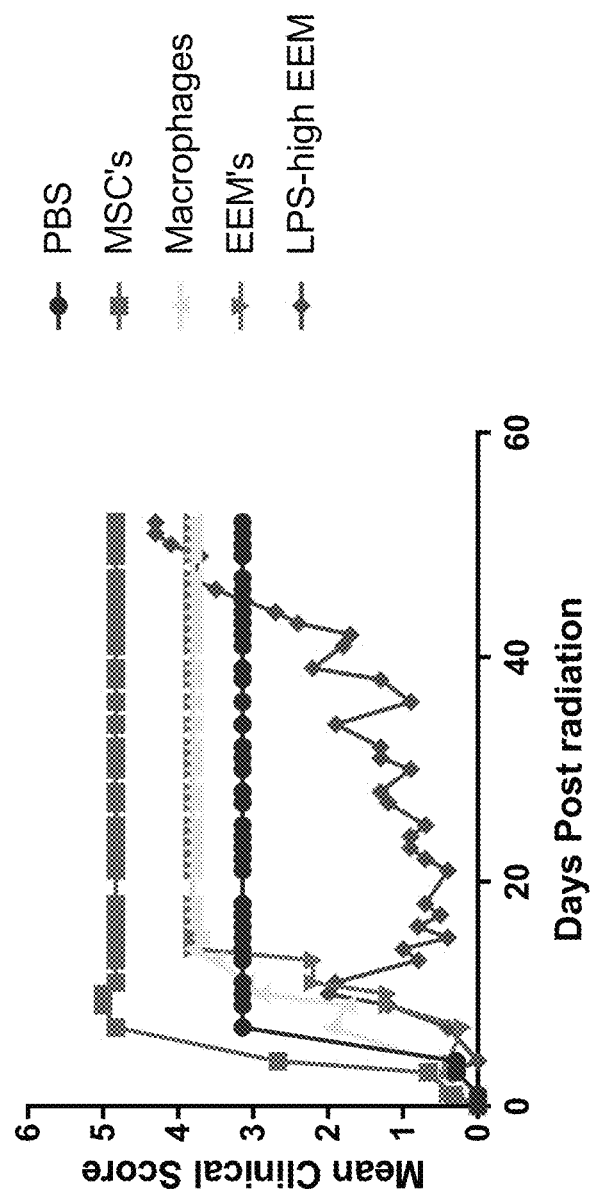

After a lethal dosage of radiation at 4Gy, a single intravenous treatment with MSCs or control-macrophages did not significantly protect against radiation injury compared to PBS treated controls and 100% of these mice died within 16 days. In contrast, either EEMs or LPS-low EEMs significantly improved mean survival from 10.6 days in the PBS control mice to 13.2 and 18.1 days, respectively (FIG. 8A). However, LPS-high EEMs treatment led to a sustained and prolonged survival with a significant improvement in mean and median survival of 40.7 days and 47.5 days, respectively. Unlike the other treatment groups, while mean percent weight change (FIG. 8B) and mean clinical score (FIG. 8C) worsened with time, LPS-high EEM treated mice temporarily recovered by Day 10 with clinical scores that retained somewhat normal for many weeks. For example, the mean clinical score in LPS-high EEM treated mice out to Day 40 post-challenge remained under 2.0 compared to other groups which ranged from 3.0 to 5.0 during the first week. While this protective effect was strong, it began to diminish starting at about Day 40 and the cumulative clinical score and weight progressively got worse and the remaining mice died on Day 48-52. This effect was seen after at least three independent studies.

To determine the effects of radiation on hematopoiesis, whole blood was assayed to determine complete blood counts (CBC) in the PBS, EEM and LPS-high EEM treated mice after lethal radiation exposure. Mean values were determined for three hematology populations: erythrocytes, leukocytes and thrombocytes (Table 5A, 5B, and 5C). While NSG mice are known to be deficient in T, B and NK cells, there were detectable levels of lymphocytes in the blood. Mice were first bled 4 days post-challenge and compared to age matched un-irradiated mice (N=10) as healthy controls. In general, by day 4, all irradiated groups developed pancytopenia as compared to healthy controls. For erythrocytes (Table 5A), the drop in cell numbers were small but significant due to the small variation between samples within each group. At Day 4, there were significant reductions in most leukocyte subsets (neutrophils, lymphocytes) in the treatment groups (Table 5B), although they remained generally higher in the PBS group. Interestingly, the greatest significant drop in leukocyte cell subsets was detected in LPS-high EEMs treated mice, especially for neutrophils, lymphocytes and monocytes. A significant and approximately equal 3-fold reduction in platelets was seen in all treatment groups (Table 5C).

Table 5, 5A, 5B, and 5C: LPS-EEM treatment significantly improved the complete blood count in mice after challenge with lethal radiation. (A-C) On day 0, NSG mice received 4Gy of lethal radiation followed by an i.v. treatment 4 hours later with PBS, or with $10^6$ cells of EEMs, LPS-low or high EEMs generated as described in Methods. Blood from fifteen non-irradiated age-matched NSG mice (normal control) was collected to serve as the source for the normal control baseline CBC values. Blood was harvested from 5-10 mice from each group at 4 days post radiation challenge and on day 32 and days 50-53 from survivors in the LPS-high-EEM group. The whole blood as analyzed within several hours on a Hemavet 950FS blood analyzer. The CBC values measured for the major blood cell types from subjects in the different treatment groups are shown in Table 5. CBC values for other hematologic panel markers for each of the three major blood groups (erythrocytes, leukocytes, and thrombocytes) are shown in Tables 5A, 5B, and 5C. Table 5A shows mean blood values of the erythrocyte panel, Table 5B shows mean blood values of the leukocyte panel, and Table 5C shows mean blood values of the thrombocyte panel. P values were compared to normal control mice *p</=0.05,  p</=0.005, * p</=0.0005.

TABLE 5

CBC values for major blood cell types (mean values)

| Group | Day post radiation | RBC (M/ul) | WBC (K/ul) | Neutrophils (K/ul) | Lymphocytes (K/ul) | Monocytes (K/ul) | Platelets (K/ul) | Platelet vol (EL) |
|---|---|---|---|---|---|---|---|---|
| Control | N/A | 4.6 | 1.37 | 1.06 | 0.21 | 0.065 | 608 | 4.5 |
| PBS | 4 | 4.3 | 0.49* | 0.14** | 0.24 | 0.03 | 191** | 4.3 |
| EEM | 4 | 3.7 | 0.19** | 0.03** | 0.08 | 0.013 | 219** | 4.2* |
| LPS-high EEM | 4 | 3.7* | 0.21*** | 0.02*** | 0.05* | 0.01** | 187*** | 4.5 |
| LPS-high EEM | 32 | 4.1 | 1.68 | 1.21 | 0.36 | 0.05 | 379* | 5.0*** |
| LPS-high EEM | 50-53 | 5.8 | 1.48 | 0.92 | 0.40 | 0.11 | 316** | 5.0*** |

TABLE 5A

Erythrocyte panel (mean values)

| Group | Day post radiation | RBC (M/ul) | Hb (g/dL) | HCT (%) | MCV (fL) | MCH (pg) | MCHC (g/dL) | RDW (%) |
|---|---|---|---|---|---|---|---|---|
| Normal control | N/A | 4.6 | 6.2 | 22.8 | 48 | 13.6 | 28.2 | 16.8 |
| PBS | 4 | 4.3 | 5.8 | 20.1 | 46.3* | 13.3 | 28.7 | 15.9** |
| EEM | 4 | 3.7 | 4.8* | 17.2 | 46.6* | 12.9* | 27.8 | 15.6*** |
| LPS-high-EEM | 4 | 3.7* | 5.0* | 17.6* | 46.7** | 13.3 | 28.5 | 15.9*** |
| LPS-high EEM | 32 | 4.1 | 5.4 | 21.6 | 52.2*** | 13.5 | 26.1* | 21.1*** |

TABLE 5B

Leukocyte panel (mean values)

| Group | Day post radiation | WBC (K/ul) | Neutrophils (K/ul) | Lymphocytes (K/ul) | Monocytes (K/ul) | Eosinophils (K/ul) | Basophils (K/ul) |
|---|---|---|---|---|---|---|---|
| Normal control | N/A | 1.37 | 1.06 | 0.21 | 0.065 | 0.031 | 0.014 |
| PBS | 4 | 0.49* | 0.14** | 0.24 | 0.03 | 0.04 | 0.03 |
| EEM | 4 | 0.19** | 0.03** | 0.08 | 0.013 | 0.01 | 0.003 |
| LPS-high EEM | 4 | 0.21*** | 0.02*** | 0.05* | 0.01** | 0.006 | 0.003 |
| LPS-high EEM | 32 | 1.68 | 1.21 | 0.36 | 0.05 | 0.04 | 0.011 |

TABLE 5C

Thrombocyte panel (mean values)

| Group | Day post radiation | Platelets (K/ul) | Platelet volume (fL) |
|---|---|---|---|
| Normal control | N/A | 608 | 4.5 |
| PBS | 4 | 191** | 4.3 |
| EEM | 4 | 219** | 4.2* |
| LPS-high EEM | 4 | 187*** | 4.5 |
| LPS-high EEM | 32 | 379* | 5.0*** |

The levels of most blood cell types of all three hematology panels were restored to normal levels by Day 32 in the surviving LPS-high EEM mice. Accordingly, most of these mice displayed near normal weight and clinical scores (FIGS. 8A-8B). For erythrocytes, most of the values went to normal levels with MCV (mean corpuscular volume) and RDW (red cell distribution width) significantly higher than normal controls, likely from increased reticulocytosis. Both of these parameters indicate stimulation of red cell production by the LPS-high EEMs. Furthermore, the mean values for leukocyte subsets were all restored to normal levels by Day 32. While platelets did not reach normal levels, amounts significantly improved, (Table 5C), with also significantly higher platelet volume indicating increased production of immature platelets from the BM hematopoietic progenitor cells. Significantly the CBC panel performed on the relapsed moribund LPS-high EEM treated mice (Day 50-53) was still very similar to the CBCs of the recovered healthy Day 32 LPS-high EEM treated mice.

In another lethal radiation study, mice from different treatment groups were euthanized at key time points post challenge for gross necropsy and were examined by histology to determine the status of their hematopoietic organs (bone marrow and spleen) and possible cause of death. Healthy, un-irradiated NSG mice served as normal control tissue while several sets of mice were irradiated at 4Gy and treated with either PBS (control) or LPS-High EEMs as described. Irradiated PBS control mice showing overt signs of ARS (Day 9) were euthanized and a detailed gross necropsy was conducted including organ weight/morphology and histology and compared to healthy control tissue. Two sets of LPS-High EEM treated mice were also compared—the healthy Day 30 mice and the Day 50-53 relapsed mice. Spleen weight can be used as reliable marker for presence or lack of extra-medullary hematopoiesis. As shown in Table 6 below, there was a significant drop in both spleen weight and spleen % body weight (BW) in the irradiated untreated mice compared to the spleens of normal mice. In contrast, mean spleen weights were similar to normal in the LPS-High EEM treated mice at Day 30 post-challenge. However, the LPS-High EEM treated mice at Day 50-53 showed clinical signs of relapse and weight loss including significantly lower mean spleen weights and spleen % BW as compared to those values obtained from healthy control mice.

TABLE 6

| Treatment group | Spleen weight (mg) | Spleen % BW |
|---|---|---|
| Normal | 28.1 | 0.11 |
| 4GY untreated (Day 8) | 9.3* | 0.05* |
| 4GY LPS-High EEM (Day 30) | 34.4 | 0.15 |
| 4GY LPS-High EEM (Day 50-53) | 12.3* | 0.07* |

*P => 0.05

The spleen sizes were also examined across the treatment groups. Day 8 irradiated, untreated mice compared to the normal mice indicated there was clear histopathology present with absence of hematopoietic cells (both progenitor and mature cells types) in both the spleen and bone marrow. This was clearly reflected in the profound reduction seen in the CBCs (Table 5). In contrast, spleen size of the LPS-high Day 30 mice showed healthy and prominent active hematopoietic tissue in the bone marrow and spleen, and again also reflected in a re-established CBC (Table 5). Interestingly, the histopathology of the blood, spleen and bone marrow of Day 50-53 moribund LPS-high EEM mice still remained fairly unremarkable, and all showed hematopoietic tissue in the bone marrow and marked extra-medullary hematopoiesis in the spleen. Even though the mean spleen size was reduced in these mice, signs of both a normal CBC and spleen and BM histology indicate that the moribund LPS-high EEM mice after Day 50 most likely did not die from severe anemia (low RBC counts) or leukopenia (low white cell count) but from another undetermined reason. Therefore, it appears that a single injection of LPS-high EEMs can restore a functioning hematopoiesis in the bone marrow and the spleen in the mice long term after challenge with lethal radiation and that death in these mice may not be due to the loss of radioprotection in these tissues.

LPS-High-EEMs Protect Mice from Lethal Radiation Injury by Restoring Hematopoietic Tissue.

Figures 9A, 9B:
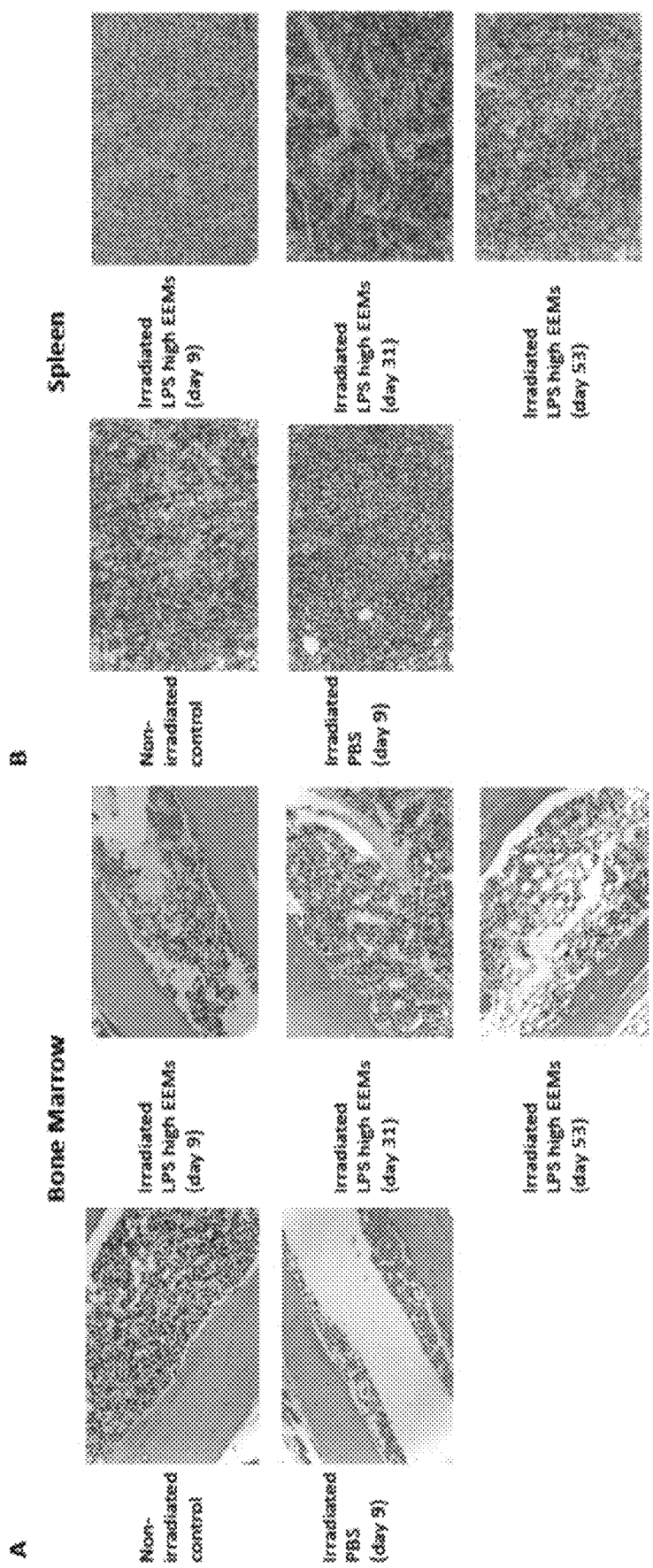
FIGS. 9A-9B show tissue histology of bone marrow and spleen samples. Histology shows that human LPS-high-EEM treatment protects against tissue damage in the bone marrow and spleen of mice after lethal radiation injury. On day 0, MSG mice received either no radiation (normal healthy control) or 4Gy of lethal radiation. 4 hours after exposure, mice received an intravenous treatment of PBS or 10$^6$ LPS-high-EEMs. Bone marrow and spleen tissue samples were taken 9 days post radiation from PBS controls and LPS-high-EEM treated mice. Samples were also taken from the LPS-high-EEM treated mice 31 days and 53 days post radiation exposure.

To identify which organs and tissues may be protected by LPS-high EEM treatment, we compared histology of BM from femur (FIG. 9A) and spleens (FIG. 9B) of normal non-irradiated mice to irradiated mice with or without treatment at different times post-challenge. By gross necropsy, the spleens were most affected by 4Gy radiation exposure, while overt changes to the heart, liver and kidneys were less obvious (data not shown). Compared to the histologic sections of BMs and spleens from healthy mice (FIGS. 9A and 9B), moribund PBS treated mice at day 9 post-irradiation showed a marked absence of hematopoietic cellularity in the BM and total lack of extra-medullary hematopoiesis in the spleen with clear hemorrhage (FIGS. 9A and 9B, respectively). In contrast, there were markedly more hematopoietic cells present in the LPS-EEM treated mice at day 9 post-irradiation (FIGS. 9A and 9B). At this time, cellularity present in the BM cavity graded from 1 to 5 (indicating most to least) was only 4 to 5 in the untreated mice post-radiation challenge, but ranged from 0.5 to 3.0 in the LPS-high EEM mice. Improvement continued in these mice at day 30 with strong to moderate hematopoietic activity in the BM of the femur but also in the pelvis and sternum with an intense hematopoietic component present in spleen. Interestingly even during clinical symptom relapse at day 53, hematopoietic tissue in the BM and spleen was still distinctly present in the LPS-high EEM treated mice, similar to what we observed in CBCs.

LPS-High EEMos Protect Mice from Lethal Radiation Injury

After a lethal dosage of radiation at 4Gy, a single intravenous treatment with control monocytes or EV (exosome) educated monocytes (EEMos) did not significantly protect against radiation injury compared to PBS treated controls and 100% of these mice died within 12 days. In contrast, LPS-high EEMos treatment led to a sustained and prolonged survival with a significant improvement; all mice survived for 45 days. Unlike the other treatment groups, while mean percent weight change (FIG. 8B) and mean clinical score (FIG. 8C) worsened with time, LPS-high EEM treated mice temporarily recovered after Day 10 and both weights and clinical scores remained normal for many weeks until about Day 40. As also seen in the treatment studies with the LPS-high EEMs, after a single treatment the effects of the LPS-high EEMos began to diminish starting at about Day 40 and the cumulative clinical score and weight progressively got worse and the mice died on Day 45-49.

To determine the effects of radiation on hematopoiesis, whole blood was assayed to determine complete blood counts (CBC) in the PBS, EEMos and LPS-high EEMos treated mice after lethal radiation exposure. Mean values were determined for three hematology populations: erythrocytes (RBCs), leukocytes (WBC, neutrophils, lymphocytes and monocytes) and thrombocytes (platelets and platelet volume) (Table 7). Blood from non-irradiated age-matched NSG mice (normal control) was collected to serve as the source for the normal control baseline CBC values. LPS-EEMos treatment significantly improved the complete blood count in mice after challenge with lethal radiation. Blood was harvested from the mice from each group at 5 days post radiation challenge and on day 30 from the surviving members in the LPS-high EEM group. The whole blood was analyzed within several hours on a Hemavet 950 FS blood analyzer. As seen in the CBC results in the same animal model using LPS-high EEMs, at Day 5 the CBC dropped significantly for most of the cells types in each hematology population. However, CBCs significantly improved to normal levels, except platelets (which did improve to near normal levels) at Day 30 and even Day 48, when the mice relapsed and were moribund.

somes were not effective in protecting from lethality. In contrast, as shown previously at this same dose, education of either monocytes or macrophages with LPS-high exosomes was successfully able to generate cells that were protective in the radiation model. This indicates that this exosome dose is enough to effectively educate cells protective for lethal radiation injury in mice, but not enough to be effective when used directly.

Figures 10A, 10B, 10C:
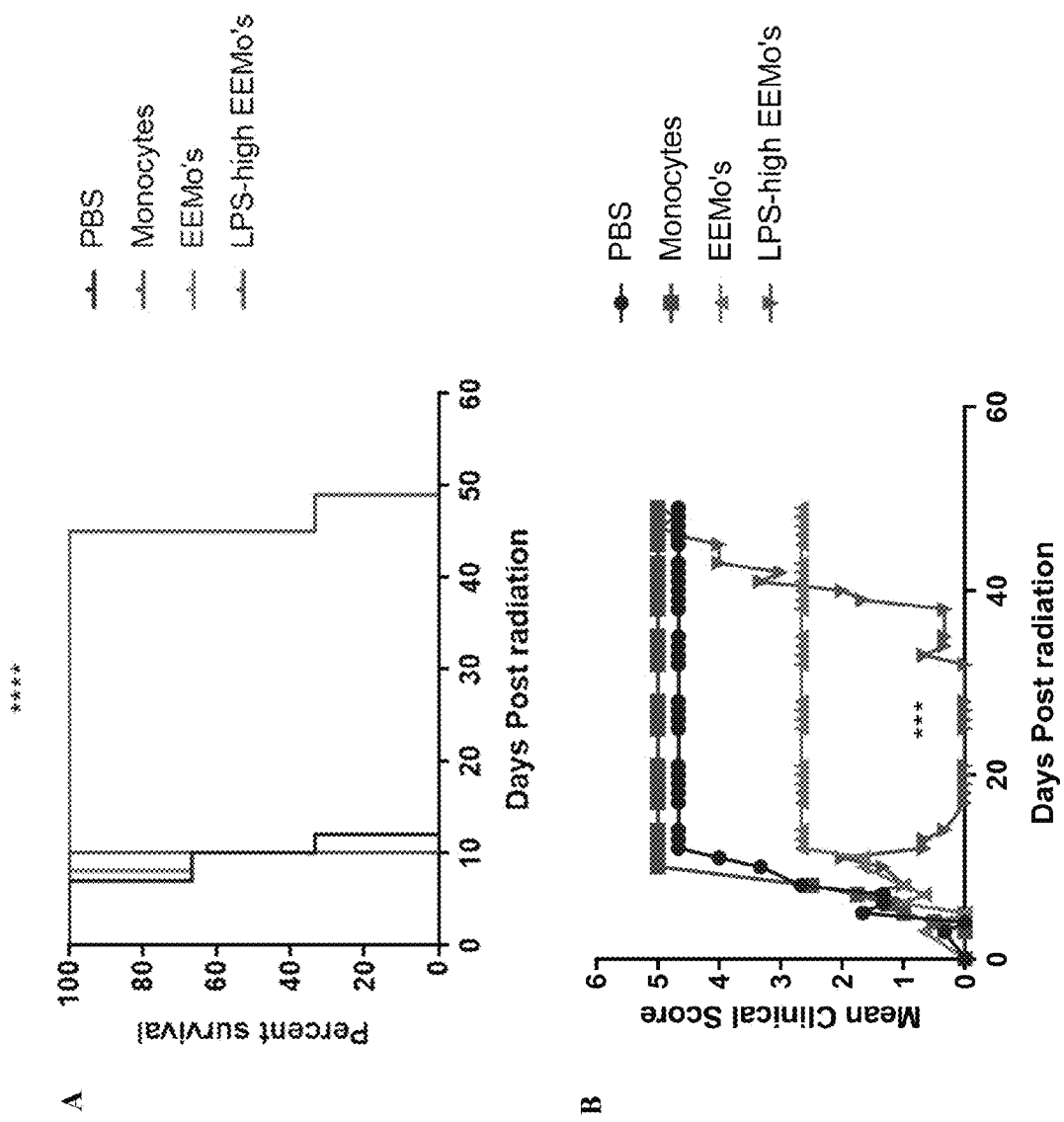
FIGS. 10A-10C show treatment with LPS-high-EEMos significantly increased survival, improved weight loss and clinical scores in mice after challenge with lethal radiation. (A-C) On day 0, NOD.Cg-Prkdcscid Il2rgmiWJlfSzJ (NSG) mice (from The Jackson Laboratory) received 4 gray (Gy) of lethal radiation. 4 hours later mice received an intravenous treatment with either PBS or 1×10$^7$ of control monocytes, EEMos, or LPS-high-EEMos generated as described in Example 1.
Figures 10A, 10B, 10C:
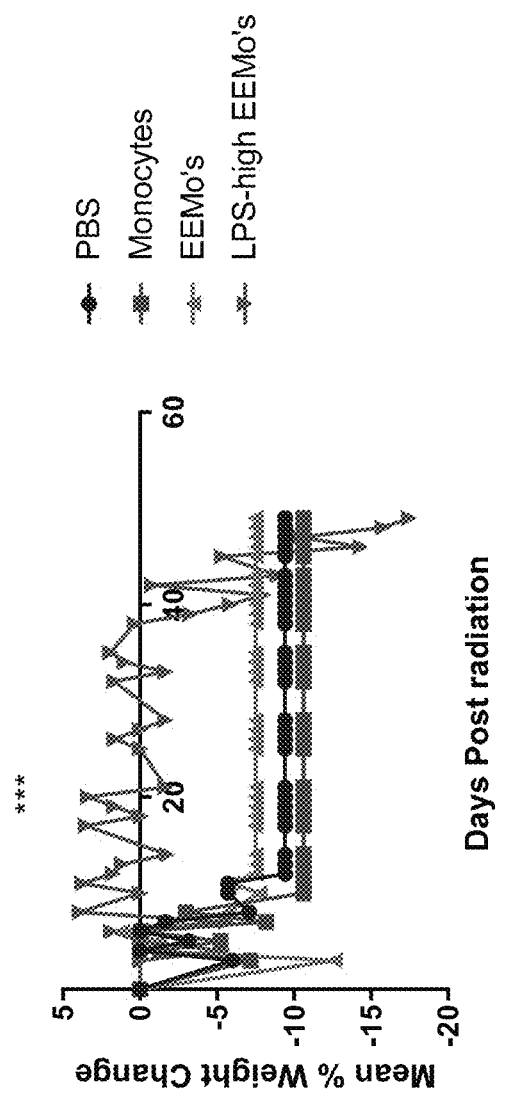
Figures 12A, 12B, 12C:
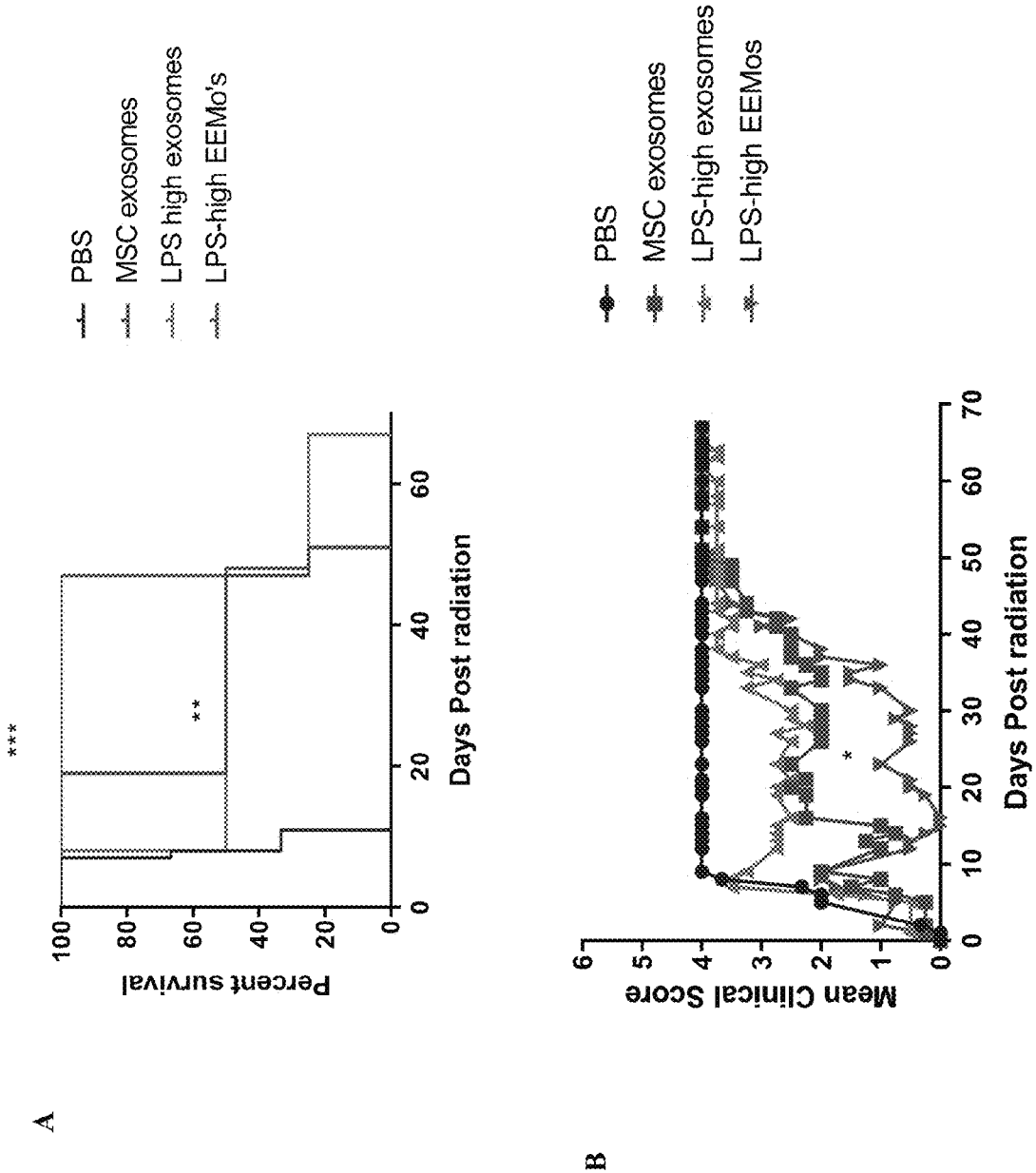
FIGS. 12A-12C show that direct treatment with high doses of exosomes isolated from LPS primed MSCs can significantly increase survival, decrease radiation exposure associated weight loss, and improve clinical scores in mice after challenge with lethal radiation. On day 0, NSG mice (from The Jackson Laboratory) received 4Gy of lethal radiation. 4 hours after radiation exposure, mice received intravenous treatment with either PBS, exosomes isolated from unstimulated MSCs (MSC-EVs at a concentration of 5.0×10$^9$ particles/100 µl PBS), exosomes isolated from MSCs primed with high concentration LPS (LPS-high-EVs at a concentration of 5.0×10$^9$ particles/100 µl PBS), or monocytes educated with exosomes at a concentration 5.0× 10$^9$ particles/100 µl, the exosomes for monocyte education having been isolated from MSCs primed with high concentration LPS.

Increasing the number of exosomes for direct use in the radiation model was then tested. Exosomes from either unstimulated MSC exosomes or LPS-high exosomes at a two-fold increase to $5.0 \times 10^9$, produced significant improvement in mean survival for both the MSC-exosome and the LPS-high exosome treated mice compared to the PBS control mice (FIG. 12A). When LPS-high exosomes at this higher dose were also used to educate monocytes to generate LPS-high EEMos, significant improvement in survival compared to control mice was also seen as expected (FIG. 12A). This higher exosome dose to generate LPS-high EEMos did not appear to improve either clinical outcome or prolong survival significantly compared with education using a lower dose (see FIG. 10A). As with either LPS-high EEMs or LPS-high EEMos, mice treated with high dose exosomes also showed significant improvement in both the mean clinical score (FIG. 12B) and mean % weight change. (FIG. 12C). As seen previously using LPS-high EEMs or LPS-EEMos both the clinical score and % weight changes worsened with time starting at day 40 in mice treated directly with higher dose MSC or LPS-high exosomes and all of the mice died by about day 50. However is noteworthy that the clinical scores in the mice treated with LPS-high EEMos were significantly better compared to directly treating with either set of exosomes (FIG. 12B).

TABLE 7

CBC values for major blood cell types (mean values)

| Group | Day post radiation | RBC (M/μl) | WBC (K/μl) | Neutrophils (K/μl) | Lymphocytes (K/μl) | Monocytes (K/μl) | Platelets (K/μl) | Platelet volume (fL) |
|---|---|---|---|---|---|---|---|---|
| Normal Control | N/A | 8.6 | 4.31 | 2.13 | 1.63 | 1.63 | 954.0 | 4.8 |
| PBS | 5 | 8.6 | 0.45*** | 0.11*** | 0.29* | 0.03*** | 298.0** | 4.8 |
| EEMos | 5 | 8.3 | 0.36*** | 0.06*** | 0.23* | 0.04*** | 340.0*** | 4.4 |
| LPS-high-EEMos | 5 | 8.7 | 0.53** | 0.13*** | 0.41 | 0.41** | 316.0*** | 4.9 |
| LPS-high-EEMos | 30 | 7.46* | 2.73 | 1.19 | 1.23 | 0.125 | 498.45*** | 5.23* |
| LPS-high-EEMos | 48 | 9.81 | 4.79 | 2.42 | 1.97 | 0.20 | 691.67* | 4.87 |

*p </= 0.05,
**p </= 0.005,
***p </= 0.0005

Figure 11:
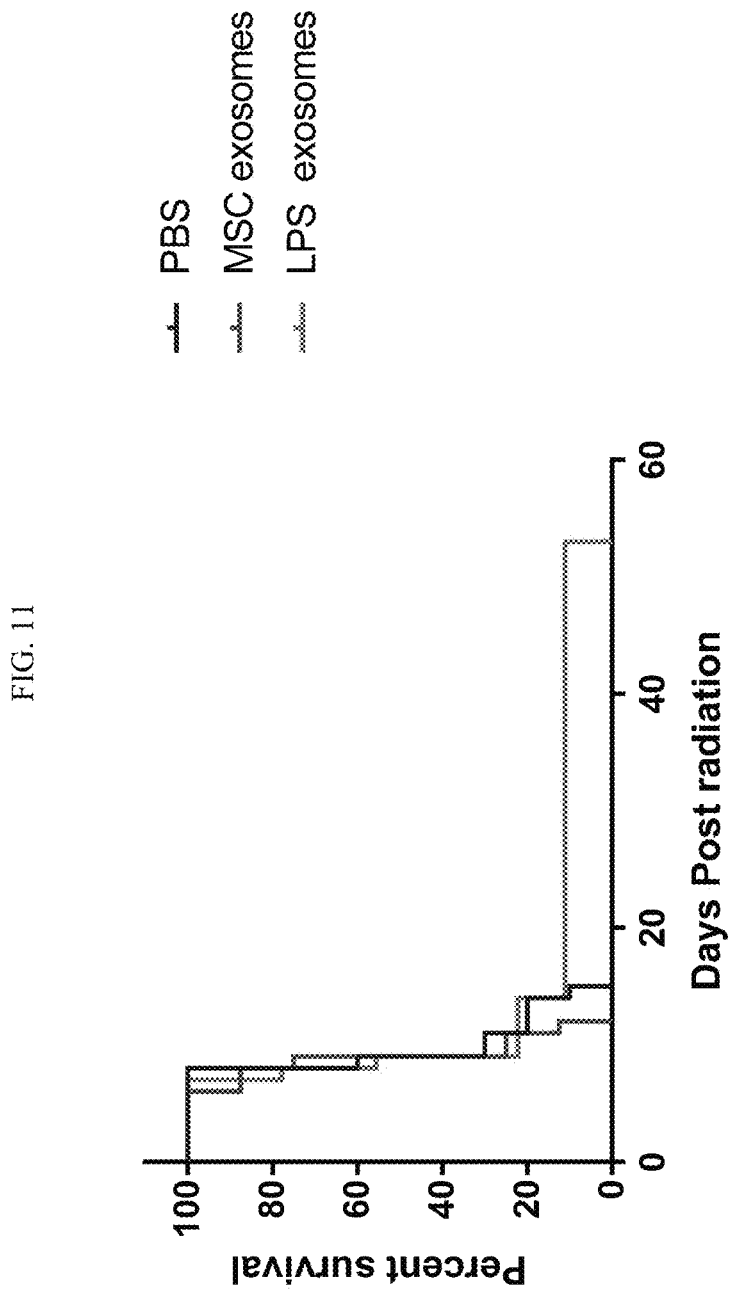
FIG. 11 shows direct treatment with exosomes is ineffective at treating mice after challenge with lethal radiation. The exosome treatment dosage (particle number) used to treat each mouse was the same dose used in co-culture with CD14+ macrophages or monocytes to create LPS-high-EEMs or LPS-low-EEMos. On day 0, NSG mice (from the Jackson Laboratory) received 4Gy of lethal radiation. 4 hours after radiation exposure, mice received intravenous treatment with either PBS, exosomes isolated from MSCs, or exosomes isolated from MSCs primed with LPS at a concentration of 2.5×10$^9$ particles/100 µl PBS.
Figures 12A, 12B, 12C:
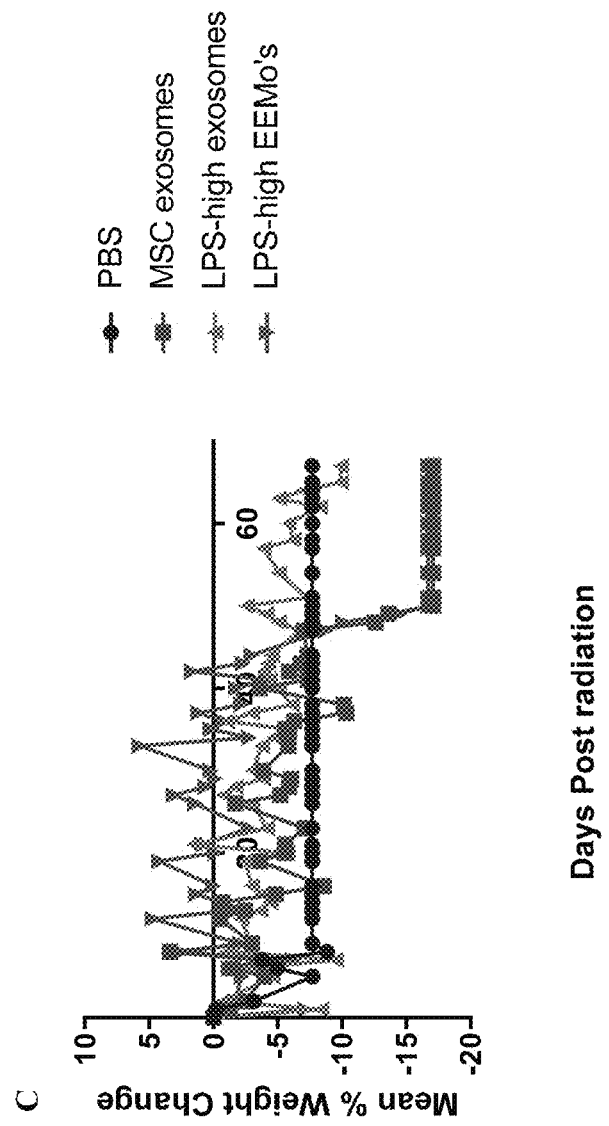

Exosome Dose Response Studies Indicate that LPS-High Exosomes can Also Protect Mice from Lethal Radiation Injury When the same concentration of LPS-high exosomes used to educate cells (either $10^6$ macrophages or $10^7$ monocytes) and successfully treat mice was used to directly treat mice, that dose was unable to significantly protect against death from radiation injury compared to PBS treated controls (FIG. 11.) Specifically after a lethal dosage of radiation at 4Gy, mice treated directly with a single intravenous treatment of $2.5 \times 10^9$ exosomes from either unstimulated MSCs or exosomes from MSCs stimulated with LPS (high) exo- High Dose Exosomes Treatment can Help Maintain Normal Complete Blood Counts in Mice after Lethal Radiation Injury To determine the effects of radiation and high dose exosome treatment on hematopoiesis, whole blood collected from the mice (FIG. 12) was assayed to determine complete blood counts (CBC) in the PBS, MSC exosome, LPS-high exosome, and the LPS-high EEMo treated mice after lethal radiation exposure as before. Mean values were determined for three key hematology populations: erythrocytes (RBCs), leukocytes (WBC, and types: neutrophils, lymphocyte and monocytes) and thrombocytes (platelets, platelet volume) (Table 8). Mice were first bled 4 days post-challenge and compared to non-irradiated mice as normal healthy controls. In general, by day 4, all irradiated groups developed pancytopenia as compared to healthy controls. As seen in previous studies at this time point (day 4-5), there were significant reductions in cell numbers within all groups; specifically WBC, neutrophils and platelets. Interestingly, there was also a significant increase in platelet volume at this early time point in both the LPS-high exosome and LPS-high EEMos not typically seen in earlier studies using LPS-high EEMos educated at the lower doses of exosomes. An increase in platelet volume typically indicates active proliferation of platelets. By day 30, the WBC and platelets recovered in the MSC exosome treated mice to normal levels but neutrophils remained lower and lymphocytes were statistically higher, both outcomes typically not seen in earlier studies with LPS-high EEMs and EEMos. In contrast the CBC levels in both LPS-high exosomes and the LPS-high EEMos returned to normal by day 30, except platelet volume remained higher in the LPS-high EEMos treated group. CBC determinations of blood samples from moribund mice at day 44 treated with LPS-high exosomes or LPS-high EEMos indicate that the hematology populations were still near normal compared with controls; although the WBC, neutrophils and platelet volume were significantly higher, but still within the normal healthy mouse range. The CBC of the surviving MSC-exosome treated mice at this time was similar to both LPS-high exosomes and LPS-high EEMos, except the platelet levels dropped below normal controls. The results indicate that the CBCs in mice treated with MSC exosomes, LPS-high exosomes or LPS-high EEMos recover after lethal radiation and that even during clinical relapse, the CBC levels still remain largely normal indicating a still functioning hematopoietic system.

Table 8 demonstrates that using higher dosages of MSC-exosomes, LPS-high exosomes and LPS-high EEMos significantly improved the complete blood count in mice after challenge with lethal radiation. On day 0, NSG mice received 4Gy of lethal radiation followed by an i.v. treatment 4 hours later with PBS, or $5 \times 10^9$ MSC-exosomes or LPS-high exosomes or $10^7$ monocytes treated with $5 \times 10^9$ LPS-high exosomes producing LPS-high EEMos. The educated monocytes were generated as described in Methods. Blood from non-irradiated age-matched NSG mice (normal control) was collected to serve as the source for the normal control baseline CBC values. Blood was harvested from surviving members from each group at day 4, day 30 and day 44 post radiation challenge. The whole blood as analyzed within several hours on a Hemavet 950FS blood analyzer. (A) Mean blood values of the erythrocyte, leukocyte panel, and thrombocyte panel is shown. P values were compared to normal control mice $*p</=0.05$, $p</=0.005$, $*p</=0.0005$.

TABLE 8

CBC values of major blood cell types (mean values)

| Group | Day post radiation | RBC (M/ul) | WBC (K/ul) | Neutrophils (K/ul) | Lymphocytes (K/ul) | Monocytes (K/ul) | Platelets (K/ul) | Platelet volume (fL) |
|---|---|---|---|---|---|---|---|---|
| Normal Control | n/a | 9.02 | 2.45 | 1.63 | 0.57 | 0.13 | 794.20 | 5.03 |
| PBS | 5 | 8.64 | 0.507 *** | 0.140 *** | 0.293 | 0.037 | 205.33 ** | 5.0 |
| MSC Exosomes | 5 | 8.39 | 0.28 *** | 0.037 *** | 0.137 | 0.023 | 195.67 ** | 4.97 |
| LPS-high Exosomes | 5 | 10.36 | 0.167 *** | 0.020 *** | 0.053 | 0.017 | 150.3 *** | 6.3 *** |
| LPS-high EEMos | 5 | 9.08 | 0.35 *** | 0.12 *** | 0.193 | 0.017 | 204.0 ** | 6.1 ** |
| MSC Exosomes | 30 | 7.46 | 2.38 | 0.835 * | 1.265 * | 0.2 | 880.0 | 5.75 ** |
| LPS-high Exosomes | 30 | 8.00 | 1.28 | 1.01 | 0.23 | 0.03 | 628.5 | 5.5 |
| LPS-high EEMos | 30 | 8.40 | 2.65 | 0.99 | 1.14 | 0.04 | 506.25 | 6.15 ** |
| MSC Exosomes | 44 | 6.86 | 4.09 * | 2.93 * | 0.75 | 0.23 | 430.5 * | 5.9 ** |
| LPS-high Exosomes | 44 | 9.94 | 4.42 ** | 4.09 *** | 0.23 | 0.06 | 567 | 5.85 * |
| LPS-high EEMos | 44 | 8.56 | 3.44 * | 2.82 ** | 0.45 | 0.11 | 790 | 5.63 ** |

DISCUSSION

Presently protection from radiation injury involves mainly supportive care and treatment with growth factors until an allogeneic BMT can be arranged. Development of cell-based therapies for radiation injury are appealing because of the potential to infuse them soon after radiation injury, produce multiple cytokines that can protect multiple organs from tissue injury and potentially restore hematopoiesis. Macrophages are long-lived phagocytic cells that differentiate from circulating monocytes and migrate into tissues to replace older cells or in response to signals from tissue injury. Once at the site of injured tissue, macrophages are an essential component in the host defense by clearing the site of pathogens, regulating inflammation, and promoting tissue repair.[47] In this environment, macrophages are very plastic and respond to products released from damaged tissue or pathogens (e.g. Toll-like receptors, LPS) to become microbicidal or M1-like. Local MSCs also sense these inflammatory products and respond to restore homeostasis by communicating with effector cells such as macrophages or T-cells through paracrine factors and exosomes[48-50] or direct contact[27] to promote an alternative M2 or T-regulatory phenotypes to orchestrate tissue repair. Direct exposure of macrophages to microbial factors such as LPS can polarize them to M1-like macrophages (M1 stimulation) while exposure of exosomes from LPS-primed MSCs can lead to the induction of reparative or more M2 like macrophages. The goal of this study was to determine if MSC-derived exosomes could be used to educate macrophages and monocytes into a radio-protective phenotype. In vivo bacterial sepsis models indicate MSCs help increase the percentage of detectable M2 macrophages[51] and LPS-primed MSCs are better at promoting tissue healing.[52] Furthermore, a recent study showed that exosomes from LPS-primed MSCs show improved wound healing in diabetic rat model.[37] Thus an interesting paradox exists where the same inflammatory mediator, such as LPS, can induce different downstream responses depending on which cell type it encounters.

Interestingly while LPS-high-EEMs showed the best radioprotection in our lethal radiation injury model, these macrophages did not fit the typical M2-like reparative phenotype. Based on cell surface marker and secretion profiles, M2 macrophages can be further classified into at least 4 subsets (M2a, b, c, d).[53] Which current subset, if any, might be most effective at treating radiation injury is unclear. Expression of CD163, CD206, CD274 (PD-L1) and CD273 (PD-L2) decreased compared to the EEMs, LPS-low EEMs and MEMs and essentially reversed to normal macrophage levels. However, like MEMs also effective in the radiation model, strong CD73 ecto-nucleotidase expression likewise occurred in the LPS-EEMs.[27] Increased adenosine production, along with huge increases in IDO expression (the enzyme involved in T-cell suppression by tryptophan degradation)[54] along with low expression of CD16 and M1 markers CD86 and HLA-DR indicate that T-cell suppression may be very important mechanism of action in the LPS-high EEMs. Besides this immunosuppression and immunomodulation, the LPS-high EEMs cells also have strong anti-inflammatory characteristics with increased phagocytosis aiding in the rapid clearance of cell debris.

The LPS-EEMs secreted significantly higher levels of a variety of anti-inflammatory cytokines, chemotactic factors, and growth factors compared to either control macrophages or EEMs. IL-6, a hallmark biomarker for MEMs, has been described to induce alternatively activated macrophages[55], promote mucosal healing from colitis[56], and cartilage self-repair by MSCs[57] and decreased ICAM-1 secretion, both known to reduce radiation-induced inflammation.[24,58] LPS-high-EEMs also secreted significant levels of other cytokines with anti-inflammatory activities such as, IL-4, IL-10 and IL-13. However, there were also significant increases in levels with pro-inflammatory tendencies including TNF-α, IL-1b, IFN-g, IL-12p40-p70, IL-15 and IL-17. However, except for TNF-α, in general the fold increase in many of them were not at the same level as found for many of the anti-inflammatory cytokines. The large increase in chemotactic factors such as MCP-3, IL-8, and IP-10 was also seen and may attract other monocytes, macrophages and neutrophils to site to treat radiation injury. The key to effectiveness of the LPS-EEMs might be due to the increases in growth factors such as EGF, FGF and G-CSF and GM-CSF. Indeed, the latter two growth factors are used clinically to treat radiation associated illness. Since the LPS-high-EEMs were more effective than the LPS-low-EEMs, two factors, FLT-3L, a stem cell growth factor which stimulates the growth of blood progenitors and IL-15 a regulator of proliferation of T-cells found significantly elevated in the LPS-high-EEMs may indicate their importance for an improved therapeutic outcome seen in the radiation mouse model. Based on the secretion profile (IL-10, IL-12, TNF-alpha, IP-10), LPS-high-EEMs most resemble M2-d subtype of macrophages, however there are also many unique differences such as high IL-6 and CD73 which indicate they belong to novel and distinct subset of activated macrophages. LPS-high-EEMos are characterized by high expression of PD-L1 and CD73, IL-15, and IL-6 and low expression of CD206, CD163, CD86, and CD16 compared to control monocytes.

After a lethal dose of radiation, all the animals presented with acute radiation syndrome (ARS) indicated by significant weight loss, changes in body posture and fur texture.[43] Since rapidly proliferating progenitor stem cells in the bone marrow are most radio-sensitive, as expected we found that all the mice had severe pancytopenia[1] and most cell values at Day 4 in all three panels (erythrocyte, leukocyte and thrombocyte panels) were significantly lower (except lymphocyte counts in the PBS group). Acute effects of radiation injury on the BM was markedly illustrated by Day 4 in all groups, but LPS-high-EEMs and LPS-high-EEMos were able to reverse most of these abnormalities by Day 32 and Day 30, respectively. In addition, while the median survival in the control groups occurred at Day 9, the majority (71%) of LPS-high-EEM treated mice were alive at Day 32. Likewise, the majority of LPS-high-EEMo treated mice were alive through day 40. Correspondingly, 20% of the mice in the LPS-low-EEM groups were also alive at this point. At this time, cell counts of the LPS-high-EEMs of all three panels recovered to normal or near normal levels; especially pronounced was the significant restoration of the white blood count and its component cells types. We have previously shown that by Day 12, >50% of normal human mononuclear cells injected i.v. were detected within the BM and spleen in irradiated mice. Therefore, based on the overall results presented here, reversal of ARS in the mice by LPS-high EEM may be due in part to their effectiveness in suppressing inflammation and restoring hematopoiesis in the BM and/or spleen. Indeed, studies have indicated that in response to stress, macrophages can play a role in supporting BM erythropoiesis.[59,60]

Since survival of irradiated mice treated with a single dose of either LPS-low-EEMs, LPS-high-EEMs, or LPS-high-EEMos was not permanent, we originally thought this was due to loss of the protective effect by the LPS-EEMs or LPS-EEMos on hematopoiesis. However, subsequent in vivo studies comparing healthy Day 30 mice to moribund Day 50-53 mice indicated that both normal CBCs and functional hematopoiesis in the BM and spleen were still present in Day 50-53 mice. Interestingly, surviving LPS-EEM treated mice from three independent radiation studies all died within a short period of time (Day 48-53). Upon necropsy and histology, no overlying cause of death was found in these mice. However the short-time frame of death post-radiation indicate that it may not be due to something accidental such as infection in the majority of mice but something specific such as a finite engraftment time of the human LPS-EEM in the mice. Therefore, an additional treatment of LPS-high-EEMs at strategic time points (Day 30) when the clinical scores begin to worsen, or repeated injections before those clinical symptoms return, may result in long-term survival.

Future studies of EEMs should focus on understanding the molecular mechanisms driving LPS-high EEMs in protecting mice from lethal radiation. RNA-seq analysis of exosomes could help identify factors important in the generation of radio-protective macrophages. Microarray analysis of microRNA (miRNA) from LPS-exosomes has showed a differential expression profile with elevated expression of certain miRNAs, such as the transcription factor, let-7b; proposed to be a driver in macrophage polarization.[37,61] Using an unbiased RNA-seq for MEMs, expression of genes involved positively correlated with several pathways that could be beneficial for anti-inflammatory effects or tissue repair (e.g. collagen formation or tissue development genes).[27] Testing whether survival post-radiation challenge can improve with increases in LPS-EEM dose and or with repeated cell treatments will be critical, as well as performing a time course to determine how long after radiation injury EEM infusion can be administered to still contribute to survival. Overall, we hope this work can provide the foundation to develop a more effective treatment of radiation injury using therapeutic macrophages and monocytes.

REFERENCES

1. Williams J P, Brown S L, Georges G E, et al. Animal models for medical countermeasures to radiation exposure. *Radiat Res*. April 2010; 173(4):557-578.
2. Fliedner T M, Chao N J, Bader J L, et al. Stem cells, multiorgan failure in radiation emergency medical preparedness: a U.S./European Consultation Workshop. *Stem Cells*. May 2009; 27(5):1205-1211.
3. Singh V K, Seed T M. A review of radiation countermeasures focusing on injury-specific medicinals and regulatory approval status: part I. Radiation sub-syndromes, animal models and FDA-approved countermeasures. *Int J Radiat Biol*. September 2017; 93 (9): 851-869.
4. Singh V K, Garcia M, Seed t M. A review of radiation countermeasures focusing on injury-specific medicinals and regulatory approval status: part II. Countermeasures for limited indications, internalized radionuclides, emesis, late effects, and agents demonstrating efficacy in large animals with or without FDA IND status. *Int J Radiat Biol*. September 2017; 93(9):870-884.
5. Singh V K, Newman V L, Seed T M. Colony-stimulating factors for the treatment of the hematopoietic component of the acute radiation syndrome (H-ARS): a review. *Cytokine*. January 2015; 71(1):22-37.
6. Koc O N, Gerson S L, Cooper B W, et al. Rapid hematopoietic recovery after coinfusion of autologous-blood stem cells and culture-expanded marrow mesenchymal stem cells in advanced breast cancer patients receiving high-dose chemotherapy. *J Clin Oncol*. January 2000; 18(2):307-316.
7. Pittenger M F, Mackay A M, Beck S C, et al. Multilineage potential of adult human mesenchymal stem cells. *Science*. Apr. 2, 1999; 284(5411):143-147.
8. Bernardo M E, Fibbe W E. Mesenchymal stromal cells: sensors and switchers of inflammation. *Cell Stem Cell*. Oct. 3, 2013; 13 (4): 392-402.
9. Eaton E B, Jr., Varney T R. Mesenchymal stem cell therapy for acute radiation syndrome:
innovative medical approaches in military medicine. *Mil Med Res*. 2015; 2:2.
10. Hu K X, Sun Q Y, Guo M, Ai H S. The radiation protection and therapy effects of mesenchymal stem cells in mice with acute radiation injury. *Br J Radiol*. January 2010; 83(985):52-58.
11. Lange C, Brunswig-Spickenheier B, Cappallo-Obermann H, et al. Radiation rescue: mesenchymal stromal cells protect from lethal irradiation. *PLoS One*. Jan. 5, 2011; 6(1):e14486.
12. Shim S, Lee S B, Lee J G, et al. Mitigating effects of hUCB-MSCs on the hematopoietic syndrome resulting from total body irradiation. *Exp Hematol*. April 2013; 41(4):346-353 e342.
13. Hu J, Yang Z, Wang J, et al. Infusion of Trx-1-overexpressing hucMSC prolongs the survival of acutely irradiated NOD/SCID mice by decreasing excessive inflammatory injury. *PLoS One*. 2013; 8(11):e78227.
14. Wang S, Qu X, Zhao R C. Clinical applications of mesenchymal stem cells. *J Hematol Oncol*. 2012; 5:19.
15. Galipeau J. The mesenchymal stromal cells dilemma—does a negative phase III trial of random donor mesenchymal stromal cells in steroid-resistant graft-versus-host disease represent a death knell or a bump in the road? *Cytotherapy. January* 2013; 15(1):2-8.
16. Chiossone L, Conte R, Spaggiari G M, et al. Mesenchymal Stromal Cells Induce Peculiar Alternatively Activated Macrophages Capable of Dampening Both Innate and Adaptive Immune Responses. *Stem Cells. July* 2016; 34(7):1909-1921.
17. Nemeth K, Leelahavanichkul A, Yuen P S, et al. Bone marrow stromal cells attenuate sepsis via prostaglandin E(2)-dependent reprogramming of host macrophages to increase their interleukin-10 production. *Nat Med*. January 2009; 15(1):42-49.
18. Cho D I, Kim M R, Jeong H Y, et al. Mesenchymal stem cells reciprocally regulate the M1/M2 balance in mouse bone marrow-derived macrophages. *Exp Mol Med*. Jan. 10, 2014; 46:e70.
19. Melief S M, Schrama E, Brugman M H, et al. Multipotent stromal cells induce human regulatory T cells through a novel pathway involving skewing of monocytes toward anti-inflammatory macrophages. *Stem Cells*. September 2013; 31(9):1980-1991.
20. Kim J, Hematti P. Mesenchymal stem cell-educated macrophages: a novel type of alternatively activated macrophages. *Exp Hematol*. December 2009; 37(12):1445-1453.
21. Sica A, Mantovani A. Macrophage plasticity and polarization: in vivo veritas. *J Clin Invest*. March 2012; 122(3): 787-795.
22. Keil F, Elahi F, Greinix H T, et al. Ex vivo expansion of long-term culture initiating marrow cells by IL-10, SCF, and IL-3. *Transfusion*. May 2002; 42(5):581-587.
23. Duchez P, Rodriguez L, Chevaleyre J, et al. Interleukin-6 enhances the activity of in vivo long-term reconstituting hematopoietic stem cells in "hypoxic-like" expansion cultures ex vivo. *Transfusion*. November 2015; 55(11): 2684-2691.
24. Koukourakis M I. Radiation damage and radioprotectants: new concepts in the era of molecular medicine. *Br J Radiol*. April 2012; 85(1012):313-330.
25. Roberts C A, Dickinson A K, Taams L S. The Interplay Between Monocytes/Macrophages and CD4(+) T Cell Subsets in Rheumatoid Arthritis. *Front Immunol*. 2015; 6:571.
26. Aggarwal S, Pittenger M F. Human mesenchymal stem cells modulate allogeneic immune cell responses. *Blood*. Feb. 15, 2005; 105(4):1815-1822.
27. Bouchlaka M N, Moffitt A B, Kim J, et al. Human Mesenchymal Stem Cell-Educated Macrophages Are a Distinct High IL-6-Producing Subset that Confer Protection in Graft-versus-Host-Disease and Radiation Injury Models. *Biol Blood Marrow Transplant*. June 2017; 23(6): 897-905.
28. Caplan A I, Correa D. The MSC: an injury drugstore. *Cell Stem Cell*. Jul. 8, 2011; 9(1):11-15.
29. Pittenger M. Sleuthing the source of regeneration by MSCs. *Cell Stem Cell*. Jul. 2, 2009; 5(1):8-10.
30. Phinney D G, Pittenger M F. Concise Review: MSC-Derived Exosomes for Cell-Free Therapy. *Stem Cells*. April 2017; 35(4):851-858.

31. Katsuda T, Kosaka N, Takeshita F, Ochiya T. The therapeutic potential of mesenchymal stem cell-derived extracellular vesicles. *Proteomics*. May 2013; 13 (10-11): 1637-1653.
32. Lai R C, Yeo R W, Lim S K. Mesenchymal stem cell exosomes. *Semin Cell Dev Biol*. April 2015; 40:82-88.
33. Yu B, Zhang X, Li X. Exosomes derived from mesenchymal stem cells. *Int J Mol Sci*. 2014; 15(3):4142-4157.
34. S ELA, Mager I, Breakefield X O, Wood M J. Extracellular vesicles: biology and emerging therapeutic opportunities. *Nat Rev Drug Discov*. May 2013; 12(5):347-357.
35. Tasso R, Ilengo C, Quarto R, Cancedda R, Caspi R R, Pennesi G. Mesenchymal stem cells induce functionally active T-regulatory lymphocytes in a paracrine fashion and ameliorate experimental autoimmune uveitis. *Invest Ophthalmol Vis Sci*. February 2012; 53(2):786-793.
36. English K, Ryan J M, Tobin L, Murphy M J, Barry F P, Mahon B P. Cell contact, prostaglandin E(2) and transforming growth factor beta 1 play non-redundant roles in human mesenchymal stem cell induction of CD4+CD25 (High) forkhead box P3+ regulatory T cells. *Clin Exp Immunol*. April 2009; 156(1):149-160.
37. Ti D, Hao H, Tong C, et al. LPS-preconditioned mesenchymal stromal cells modify macrophage polarization for resolution of chronic inflammation via exosome-shuttled let-7b. *J Transl Med*. 2015; 13(1):308.
38. Wen S, Dooner M, Cheng Y, et al. Mesenchymal stromal cell-derived extracellular vesicles rescue radiation damage to murine marrow hematopoietic cells. *Leukemia*. November 2016; 30(11):2221-2231.
39. Dominici M, Le Blanc K, Mueller I, et al. Minimal criteria for defining multipotent mesenchymal stromal cells. The International Society for Cellular Therapy position statement. *Cytotherapy*. 2006; 8(4):315-317.
40. Bloom D D, Centanni J M, Bhatia N, et al. A reproducible immunopotency assay to measure mesenchymal stromal cell-mediated T-cell suppression. *Cytotherapy*. February 2015; 17(2):140-151.
41. Thery C, Amigorena S, Raposo G, Clayton A. Isolation and characterization of exosomes from cell culture supernatants and biological fluids. *Curr Protoc Cell Biol*. April 2006; Chapter 3:Unit 3 22.
42. Sindrilaru A, Peters T, Wieschalka S, et al. An unrestrained proinflammatory M1 macrophage population induced by iron impairs wound healing in humans and mice. *J Clin Invest*. March 2011; 121(3):985-997.
43. Cooke K R, Kobzik L, Martin T R, et al. An experimental model of idiopathic pneumonia syndrome after bone marrow transplantation: I. The roles of minor H antigens and endotoxin. *Blood*. Oct. 15, 1996; 88(8):3230-3239.
44. Kim J, Escalante L E, Dollar B A, Hanson S E, Hematti P. Comparison of breast and abdominal adipose tissue mesenchymal stromal/stem cells in support of proliferation of breast cancer cells. *Cancer Invest*. October 2013; 31(8):550-554.
45. Linden J. Molecular approach to adenosine receptors: receptor-mediated mechanisms of tissue protection. *Annu Rev Pharmacol Toxicol*. 2001; 41:775-787.
46. Yang L, Froio R M, Sciuto T E, Dvorak A M, Alon R, Luscinskas F W. ICAM-1 regulates neutrophil adhesion and transcellular migration of TNF-alpha-activated vascular endothelium under flow. *Blood*. Jul. 15, 2005; 106(2):584-592.
47. Gordon S, Martinez F O. Alternative activation of macrophages: mechanism and functions. *Immunity*. May 28, 2010; 32(5):593-604.
48. Blazquez R, Sanchez-Margallo F M, de la Rosa 0, et al. Immunomodulatory Potential of Human Adipose Mesenchymal Stem Cells Derived Exosomes on in vitro Stimulated T Cells. *Front Immunol*. 2014; 5:556.
49. Zhu Y G, Feng X M, Abbott J, et al. Human mesenchymal stem cell microvesicles for treatment of *Escherichia coli* endotoxin-induced acute lung injury in mice. *Stem Cells*. January 2014; 32(1):116-125.
50. Zhang Y, Chopp M, Meng Y, et al. Effect of exosomes derived from multipluripotent mesenchymal stromal cells on functional recovery and neurovascular plasticity in rats after traumatic brain injury. *J Neurosurg*. April 2015; 122(4):856-867.
51. Lombardo E, van der Poll T, DelaRosa O, Dalemans W. Mesenchymal stem cells as a therapeutic tool to treat sepsis. *World J Stem Cells*. Mar. 26, 2015; 7(2):368-379.
52. Yao Y, Zhang F, Wang L, et al. Lipopolysaccharide preconditioning enhances the efficacy of mesenchymal stem cells transplantation in a rat model of acute myocardial infarction. *J Biomed Sci*. Aug. 20, 2009; 16:74.
53. Roszer T. Understanding the Mysterious M2 Macrophage through Activation Markers and Effector Mechanisms. *Mediators Inflamm*. 2015; 2015:816460.
54. Meisel R, Zibert A, Laryea M, Gobel U, Daubener W, Dilloo D. Human bone marrow stromal cells inhibit allogeneic T-cell responses by indoleamine 2,3-dioxygenase-mediated tryptophan degradation. *Blood*. Jun. 15, 2004; 103(12):4619-4621.
55. Fernando M R, Reyes J L, Iannuzzi J, Leung G, McKay D M. The pro-inflammatory cytokine, interleukin-6, enhances the polarization of alternatively activated macrophages. *PLoS One*. 2014; 9(4):e94188.
56. Choi J S, Kim K H, Lau L F. The matricellular protein CCN1 promotes mucosal healing in murine colitis through IL-6. *Mucosal Immunol*. November 2015; 8(6):1285-1296.
57. Kondo M, Yamaoka K, Sakata K, et al. Contribution of the Interleukin-6/STAT-3 Signaling Pathway to Chondrogenic Differentiation of Human Mesenchymal Stem Cells. *Arthritis Rheumatol*. May 2015; 67(5):1250-1260.
58. Hallahan D E, Virudachalam S. Intercellular adhesion molecule 1 knockout abrogates radiation induced pulmonary inflammation. *Proc Natl Acad Sci USA*. Jun. 10, 1997; 94(12):6432-6437.
59. Chow A, Huggins M, Ahmed J, et al. CD169(+) macrophages provide a niche promoting erythropoiesis under homeostasis and stress. *Nat Med*. April 2013; 19(4):429-436.
60. Jacobsen R N, Perkins A C, Levesque J P. Macrophages and regulation of erythropoiesis. *Curr Opin Hematol*. May 2015; 22(3):212-219.
61. Wang Z, Xu L, Hu Y, et al. miRNA let-7b modulates macrophage polarization and enhances tumor-associated macrophages to promote angiogenesis and mobility in prostate cancer. *Sci Rep*. May 9, 2016; 6:25602.

We claim:
1. A method for generating an educated macrophage, the method comprising the steps of:
isolating extracellular vesicles from a mesenchymal stem cell previously exposed to lipopolysaccharide (LPS), and
co-culturing a CD14+ cell with the extracellular vesicles in vitro until the CD14+ cell acquires an anti-inflammatory macrophage phenotype, wherein the mesenchymal stem cell is exposed to about 800 ng/ml to about 1200 ng/ml LPS.

2. The method of claim 1, wherein the CD14+ cell and the extracellular vesicles are co-cultured for at least 2 days.

3. The method of claim 1, wherein the mesenchymal stem cell is exposed to LPS for at least 2 hours.

4. The method of claim 1, wherein the CD14+ cell is a macrophage.

5. The method of claim 1, wherein the CD14+ cell is a monocyte and wherein the CD14+ monocyte and the extracellular vesicle are co-cultured for at least 5 days.

6. A population of anti-inflammatory macrophages produced by the method of claim 1, wherein the anti-inflammatory macrophage phenotype is characterized as FLT-3L high, IL-15 high, CD73 high, CD86 low, and HLA-DR low as compared to control macrophages.

7. A method for generating an educated monocyte, the method comprising the steps of:
   isolating extracellular vesicles from a mesenchymal stem cell previously exposed to lipopolysaccharide (LPS), and
   co-culturing a CD14+ monocyte with the extracellular vesicles in vitro until the CD14+ monocyte acquires an anti-inflammatory monocyte phenotype, wherein the mesenchymal stem cell is exposed to about 800 ng/ml to about 1200 ng/ml LPS.

8. The method of claim 7, wherein the CD14+ monocyte and the extracellular vesicles are co-cultured for at least 2 hours.

9. The method of claim 8, wherein the CD14+ monocyte and the extracellular vesicles are co-cultured for at least 24 hours.

10. The method of claim 7, wherein the mesenchymal stem cell is exposed to LPS for at least 12 hours.

11. A population of anti-inflammatory monocytes produced by the method of claim 7, wherein the anti-inflammatory monocyte phenotype is characterized as PD-L1 high, CD206 low, CD163 low, IL-15 high, CD73 high, CD86 low, CD16 low and IL-6 high as compared to control monocytes.

* * * * *